United States Patent
Camargo et al.

(10) Patent No.: US 10,551,314 B2
(45) Date of Patent: *Feb. 4, 2020

(54) GAS SENSOR

(71) Applicant: ASAHI KASEI MICRODEVICES CORPORATION, Tokyo (JP)

(72) Inventors: Edson Gomes Camargo, Tokyo (JP); Satoshi Takehara, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 21 days.

This patent is subject to a terminal disclaimer.

(21) Appl. No.: 16/059,278

(22) Filed: Aug. 9, 2018

(65) Prior Publication Data

US 2019/0072489 A1     Mar. 7, 2019

Related U.S. Application Data

(63) Continuation of application No. 15/022,976, filed as application No. PCT/JP2014/004955 on Sep. 26, 2014, now Pat. No. 10,082,464.

(30) Foreign Application Priority Data

Sep. 27, 2013  (JP) .................. 2013-202031
Jan. 29, 2014  (JP) .................. 2014-014700

(51) Int. Cl.
*G01N 21/00*   (2006.01)
*G01N 21/61*   (2006.01)
(Continued)

(52) U.S. Cl.
CPC .......... *G01N 21/61* (2013.01); *G01N 21/031* (2013.01); *G01N 21/0303* (2013.01);
(Continued)

(58) Field of Classification Search
CPC ..................... G01N 21/61; G01N 21/0303
See application file for complete search history.

(56) References Cited

U.S. PATENT DOCUMENTS 5,811,812 A   9/1998 Williams et al.
5,942,755 A   8/1999 Dreyer
(Continued)

FOREIGN PATENT DOCUMENTS

CN      203069508 U    7/2013
EP      1 724 567 A1   11/2006
(Continued)

OTHER PUBLICATIONS

International Preliminary Report on Patentability dated Apr. 7, 2016, for International Patent Application No. PCT/JP2014/004955.
(Continued)

*Primary Examiner* — Rebecca C Bryant
(74) *Attorney, Agent, or Firm* — Morgan, Lewis & Bockius LLP

(57) ABSTRACT

A small-size reliable gas sensor that can reduce a measurement error can be provided. The gas sensor includes a first light source; a first sensor unit and a second sensor unit disposed to receive light output from the first light source; a first substrate having a first principal surface on which the first light source and the first sensor unit are provided; and a second substrate having a first principal surface on which the second sensor unit is provided. The first sensor unit is disposed at a location where light output from the first light source and reflected on the second principal surface strikes the first principal surface of the first substrate.

20 Claims, 27 Drawing Sheets

(51) Int. Cl.
  *G01N 21/3504* (2014.01)
  *G01N 21/03* (2006.01)
  *H01L 31/0304* (2006.01)
  *H01L 31/167* (2006.01)

(52) U.S. Cl.
  CPC ..... *G01N 21/3504* (2013.01); *H01L 31/0304* (2013.01); *H01L 31/167* (2013.01); *G01N 2201/062* (2013.01); *G01N 2201/068* (2013.01); *G01N 2201/12* (2013.01)

(56) References Cited

U.S. PATENT DOCUMENTS

| | | |
|---|---|---|
| 6,331,704 B1 | 12/2001 | Owen |
| 8,308,348 B2 | 11/2012 | Boehm et al. |
| 2006/0263256 A1 | 11/2006 | Koshel |
| 2008/0231857 A1 | 9/2008 | Depeursinge et al. |
| 2009/0296771 A1 | 12/2009 | Boehm et al. |
| 2011/0090505 A1 | 4/2011 | Kuze et al. |

FOREIGN PATENT DOCUMENTS

| | | |
|---|---|---|
| FR | 2 871 583 A1 | 12/2005 |
| JP | 58-048481 A | 3/1983 |
| JP | 05-072130 A | 3/1993 |
| JP | 08-247889 A | 9/1996 |
| JP | 2001-503865 T | 3/2001 |
| JP | 2008-509381 A | 3/2008 |
| JP | 2008-157809 A | 7/2008 |
| JP | 2008-309583 A | 12/2008 |
| JP | 2009-257919 A | 11/2009 |
| JP | 2010-522868 A | 7/2010 |
| WO | 2007/080398 A1 | 7/2007 |
| WO | 2009/148134 A1 | 12/2009 |

OTHER PUBLICATIONS

Crowder et al., "Minimally cooled InSb/1nA1Sb LED and photodiode devices applied to nitrogen dioxide detection at ppm levels", Electronics Letters, Oct. 26, 2000, vol. 36, No. 22, pp. 1867-1869.
Aidaraliev. et. al., "Lattice-Matched GaInPAsSb/InAs Structures for Devices of Infrared Optoelectronics", Semiconductors, 2002,vol. 36, No. 8, pp. 944-949.
International Search Report dated Dec. 22, 2014, for corresponding International application No. PCT/JP2014/004955.
European Search Report issued in European Application No. 14847800.1 dated Apr. 19, 2017.

GAS SENSOR

This application is a continuation of U.S. application Ser. No. 15/022,976, filed Mar. 18, 2016, which claims priority of Japanese PCT Application No. PCT/JP2014/004955, filed on Sep. 26, 2014, which claims priority of Japanese Patent Application No. 2014-014700, filed Jan. 29, 2014 and Japanese Patent Application No. 2013-202031, filed Sep. 27, 2013, the disclosure of which is hereby incorporated by reference herein in its entirety.

TECHNICAL FIELD

The present invention relates to a gas sensor.

BACKGROUND ART

In recent years, attention has been directed to measurement for determining the presence of a gas and its concentration thereof, and especially to measurement for determining the presence of environmental gases (e.g., $CO_2$, NO, etc.) and its concentration thereof.

As sensors for measuring these gases with high accuracy, gas sensors using chemical reaction and optical gas sensors can be cited. In view of high measurement accuracy and small drift with time, optical gas sensors have received attention. An optical gas sensor includes a light source for emitting a wavelength that can be absorbed by molecules of a gas to be measured, and a sensor to detect a signal thereof.

The environmental gas significantly absorbs light with wavelengths around several micrometers (e.g., around a wavelength of 4.3 μm in the case of $CO_2$), and thus, a light source for emitting light in this wavelength band and a sensor for outputting a signal in accordance with the intensity of light in this wavelength band are required. LEDs that emit light in a mid-to-far infrared range, mainly used for nondispersive infrared gas sensors (hereinafter referred to as NDIR gas sensors), have been developed.

FIG. 29A is a conceptual view illustrative of an example configuration of an NDIR gas sensor according to a first conventional example. As illustrated in FIG. 29A, the NDIR gas sensor includes a gas cell 910, a light source 920 that emits infrared rays with a wavelength corresponding to an absorption wavelength band specific to a gas, and an infrared ray sensor 930 capable of detecting an intensity of light in this wavelength band. The light source 920 and the infrared ray sensor 930 are disposed in the gas cell 910. In a NDIR gas sensor the target gas to be measured flows or is accumulated in the gas cell 910 to that the concentration of the target gas to be measured is obtained from the amount of infrared rays absorbed by a space between the light source 920 and the infrared sensor 930 in the gas cell. Thus, when the intensity of the light source of the NDIR gas sensor changes, the absolute value of the concentration of the measured gas drifts, making impossible an accurate measurement of the concentration.

FIG. 29B is a conceptual view illustrative of an example configuration of an NDIR gas sensor according to a second conventional example. As illustrated in FIG. 29B, as a generally known technique, output ratios of both a reference sensor 931 capable of detecting light in a wavelength band that is not absorbed by a detection target gas and a detection sensor 932 capable of detecting light in a wavelength band that is absorbed by the detection target gas is obtained so that output fluctuations of the light source 920 are canceled (see, for example, PTL 1).

PTL 2 discloses an NDIR gas sensor using two wavelength bands. The gas sensor of PTL 2 includes two light sources so that light with a wavelength absorbed by a detection target gas and light with a wavelength not absorbed by the detection target gas are caused to pass through a gas cell in order to measure a concentration of a gas to be detected based on output ratios of the sensors.

CITATION LIST

Patent Literatures

PTL 1: JP 2001-503865 T
PTL 2: WO 2007/080398

SUMMARY OF INVENTION

Technical Problem

A typical NDIR sensor uses a band-pass filter with transmittance only on a specific wavelength band. In the case of detecting carbon dioxide, for example, a detection target gas is detected by using a reference band-pass filter f1 transmissive to light in a wavelength band of about 3.9 μm that is substantially not absorbed by carbon dioxide and a band-pass filter f2 for absorption wavelength transmissive only to light in a wavelength band around 4.3 μm (4.3 μm±(100 to 300 nm)) that is absorbed by carbon dioxide. In this sensor, two band-pass filters, i.e. a reference band-pass filter and a band-pass filter for absorption wavelength, are needed, and these band-pass filters require sensors that are independent of each other (see FIG. 29B and PTL 1). Thus, a large number of components are used, which hinders simplification of a system.

In a manner similar to the technique of PTL 2, in the case of using light sources for two different wavelengths, a large number of components are used, and thus signal processing is complicated. In addition, disadvantageously, in a case where a difference in light amount occurs between the two light sources because of changes in light amount and sensitivity depending on temperatures of the light sources and the sensors or degradation of the light sources, temperature compensation in an operation as a gas sensor cannot be obtained.

Furthermore, it is extremely difficult to make a compensation to eliminate temperature dependence in cases where the change in signal depending on the temperatures of the light sources and the sensors is larger than the change in signal depending on the change in gas concentration. To solve such problems, a technique of increasing an optical path length may be employed. This technique, however, increases the size of the entire sensor and, in addition, attenuation of light from the light sources increases so that an SN ratio of a signal detected by the sensor decreases, and a variation in measurement by the gas sensor increases. As a result, it is difficult to obtain a gas sensor with high accuracy.

On the other hand, as another possible technique, no reference filters are used, and a change in the intensity of light emitted from a light source is regularly calibrated for use in an environment where a carbon dioxide concentration is known to a certain degree, e.g., in the outdoor air. However, an error in a measured value is disadvantageously large in a case where carbon dioxide in a known concentration cannot be introduced or a case where the intensity of the light source significantly changes more than expected.

The present invention has been made in view of the foregoing problems, and has an object of providing a small-size reliable gas sensor that can reduce a measurement error and has a simple configuration.

Solution to Problems

An inventor of the present invention has intensively studied to solve the problems described above, to conceive a gas sensor as follows.

That is, a gas sensor according to an aspect of the present invention is characterized by including: a first light source; a first sensor unit and a second sensor unit disposed to receive light output from the first light source; a first substrate having a first principal surface and a second principal surface opposite to the first principal surface, the first light source and the first sensor unit being provided on the first principal surface of the first substrate; and a second substrate having a first principal surface and a second principal surface opposite to the first principal surface, the second sensor unit being provided on the first principal surface of the second substrate, wherein the first sensor unit is disposed at a location where light output from the first light source and reflected on the second principal surface of the first substrate strikes the first principal surface of the first substrate.

The gas sensor may be characterized by further including a computation unit configured to receive an output signal from the first sensor unit and an output signal from the second sensor unit.

The gas sensor may be characterized in that the first sensor unit and the second sensor unit have an identical temperature characteristic.

The gas sensor may be characterized in that the first substrate and the second substrate are disposed adjacent to each other with side faces thereof facing each other, and the gas sensor further includes a light-blocking portion disposed between the first substrate and the second substrate.

The gas sensor may be characterized by further including: a gas cell; and a light reflection unit disposed away from the first substrate and the second substrate in the gas cell and configured to reflect light emitted from the second principal surface of the first substrate toward the second sensor unit.

The gas sensor may be characterized by further including a control layer disposed on the second principal surface of the first substrate, and configured to control an amount of light output from the first light source and scattered in the first substrate and an amount and a radiation angle of light output from the first light source and radiated from the second principal surface of the first substrate to a space in the gas cell.

The gas sensor may be characterized by further including a light reflection layer disposed on the second principal surface of the first substrate and configured to reflect light output from the first light source toward the first sensor unit.

The gas sensor may be characterized in that the first sensor unit, the second sensor unit, and the first light source are made of an identical material and have an identical laminated structure.

The gas sensor may be characterized in that the laminated structure is a diode structure including a least two types of layers of a p-type semiconductor and an n-type semiconductor and include indium or antimony.

The gas sensor may be characterized by further including an optical filter disposed on an optical path along which light emitted from the second principal surface of the first substrate strikes the second sensor unit, the optical filter being transmissive only to a specific wavelength band.

The gas sensor may be characterized in that each of the first sensor unit and the second sensor unit includes a plurality of light-receiving portions having an identical structure, and the number of light-receiving portions of the first sensor unit is different from that of the second sensor unit.

The gas sensor may be characterized in that the first substrate and the second substrate are made of an identical material.

The gas sensor may be characterized by further including a second light source disposed on the first principal surface of the second substrate, wherein the second sensor unit is at a location where light output from the second light source and reflected on the second principal surface of the second substrate strikes the second sensor unit.

The gas sensor may be characterized by further including a light reception/emission control unit configured to supply electric power to the first light source and the second light source and to receive an output signal from the first sensor unit and an output signal from the second sensor unit.

The gas sensor may be characterized in that, while the light reception/emission control unit supplies electric power to a light-emitting portion of one of the first light source or the second light source, the light reception/emission control unit does not supply electric power to a light-emitting portion of the other.

The gas sensor may be characterized in that the light reception/emission control unit supplies an identical level of electric power to the first light source and the second light source.

The gas sensor may be characterized in that the light reception/emission control unit controls electric power to be supplied to the first light source and electric power to be supplied to the second light source in such a manner that the first sensor unit and the second sensor unit temperatures become identical.

The gas sensor may be characterized in that the light reception/emission control unit includes a first temperature measuring unit configured to measure a temperature of the first sensor unit, and a second temperature measuring unit configured to measure a temperature of the second sensor unit.

The gas sensor may be characterized in that the light reception/emission control unit, calculates a temperature of the first sensor unit based on a resistance value of the first sensor unit, and calculates a temperature of the second sensor unit based on a resistance value of the second sensor unit.

The gas sensor may be characterized in that the light reception/emission control unit controls at least one selected from the group consisting of width, amplitude, and duty ratio of a pulse of current or voltage of electric power to be supplied to the first light source and the second light source.

The gas sensor may be characterized in that the light reception/emission control unit drives the first light source at a frequency F1 and the second light source at a frequency F2 (where F1≠F2).

Advantageous Effects of Invention

According to an aspect of the present invention, a small-size and reliable gas sensor that can reduce measurement error and has a simple configuration can be provided.

DESCRIPTION OF EMBODIMENTS

Figure 1:
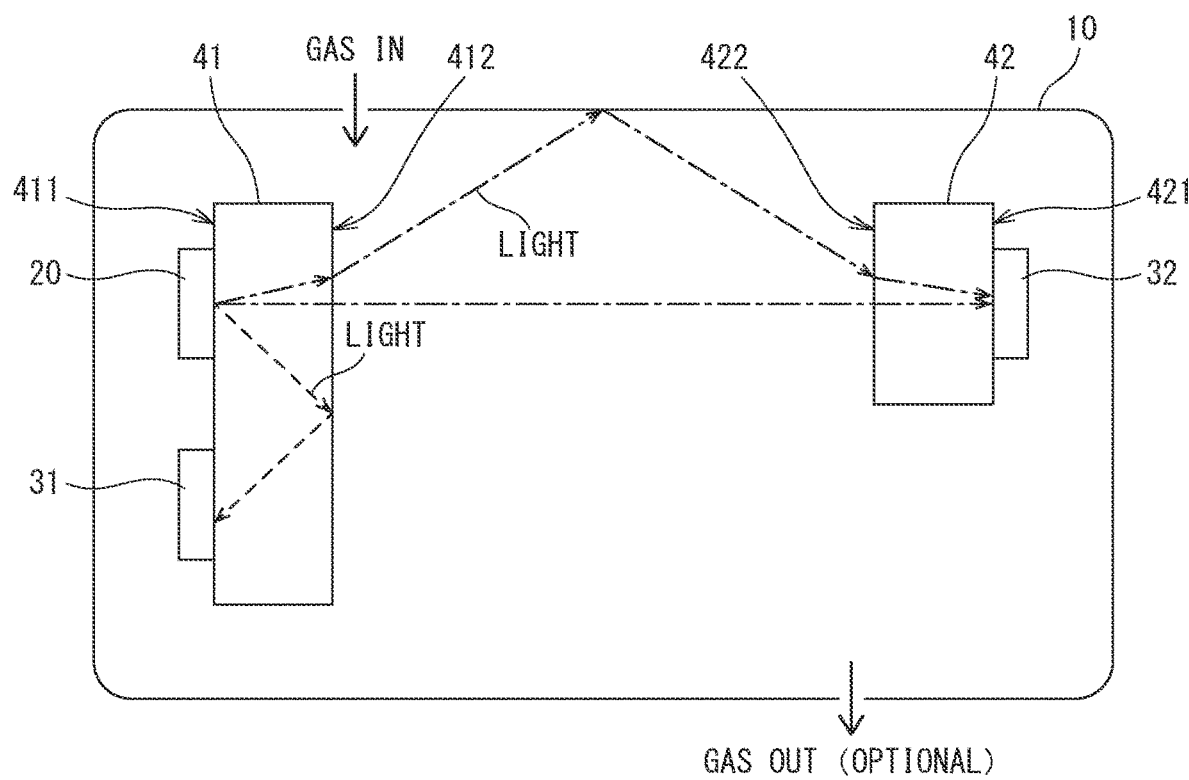
FIG. 1 is a view illustrative of an example configuration of a gas sensor according to a first embodiment of the present invention.

An embodiment for carrying out the present invention (hereinafter referred to as the present embodiment) will be described. First, as a first aspect, which is an example of the present embodiment, a gas sensor including one light source will be described. Next, as a second aspect, which is another example of the present embodiment, a gas sensor including two or more light sources will be described. Thereafter, other specific aspects (i.e., specific examples) of the present embodiment, first through twenty-first embodiments will be described.

<First Aspect>

A gas sensor according to the first aspect is a gas sensor including a first light source and first and second sensor units that are disposed to receive light output from the first light source. The gas sensor having this configuration can be used as a nondispersive infrared gas sensor.

The gas sensor includes a first substrate having a first principal surface (e.g., a front surface) and a second principal surface (e.g., a back surface) opposite to the first principal surface, and a first light source and a first sensor unit are provided on the first principal surface. The gas sensor also includes a second substrate having a first principal surface (e.g., a front surface) and a second principal surface (e.g., a back surface) opposite to the first principal surface, and a second sensor unit is provided on the first principal surface. The first sensor unit is disposed at a location where light output from the first light source and reflected on the second principal surface of the first substrate strikes the first principal surface of the first substrate. This configuration enables precise compensation for a change with time due to degradation of a first light source output and an output variation depending on temperature during operation, without providing an optical filter (e.g., a band-pass filter) on an optical path extending from the first light source to the first sensor unit.

The gas sensor of the first aspect may further include a gas cell capable of introducing a detection target gas. Since the gas sensor previously includes a predetermined gas cell, a predetermined correction computation for more accurate gas concentration computation, for example, can be performed based on, for example, an optical path and material properties of the predetermined gas cell.

The gas sensor of the first aspect preferably further includes a computation unit that receives an output signal from the first sensor unit and an output signal from the second sensor unit. Based on the output signal from the first sensor unit and the output signal from the second sensor unit, a gas concentration can be computed. With a technical idea of using the output signal from the first sensor unit provided on the plane of the substrate on which the first light source is provided for a computation of a gas concentration as a reference signal, gas sensors according to embodiments of the present invention can more effectively obtain the advantage of reducing a measurement error with a simple configuration using no reference filters, as compared to a conventional technique. Here, a computation of a gas concentration may consist on a computation of an absolute value of a gas concentration in the air, or a computation for determining whether the gas concentration exceeds a predetermined threshold.

In the gas sensor of the first aspect, the first sensor unit and the second sensor unit preferably have an identical temperature characteristic. In the present embodiment, the "identical temperature characteristic" refers to a state in which a temperature characteristic is generally uniform to such a degree that does not hinder advantages of the present invention. Specifically, suppose in a condition in which no detection target gas is present, an output signal from the first sensor unit is S1 and an output signal from the second sensor unit is S2 under a sensor temperature Tx in a typical operating temperature range (e.g., a range from 0° C. to 50° C.) of a gas sensor. In this condition, in a case where when the temperature changes by 1° C., that is, when the sensor temperature changes to Tx±1° C., the output signal from the first sensor unit changes to a×S1 and the output signal from the second sensor unit changes to b×S2, a/b is preferably greater than or equal to 0.8 and less than or equal to 1.2, more preferably greater than or equal to 0.9 and less than or equal to 1.1, and much more preferably greater than or equal to 0.99 and less than or equal to 1.01, per 1° C.

A ratio between a maximum value and a minimum value of a ratio (a/b[/° C.]) between coefficients of change in output of the first sensor unit and the second sensor unit per 1° C. is preferably greater than or equal to 0.8 and less than or equal to 1.2. This is because in this range, a concentration of a detection target gas can be accurately compensated for, independently of an environmental temperature of the gas sensor. Specifically, output coefficients (a and b) of changes of the first sensor unit and the second sensor unit obtained when the temperatures of the first sensor unit and the second sensor unit change from 0° C. to 50° C. are obtained. Then, an a/b/ΔT ratio with a temperature change of ΔT is calculated. In this manner, the ratio in coefficient of change between the outputs per 1° C. described above can be determined.

A method for setting the maximum value and the minimum value of the ratio in coefficient of change between the outputs of the first sensor unit and the second sensor unit per 1° C. in the range described above can be a method of forming the first sensor unit and the second sensor unit in such a manner that the first sensor unit and the second sensor unit have an identical laminated structure made of an identical material. In a case where the first sensor unit and the second sensor unit are made of the identical material and have the identical laminated structure, the first sensor unit and the second sensor unit theoretically the identical temperature characteristic.

To make the temperature characteristic of the first sensor unit and the second sensor unit identical to each other, the first sensor unit and the second sensor unit preferably have an identical laminated structure, and are preferably formed at the same time (i.e., layers constituting the laminated structures are formed at the same time for the first sensor unit and the second sensor unit).

To obtain a high S/N ratio of the entire gas sensor, the areas in the substrates occupied by the first sensor unit and the second sensor unit may differ from each other. For example, in a case where the intensity of light incident on the first sensor unit is high, even when the light-receiving surface area of the first sensor unit is reduced to such a degree that does not reduce the S/N ratio, an S/N ratio (minimum resolution of a gas concentration indicated value) of the entire gas sensor does not decrease. Thus, the light-receiving surface area of the first sensor unit can be reduced, and the area occupied by the first light source can be increased accordingly. As a result, the S/N ratio of the entire gas sensor can be enhanced.

Each of the first sensor unit and the second sensor unit is preferably constituted by a large number of light-receiving portions. In this case, the light-receiving surface area is proportional to the number of light-receiving portions, and a higher S/N ratio can be obtained as the light-receiving surface area increases. Even in a case where the first sensor unit and the second sensor unit have different light-receiving surface areas, neither a spectral sensitivity characteristic nor a temperature characteristic changes, and thus, advantages of the present invention can be still obtained. Suppose the number of light-receiving portions constituting the first sensor unit is n and the number of light-receiving portions constituting the second sensor unit is m, the ratio (n:m) in the number of light-receiving portions can be about 1/500, may be about 1/100 or about 1/10, depending on the situation. The ratio in the number of light-receiving portions is preferably designed depending on the design of the gas cell or light-emission performance of the first light source.

Since the first sensor unit and the second sensor unit are made of an identical material and formed on an identical substrate by an identical process, the first sensor unit and the second sensor unit have an identical spectral sensitivity characteristic and an identical temperature characteristic, thereby maximizing advantages of the present invention. Here, the spectral sensitivity characteristic refers to the sensitivity at each wavelength. As will be described later, an optical filter (e.g., a band-pass filter) that selects light is provided on the second principal surface of the first substrate so that a wavelength band of light incident on the first sensor unit and the second sensor unit can be selected. Such an optical filter needs to be provided on an optical path, and may be provided on the second principal surface(s) of the first substrate and/or the second substrate. The optical filter can allow a transmission characteristic having a narrow full width at half maximum (several tens of nanometers to several hundreds of nanometers), thereby a specific wavelength can be easily selected. In a case where the gas introduced into a gas cell is a mixed gas and an absorption wavelength of a detection target gas is close to an absorption wavelength of another gas (an interference gas), an optical filter can enhance selectivity of the gas sensor and enables accurate measurement of a concentration of the target gas without influence of the interference gas. For this reason, an optical filter is preferably provided.

From the viewpoint of efficiency in utilizing a substrate area, the first sensor unit and the second sensor unit preferably have large numbers of light-receiving portions with identical configuration, but the number of light-receiving portions of the first sensor unit may differ from that of the second sensor unit. The difference in the number of light-receiving portions is not specifically limited. However, since light-receiving portions provided on the substrate on which the first light source is mounted can absorb a large number of luminous fluxes per a unit area than light-receiving portions provided on a different substrate on which the first light source is not provided, the light-receiving surface area of the first substrate can be made smaller than the light-receiving surface area of the second substrate in general.

Thus, to keep a balance of signal S/N ratio between the first sensor unit and the second sensor unit without waste, the number of light-receiving surface areas (the number of light-receiving portions) preferably differs between the first sensor unit and the second sensor unit. Since the gas sensor of the first aspect calculates a concentration based on the output signals (Ip1 and Ip2) from the first sensor unit and the second sensor unit, the minimum resolution of the entire gas sensor is determined based on the S/N ratios of the first sensor unit and the second sensor unit.

The output signal ratio (Ip1/Ip2) varies depending on material properties of the first substrate and the second substrate, processing methods of the second principal surface of the first substrate and the second principal surface of the second substrate, the presence of a control layer, and optical properties thereof. As will be described below, when the first substrate and the second substrate are designed to have an appropriate output signal ratio, a gas sensor having a desired accuracy can be designed to have an enhanced efficiency in using the substrates while reducing the size by minimizing the area of the sensor units.

Components of the gas sensor will now be described in detail.

[Gas Cell]

In the gas sensor of the first aspect, the gas cell is not specifically limited as long as a detection target gas can be introduced therein. That is, the gas cell only needs to have an inlet for the detection target gas. From the viewpoint of enhancing accuracy in real-time detection of a detection target gas, the gas cell preferably includes an outlet in addition to the inlet.

A material for the gas cell is not specifically limited. Examples of the material include a metal, glass, ceramics, and stainless steel, but the material for the gas cell is not limited to these materials. From the viewpoint of enhancing detection sensitivity, the material for the gas cell is preferably a material having a small coefficient of absorbing light output from the first light source and a high reflectance. Specifically, the material is preferably a metal housing made of aluminum, or a resin housing coated with an alloy including aluminum, gold, or silver, or a layered structure including these metals. From the viewpoint of reliability and a change with time, a resin housing coated with gold or an alloy layer including gold is preferable.

From the viewpoint of causing light from the second principal surface opposite to the first principal surface of the first substrate to efficiently strike the second sensor unit, a part of an inner wall of the gas cell is preferably covered with a material having a high reflectance. From the viewpoint of enhancing reflectance, the roughness of the inner wall of the gas cell is preferably less than or equal to 10 μm, more preferably less than or equal to 5 μm, and much more preferably less than or equal to 1 μm.

[First Substrate]

In the gas sensor of the first aspect, the first substrate includes the first light source and the first sensor unit on the first principal surface. A material for the first substrate is not specifically limited. Examples of the material for the first substrate include Si, GaAs, sapphire, InP, InAs, and Ge. However, the material for the first substrate is not limited to these materials, and may be selected in accordance with a wavelength band used. From the viewpoint of electrically insulating the first sensor unit from the first light source easily, a semi-insulating substrate is preferably used. From the viewpoint of capability of fabricating a semi-insulating substrate and increasing an opening diameter, a GaAs substrate is especially preferable. From the viewpoint of enhancing measurement sensitivity, the material for the first substrate is preferably a material highly transmissive (with high transmittance) to light output from the first light source. From the viewpoint of accurate compensation for an output variation of the first light source, the material for the first substrate is preferably a material with which light output from the first light source is efficiency reflected on the second principal surface.

A material for the first sensor unit, the second sensor unit, and the first light source is preferably a Group III-V based compound semiconductor, more preferably a compound semiconductor composed of at least one type of Group III elements selected from the group consisting of indium (In), aluminum (Al), and gallium (Ga) and at least one type of Group V atoms selected from the group consisting of antimony (Sb) and arsenic (As), and much more preferably a compound semiconductor including at least one of InSb, AlInSb, GaInSb, or AsInSb. In a case where a detection target gas is $CO_2$, AlInSb or GaInSb can be used for detecting $CO_2$ absorption around a wavelength of 4.3 μm. In the case of detecting a gas such as vaporized alcohol, a longer wavelength (9 to 10 μm) is needed. In this case, AsInSb is preferably used.

From the viewpoint of light-extraction efficiency and light reflection and scattering efficiency, the first substrate preferably includes, on the second principal surface of the first substrate, a control layer for controlling the amount and the reflection/scattering angle of light emitted from the first light source and scattered in the substrate, as well as the radiation angle of the light emitted from the first light source which is radiated into the cell, from the second principal surface of the first substrate. Since a typical substrate material has a high refractive index, it is difficult to take light out of the substrate, and a large amount of light output from the first light source is scattered in the substrate. In the gas sensor of the first aspect, the control layer is provided on the second principal surface of the first substrate so that the entire sensor can be designed to have a high S/N ratio (obtain high resolution). Specific examples of the control layer include an anti-reflection film, a laminated film composed of a large number of materials having different refractive indexes, a coarsed layer, and a combination thereof.

[First Light Source]

In the gas sensor of the first aspect, the first light source is formed on the first principal surface of the first substrate. The first light source is not specifically limited as long as the first light source outputs light including a wavelength that can be absorbed by a detection target gas. A specific configuration of the first light source may be any configuration as long as the first light source can be formed on the first principal surface of the first substrate. Specific examples of the first light source include a MEMS and an LED. Among these devices, from the viewpoint of reducing noise due to light absorption of a mixture except the target gas, it is preferable that the first light source outputs only light in a wavelength band showing a large degree of absorption by a detection target gas. Specifically, a LED structure is preferable in some cases because its emission wavelength band can be controlled by changing the band gap in the active layer.

Figure 29A:
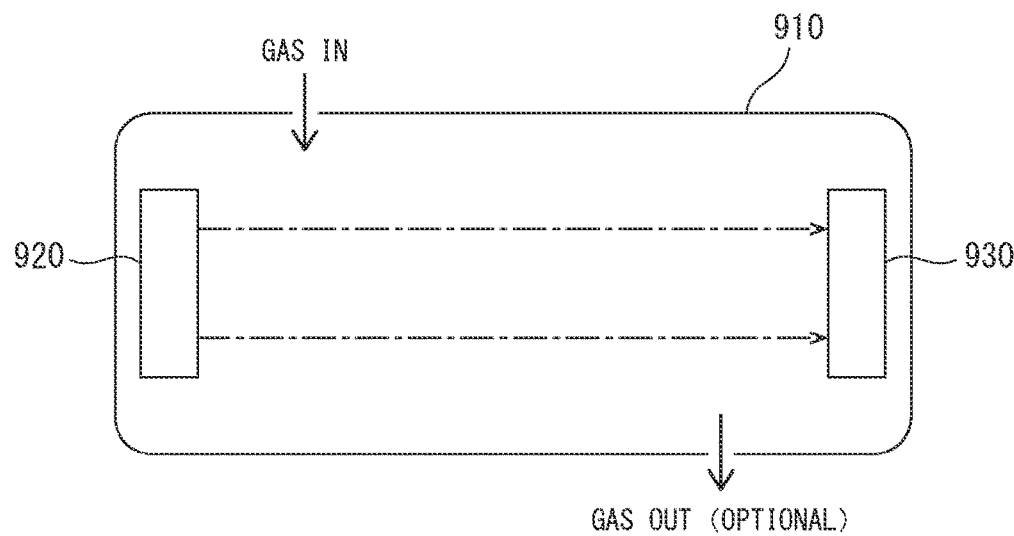
FIG. 29A is a view illustrative of a first conventional gas sensor and FIG. 29B is a view illustrative of a second conventional gas sensor.
Figure 29B:
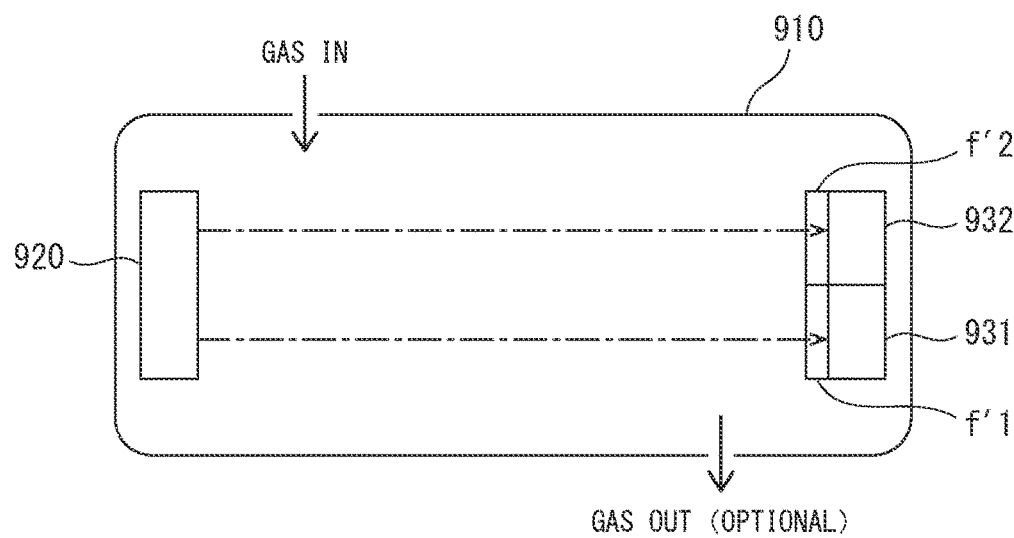

In a conventional gas sensor using two sensors illustrated in FIG. 29B, in the case of using the first light source that outputs only light in a wavelength band that can be greatly absorbed by a detection target gas, since reference band-pass filter blocks light in an absorption wavelength band of the detection target gas, an output of the reference sensor is zero, and thus, a stable gas sensor cannot be obtained. On the other hand, in the gas sensor of the first aspect, a band-pass filter does not need to be provided on an optical path extending from the first light source to the first sensor unit (serving as a reference sensor), and thus, accurate compensation for an output variation can be obtained even with the use of a first light source that outputs only light in a wavelength band that can be greatly absorbed by the detection target gas.

The first light source preferably includes a laminated structure portion having a PN junction or a PIN junction deposited by a deposition method such as molecular beam epitaxy (MBE) or chemical vapor deposition (CVD). When electric power is supplied to this laminated structure portion, the laminated structure portion operates as a light emitting diode (LED), and can emit light with a wavelength in accordance with a band gap of a material for the laminated structure portion. In a case where the laminated structure portion (called an active layer) includes In or Sb, light in an infrared region (i.e., infrared rays) can be emitted. Specifically, the use of InSb, InAlSb, or InAsSb for the active layer allows light with a wavelength of 1 to 10 µm to be output. In a case where a detection target gas is carbon dioxide, a carbon dioxide gas shows a large degree of absorption around a wavelength of 4.3 µm, and thus, InAlSb is preferably used for the active layer. By tuning the Al content to obtain an emission peak of the LED at 4.3 µm, the gas sensor can have high sensitivity and high resolution. In the case of a gas (e.g., vaporized alcohol showing absorption around 10 µm) with CO bonds showing absorption around 10 µm, InAsSb is preferably used for the active layer.

The use of the first light source of the LED enables detection of a specific gas without using an optical filter (e.g., a band-pass filter) by tuning a band gap of a material used for a light-emitting layer at an absorption wavelength of the detection target gas. In this manner, a specific gas can be detected, and a gas sensor without an optical filter can be achieved. The gas sensor using no optical filters can simplify a configuration of the gas sensor, and the embodiment can be more preferable.

[First Sensor Unit]

In the gas sensor of the first aspect, the first sensor unit is provided on the first principal surface of the first substrate. The location of the first sensor unit is not specifically limited as long as light output from the first light source and reflected on the second principal surface opposite to the first principal surface of the first substrate strikes the first sensor unit. From the viewpoint of response speed of signal processing, the laminated structure of the first sensor unit can be a diode structure having a PN junction or a PIN junction, and may include indium, antimony or either of these materials. The laminated structure may further include a mixed crystal-based material further including at least one material selected from the group consisting of Ga, Al, and As, depending on the absorption wavelength of the detection target gas. From the viewpoint of uniformizing a temperature characteristic, the material and the laminated structure of a light-receiving element of the first sensor unit are preferably similar to the material and the laminated structure of the first light source.

From the viewpoint of an S/N ratio in a case where the sensor unit is connected to a circuit (amplifier), an internal resistance of the entire light-receiving portions can be increased by providing a large number of light-receiving elements, a high S/N ratio can be obtained when the sensor unit is connected to an amplifier. Thus, the first sensor unit of the present embodiment preferably has a configuration in which light-receiving elements are connected in series.

Since the first light source and the first sensor unit are disposed on the first substrate, an amount of light incident on the first sensor unit tends to be larger than an amount of light incident on the second sensor unit. Thus, the total area of the light-receiving portions of the first sensor unit can be made smaller than the total area of the light-receiving portions of the second sensor unit. In this manner, the size of the gas sensor can be further reduced.

[Second Substrate]

In the gas sensor of the first aspect, the second substrate is not specifically limited as long as the second sensor unit is provided on the first principal surface. Light incident from the second principal surface passes through the inside of the second substrate, and strikes the second sensor unit.

A material for the second substrate is not specifically limited. For example, a Si substrate, a GaAs substrate, or a sapphire substrate may be used, but the material for the second substrate is not limited to these materials. From the viewpoint of enhancing measurement sensitivity, the material for the second substrate is preferably a material highly transmissive to light incident from the second principal surface.

From the viewpoint of size reduction, the second substrate is preferably disposed to be adjacent to the first substrate with side surfaces thereof facing each other and a light-blocking portion is preferably disposed between the first substrate and the second substrate. The thus-configured gas sensor preferably includes a light reflection unit described later. The light-blocking portion described above is preferably disposed at a joint portion between the first substrate and the second substrate. The light-blocking portion is preferably provided because the light-blocking portion can prevent light output from the first light source from striking the second sensor unit without passing a space in the gas cell. Thus, in this case, detection sensitivity (a signal change due to a change in gas concentration) can be enhanced.

[Second Sensor Unit]

In the gas sensor of the first aspect, the second sensor unit is not specifically limited as long as the second sensor unit is disposed on the second substrate. As described above, from the viewpoint of causing the second sensor unit and the first sensor unit to have an identical temperature characteristic, the second sensor unit and the first sensor unit are preferably formed on an identical substrate in their fabrication process, and more preferably have an identical laminated structure.

From the viewpoint of response speed of signal processing, the laminated structure of the second sensor unit is preferably a diode structure including a PN junction or a PIN junction and includes a material of indium or antimony.

From the viewpoint of enhancing measurement sensitivity, an optical filter transmissive only to light in a specific wavelength band is preferably provided on an optical path along which light radiated from the second principal surface of the first substrate strikes the second sensor unit. In a case where light output from the first light source is in a wide wavelength band, the presence of the optical filter is especially preferable.

The first substrate provided with the first sensor unit and the second substrate provided with the second sensor unit are originally made from the same wafer. In a case where the first sensor unit and the second sensor unit have similar laminated structures, variations in sensitivity characteristic and temperature characteristic of sensitivity between the first sensor unit and the second sensor unit are reduced, thereby enhancing advantages of the present invention. Specifically, suppose the sensitivity of the first sensor unit is Ri2 ($\lambda$) [A/W] and the sensitivity of the second sensor unit 2 is Ri2 ($\lambda$) [A/W], |Ri2 ($\lambda$)−Ri1 ($\lambda$)|/(Ri1 ($\lambda$)) only needs to be within 20%, preferably less than or equal to 10%, and much more preferably less than or equal to 5%. More preferably, |Ri2 ($\lambda$)−Ri1 ($\lambda$)|/(Ri1 ($\lambda$)) is within 2%, and further less than or equal to 1%. Then, advantages of the present invention can be enhanced, and compensation for temperature and a change with time with ultra-high accuracy can be obtained.

[Light Reflection Unit]

From the viewpoint of enhancing detection sensitivity to a detection target gas, the gas sensor of the first aspect preferably includes a light reflection unit in a space of the gas cell facing the second principal surfaces of the first substrate and the second substrate. That is, a light reflection unit is preferably provided at a location separated from the first substrate and the second substrate in the gas cell and facing the second principal surface of the first substrate and the second principal surface of the second substrate. The light reflection unit preferably reflects light radiated from the second principal surface of the first substrate and causes the reflected light to strike the second sensor unit. To make the light to strike the second sensor unit efficiently, the light reflection unit is preferably a light-collecting type light reflection unit.

[Light-Blocking Portion]

All the light emitted from the first light source and input to the second sensor unit is preferably light that has passed through the space in the gas cell. To achieve this configuration, a technique of disposing the first substrate provided with the first light source and the first sensor unit and the second substrate provided with the second sensor unit in such a manner that the first substrate is opposite to the second substrate may be employed. On the other hand, to reduce the size of the entire gas sensor, the first substrate and the second substrate are preferably disposed adjacent each other with their side surfaces facing each other. However, when the first substrate and the second substrate are merely disposed adjacent to each other, part of light emitted from the first light source might fail to pass through the space in the gas cell to be input to the second sensor unit so that a signal change depending on a change in gas concentration can serve as a signal component (offset) that does not depend on a change in gas concentration, leading to the possibility of a decrease in sensitivity of the gas sensor. Thus, in the case of disposing the first substrate and the second substrate adjacent to each other as described above, a light-blocking portion is preferably provided between the first substrate and the second substrate.

<Second Aspect>

Then, as a gas sensor according to a second aspect, 2-light source 2-sensor gas sensor will be described. Description and preferable configurations of components of this gas sensor are applicable to the first aspect and specific embodiments below, for example, independently of one another or in combination.

The gas sensor of the second aspect further includes a second light source provided on a first principal surface of a second substrate, in addition to the configuration of the gas sensor of the first aspect. The second sensor unit is preferably disposed at a location where light emitted from the second light source and reflected on a second principal surface opposite to a first principal surface of the second substrate strikes the second sensor unit.

This configuration allows light output from the first light source to pass through an optical path in a first substrate serving as an environment independent of the presence of a gas and a concentration of the gas, for example, and to strike a first sensor unit (a light-receiving element for monitoring when viewed from the first light source). Thus, even in a case where a light emission characteristic of the first light source changes due to a change in application environment or deterioration with time, the state of a space can be correctly detected by using the second sensor unit (a light-receiving element for detecting a state when viewed from the first light source).

The same holds for light output from the second light source. That is, light output from the second light source passes through the optical path in the second substrate serving as an environment independent of the presence of a gas and a concentration of the gas, for example, and strikes the second sensor unit (a light-receiving element for monitoring when viewed from the second light source). Thus, even in a case where the light emission characteristic of the second light source changes due to a change in application environment or deterioration with time, the state of a space can be correctly detected by using the first sensor unit (a light-receiving element for monitoring when viewed from the second light source).

In the gas sensor of the second aspect, the first sensor unit and the second sensor unit preferably have an identical temperature characteristic. In the present embodiment, the "identical temperature characteristic" refers to a state in which a temperature characteristic is generally uniform to such a degree that does not hinder advantages of the present invention. Specifically, in the case of application for detecting a gas, suppose in a condition in which no detection target gas is present, an output signal from the first sensor unit is S1 and an output signal from the second sensor unit is S2 under a sensor temperature Tx in a typical operating temperature range (e.g., a range from 0° C. to 50° C.) of a gas sensor. In this condition, in a case where when the temperature changes by 1° C., that is, when the sensor temperature changes to Tx±1° C., the output signal from the first sensor unit changes to a×S1 and the output signal from the second sensor unit changes to b×S2, a/b is preferably greater than or equal to 0.8 and less than or equal to 1.2, more preferably greater than or equal to 0.9 and less than or equal to 1.1, and much more preferably greater than or equal to 0.99 and less than or equal to 1.01, per 1° C.

A ratio between a maximum value and a minimum value of a ratio (a/b[/° C.]) between an output coefficient a of change of the first sensor unit per 1° C. and an output coefficient b of change of the second sensor unit per 1° C. is preferably greater than or equal to 0.8 and less than or equal to 1.2. This is because in this range, variations in signals of emitted light and received light can be compensated for based on the output of the first sensor unit, independently of the application environmental temperature of the gas sensor, even in a case where a light emission characteristic of the first light source changes so that the state of a space can be correctly detected by using the second sensor unit. Similarly, in a case where the light emission characteristic of the second light source changes, variations in signals of emitted light and received light can be compensated based on the output of the second sensor unit, independently of the environmental temperature of the gas sensor so that the state of the space can be correctly detected by using the first sensor unit.

Specifically, output coefficients (a and b) of changes of the first sensor unit and the second sensor unit obtained when the temperatures of the first sensor unit and the second sensor unit change from 0° C. to 50° C. are obtained. Then, an a/b/$\Delta$T ratio with a temperature change of $\Delta$T is calculated. In this manner, the ratio in coefficient of change between the outputs per 1° C. described above can be determined.

A method for setting the maximum value and the minimum value of the ratio in coefficient of change between the outputs of the first sensor unit and the second sensor unit per 1° C. in the range described above can be a method of forming the first sensor unit and the second sensor unit in such a manner that the first sensor unit and the second sensor unit have an identical laminated structure made of an identical material. In this case where the first sensor unit and the second sensor unit have the identical laminated structure made of the identical material, the first sensor unit and the second sensor unit have theoretically identical temperature characteristic.

To make the temperature characteristic of the first sensor unit and of the second sensor unit identical to each other, the first sensor unit and the second sensor unit preferably have an identical laminated structure, and are preferably formed at the same time (i.e., layers constituting the laminated structures are formed at the same time for the first sensor unit and the second sensor unit).

In a case where the first sensor unit and the second sensor unit are formed on the identical substrate, made of the identical material by the same process at the same time, the first sensor unit and the second sensor unit have an identical spectral sensitivity characteristic and an identical temperature characteristic, thereby enhancing advantages of the present invention. Here, the spectral sensitivity characteristic refers to sensitivity at each wavelength.

As will be described later, an optical filter (e.g., a bandpass filter) that selects light is provided on the second principal surface of at least one of the first substrate or the second substrate so that a wavelength band of light incident on at least one of the first sensor unit or the second sensor unit can be selected. The optical filter can obtain a transmission characteristic (several tens of nanometers to several hundreds of nanometers) having a narrow full width at half maximum, thereby easily selecting a specific wavelength.

From the viewpoint of efficiency in utilizing a substrate area, the first sensor unit and the second sensor unit preferably have large numbers of light-receiving portions with an identical configuration in such a manner that the number of light-receiving portions, and the number of light-receiving portions of the first sensor unit is preferably equal to that of the second sensor unit.

In the gas sensor of the second aspect, based on the output signal (Ip1) from the first sensor unit and the output signal (Ip2) from the second sensor unit, the state of the space formed from a light-emitting portion to the sensor unit is detected (e.g., a concentration of a detection target substance in the space is calculated). Thus, the minimum resolution of the gas sensor is determined based on the S/N ratios of the first sensor unit and the second sensor unit.

In the present embodiment, a light reception/emission control unit that supplies electric power to the first light source and the second light source and detects output signals from the first sensor unit and the second sensor unit is provided. While the light reception/emission control unit supplies electric power to the light-emitting portion of one of the first light source or the second light source, the light reception/emission control unit does not need to supply electric power to the light-emitting portion of the other. The light reception/emission control unit may supply an identical level of electric power to the first light source and the second light source. Alternatively, the light reception/emission control unit may control electric power to be supplied to the first light source and electric power supplied to the second light source in such a manner that the first sensor unit and the second sensor unit are at an identical temperature. Embodiments using light reception/emission control units will be described later.

In a case where the first sensor unit and the second sensor unit have the same sensitivity, the first light source and the second light source have an identical light emission characteristic, and the first sensor unit and the second sensor unit are at an identical temperature, the output signal from the first sensor unit is equal to the output signal from the second sensor unit. In this case, advantages of the present invention can be enhanced.

As will be described later, in a case where the first light source and the second light source are made of compound semiconductor laminated portions having an identical structure and an identical composition, when the light reception/emission control unit alternately drives the first light source and the second light source or supplies an identical level of electric power to the first light source and the second light source, the amount of heat generated by the first light source and the amount of heat generated by the second light source are steadily the same so that the first light source and the second light source are at an identical temperature.

In a case where the first light source emits light, suppose an S/N ratio detected by the first sensor unit is SNR11 and an S/N ratio detected by the second sensor unit is SNR21. In a case where the second light source emits light, suppose an S/N ratio detected by the first sensor unit is SNR12 and an S/N ratio detected by the second sensor unit is SNR22. Then, an S/N ratio obtained in an optical path (from the first light source to the first sensor unit, and from the second light source to the second sensor unit) not passing through a detection target substance is expressed by Equation (1):

$$SNR_{REF}=[(SNR11)^{1/2}+(SNR22)^{1/2}]^{1/2} \qquad (1)$$

An S/N ratio obtained in light transmitted through the detection target substance (from the first light source to the second sensor unit, and from the second light source to the first sensor unit) is expressed by Equation (2):

$$SNR_{TRASM}=[(SNR12)^{1/2}+(SNR21)^{1/2}]^{1/2} \qquad (2)$$

Thus, Equation (1) and Equation (2) demonstrate that light emission and reception performed in both directions can enhance the SNR of a system, as compared to the case of performing light emission and reception in one direction.

Examples of a signal obtained from the first sensor unit include a signal $Ip_{\_REF\_1}$ in a case where the first light source emits light and a signal $Ip_{\_TRASM\_2}$ in a case where the second light source emits light. Examples of a signal obtained from the second sensor unit include a signal $Ip_{\_REF\_2}$ in a case where the second light source emits light and a signal $Ip_{\_TRASM\_1}$ in a case where the first light source emits light. The output signal ratios ($Ip_{\_TRASM\_1}/Ip_{\_REF\_1}$) and ($Ip_{\_TRASM\_2}/Ip_{\_REF\_2}$) change depending on material properties of the first substrate and the second substrate, processing methods for the second principal surface of the first substrate and the second principal surface of the second substrate, and the presence and optical properties of a control layer formed on the second principal surface of the substrate described later, for example.

[First Substrate and Second Substrate]

In the gas sensor of the second aspect, the first substrate includes the first light source and the first sensor unit on the first principal surface. The second substrate includes the second light source and the second sensor unit on the first principal surface. Examples of a material for the first substrate and the second substrate include Si, GaAs, sapphire, InP, InAs, and Ge. However, the material for the first substrate and the second substrate is not limited to these materials, and may be selected in accordance with a wavelength band used. From the viewpoint of electrically insulating the sensor unit from the light-emitting portion easily, a semi-insulating substrate is preferably used for each of the first substrate and the second substrate. From the viewpoint of capability of fabricating a semi-insulating substrate and increasing an opening diameter, a GaAs substrate is especially preferable. From the viewpoint of enhancing measurement sensitivity, the material for each of the first substrate and the substrate is preferably a material highly transmissive to light output from the light-emitting portion. From the viewpoint of accurate compensation for an output variation of the light-emitting portion, the material for each of the first substrate and the second substrate is preferably a material with which light output from the light-emitting element is efficiency reflected on the second principal surface. As will be described later, from the viewpoint of easily forming the first sensor unit, the second sensor unit, the first light source, and the second light source each having a laminated structure including indium (In) or antimony (Sb), a GaAs substrate is preferable.

A material used for each of the first sensor unit, the second sensor unit, the first light source, and the second light source is preferably a Group III-V compound semiconductor, more preferably a compound semiconductor composed of at least one type of Group III atoms selected from the group consisting of indium (In), aluminum (Al), and gallium (Ga) and at least one type of Group V atoms selected from the group consisting of antimony (Sb) and arsenic (As), and much more preferably a compound semiconductor including at least one of InSb, AlInSb, GaInSb, or AsInSb.

In the case of application to a gas sensor, it is assumed that a detection target gas is $CO_2$. In this case, to detect absorption of light around an absorption wavelength of 4.3 μm of $CO_2$, AlInSb or GaInSb can be used as a material for each of the first sensor unit, the second sensor unit, the first light source, and the second light source. In the case of detecting a gas such as vaporized alcohol, a longer wavelength (9 to 10 μm) is needed. In this case, AsInSb is preferably used for each of the first sensor unit, the second sensor unit, the first light source, and the second light source.

In a case where the first sensor unit, the second sensor unit, the first light source, and the second light source are made of a compound semiconductor having an identical film composition (i.e., a compound semiconductor laminated portion having an identical composition), advantages of the present invention can be maximized. The identical film composition can be obtained by laminating films on the same substrate by the same process. That is, the first sensor unit, the second sensor unit, the first light source, and the second light source are preferably formed on the same wafer in some cases. In addition, a pair of chips that are adjacent in a wafer plane are preferably incorporated in the same gas sensor in some cases. This configuration can reduce the composition deviation generated during a deposition process, in an assembled gas sensor, can make the first sensor unit and the second sensor unit have an identical temperature characteristic, and make the first light source and the second light source have an identical temperature characteristic, thereby enabling accurate temperature compensation.

From the viewpoint of light-extraction efficiency and light-reflection/scattering efficiency, a control layer is preferably provided on the second principal surface of the first substrate and the second principal surface of the second substrate in some cases. The control layer is a layer for controlling an amount and a reflection/scattering angle of light scattered in the substrate and an amount and a radiation angle of light output from the light-emitting element and radiated from the second principal surface of the substrate to an optical path (e.g., a gas cell in the case of a gas sensor).

Since a material typically used for a substrate has a high refractive index, it is difficult to take light out of the substrate, and a large part of light output from the light-emitting element is scattered in the substrate. In the gas sensor of the second aspect, the control layer is provided on the second principal surface of the first substrate and the second principal surface of the second principal surface so that the gas sensor can be designed to increase the S/N ratio of the entire sensor (to obtain a high resolution). Specific example of the control layer include an anti-reflection film, a laminated film composed of a large number of materials having different refractive indexes, a coarsed layer, and a combination thereof.

[First Light Source and Second Light Source]

In the gas sensor of the second aspect, the first light source is formed on the first principal surface of the first substrate, and the second light source is formed on the first principal surface of the second substrate. The first light source and the second light source are not specifically limited as long as the first light source and the second light source output light including wavelengths absorbed in a detection target substance (e.g., a gas). Configurations of the first light source and the second light source are not specifically limited as long as the first light source and the second light source can be formed on the first principal surface of the first substrate and the first principal surface of the second substrate. Specific examples thereof include a MEMS and an LED. Among these devices, from the viewpoint of reducing noise due to light absorption by a component except a detection target substance (e.g., a gas), each of the first light source and the second light source preferably outputs only light in a wavelength band that can be greatly absorbed by a detection target substance. Specifically, a LED structure is preferable in some cases because an emission wavelength band is controlled by using a band gap in an active layer.

The light-emitting element preferably includes a laminated structure portion including a PN junction or a PIN junction deposited by a deposition method such as molecular beam epitaxy (MBE) or chemical vapor deposition (CVD). When electric power is supplied to this laminated structure portion, the laminated structure portion operates as a light emitting diode (LED), and can emit light with a wavelength in accordance with a band gap of a material for the laminated structure portion. In a case where the laminated structure portion (called an active layer) includes In or Sb, light in an infrared region (i.e., infrared rays) can be emitted. Specifically, the use of InSb, InAlSb, or InAsSb for the active layer enables light emission with a wavelength of 1 to 12 μm.

A narrow band gap material in which an active layer includes In and/or Sb generally has a large temperature characteristic (a change in light emission characteristic due to a temperature of a light-emitting element itself). However, the gas sensor of the second aspect can always correctly monitor even a large change in light emission characteristic, and can always obtain a constant light emission characteristic by controlling an operation of the light-emitting element based on a result of the monitoring.

[First Sensor Unit and Second Sensor Unit]

In the gas sensor of the second aspect, the first sensor unit is formed on the first principal surface of the first substrate, and the second sensor unit is formed on the first principal surface of the second substrate. The first sensor unit is disposed at a location where light output from the first light source and reflected on the second principal surface opposite to the first principal surface of the first substrate strikes the first sensor unit. The second sensor unit is disposed at a location where light output from the second light source and reflected on the second principal surface opposite to the first principal surface of the second substrate strikes the second sensor unit.

In the light output from the first light source, suppose a length of an optical path P11 to the first sensor unit is L11, and a length of an optical path P12 to the second sensor unit is L12. In the light output from the second light source, a length of an optical path to the second sensor unit is L22, and a length of an optical path P21 to the first sensor unit is L21. In this case, from the viewpoint of signal processing, relationships L12=L21 and L11=L22 are preferably established. The gas sensor is preferably designed in such a manner that in accordance with a concentration and an absorptance of a detection target substance of the gas sensor, transmission characteristics of the optical path P12 and the optical path P21 preferably change accordingly. To obtain a high S/N ratio, the lengths L12 and the L21 are preferably designed at maximum.

From the viewpoint of response speed of signal processing, the laminated structure of each of the first sensor unit and the second sensor unit is a diode structure having a PN junction or a PIN junction, and may include a material of indium or antimony. In addition, the diode structure may include a mixed crystal-based material in which a material of indium or antimony further includes at least one material selected from the group consisting of Ga, Al, and As. From the viewpoint of uniformizing a temperature characteristic, the material and the laminated structure of the light-receiving element of the first sensor unit are preferably similar to the material and the laminated structure of the light-emitting element of the second sensor unit.

From the viewpoint of an S/N ratio in the case of connecting the sensor unit to a circuit (amplifier), the first sensor unit and the second sensor unit of the present embodiment are preferably configured in such a manner that a plurality of light-receiving elements are serially connected to each other. This is because the presence of a large number of light-receiving elements can increase an internal resistance of the entire sensor unit so that, when the sensor unit is connected to an amplifier, a high S/N ratio can be obtained.

The first substrate provided with the first sensor unit and the second substrate provided with the second sensor unit are originally (i.e., before dicing) made from the same wafer. The first sensor unit and the second sensor unit preferably have similar laminated structures. In this manner, variations in sensitivity characteristic and temperature characteristic of sensitivity between the first sensor unit and the second sensor unit are suppressed, thereby enhancing advantages of the present invention. Specifically, suppose the sensitivity of the first sensor unit is Ri1 ($\lambda$)[A/W] and the sensitivity of the second sensor unit is Ri2 ($\lambda$)[A/W]. In this case, in an operating temperature range (e.g., 0 to 50° C.), |Ri2 ($\lambda$)−Ri1 ($\lambda$)|/(Ri1 ($\lambda$)) only needs to be within 20%, preferably less than or equal to 10%, and more preferably less than or equal to 5%. More preferably, |Ri2 ($\lambda$)−Ri1 ($\lambda$)|/(Ri1 ($\lambda$)) is within 2%, and much more preferably less than or equal to 1%. Then, advantages of the present invention can be enhanced, and compensation for temperature and change with time with ultra-high accuracy can be obtained.

[Light Reflection Unit]

From the viewpoint of enhancing detection sensitivity to a detection target substance (e.g., a gas), in the gas sensor of the second aspect, a light reflection unit is preferably provided in a space outside the substrates facing the second principal surface of the first substrate and the second principal surface of the second substrate. That is, a light reflection unit is preferably provided at a location separated from the first substrate and the second substrate in the gas cell and facing the second principal surface of the first substrate and the second principal surface of the second substrate. The light reflection unit preferably reflects light emitted from the second principal surface of the first substrate and causes the reflected light to strike the second sensor unit. The light reflection unit preferably reflects light emitted from the second principal surface of the second substrate and causes the reflected light to strike the first sensor unit. To cause the light output from the first light source to strike the second sensor unit efficiency and cause the light output from the second light source to strike the first sensor unit efficiency, the light reflection unit is preferably a light-collecting type light reflection unit.

[Light-Blocking Portion]

All the light output from the first light source and incident on the second sensor unit and all the light output from the second light source and incident on the first sensor unit are preferably light that has passed through a space outside the substrates (external space). To achieve this configuration, a technique of disposing the first substrate provided with the first light source and the first sensor unit and the second substrate provided with the second sensor unit in such a manner that the first substrate and the second substrate face each other may be employed. Similarly, a technique of disposing the second substrate provided with the second light source and the second sensor unit and the first substrate provided with the first sensor unit in such a manner that the first substrate and the second substrate face each other may be employed. That is, the first substrate and the second substrate preferably face each other.

On the other hand, to reduce the size of the entire gas sensor, the first substrate and the second substrate are preferably disposed adjacent to each other with their side surfaces facing each other. However, if the first substrate and the second substrate are merely disposed adjacent to each other, part of light output from the light-emitting portion might fail to pass through the external space to be input to the light-receiving portion in the adjacent substrate so that a signal change depending on a change of state of the external space can serve as a signal component (offset) that does not depend on a change of state of the external space, leading to the possibility of a decrease in measurement sensitivity of the gas sensor. Thus, in the case of disposing the first substrate and the second substrate adjacent to each other with the side surfaces thereof facing each other as described above, a light-blocking portion is preferably provided between the side surfaces of the first substrate and the second substrate.

In the foregoing description, the first substrate and the second substrate are independent of each other. In a case where no light-blocking portion is needed, the first sensor unit, the second sensor unit, the first light source, and the second light source may be formed on a first principal surface of a common substrate. In this case, the substrate is designed in such a manner that the first sensor unit is formed near a first light source and a second sensor unit is formed near the second light source.

Advantages of Embodiment

[Advantages of First Aspect]

The first aspect has advantages (1) to (4) as follows:

(1) An optical path from the first light source to the first sensor unit is in the first substrate, and neither an optical filter (e.g., a band-pass filter) nor a space in the gas cell is present in the optical path. Thus, as compared to a case where a band-pass filter and/or a space in the gas cell is/are present in the optical path, attenuation of light in the optical path can be suppressed independently of an application environment of the gas sensor, and a decrease in an S/N ratio of a signal detected by the first sensor unit can be suppressed.

(2) Since only one first light source is sufficient, a difference in light amount does not occur between the two first light sources for different wavelengths. Thus, compensation for a measurement error due to a change in emission intensity can be obtained without regular calibration of the emission intensity of the first light source.

(3) A decrease in an S/N ratio of a signal detected by the first sensor unit can be suppressed, as described above. Compensation for a measurement error due to a change in emission intensity can be obtained without regular calibration of the emission intensity of the first light source. Thus, a variation in measurement by the gas sensor can be reduced so that the resulting gas sensor can have high accuracy and reliability.

(4) The first sensor unit does not need an optical filter. In addition, only one first light source is sufficient. In this manner, the number of components constituting the gas sensor can be reduced so that the resulting gas sensor can have a small size and a simple structure.

[Advantages of Second Aspect]

The second aspect has advantages (5) to (8) as follows:

(5) An optical path from the first light source to the first sensor unit is in the first substrate, and an optical path from the second light source to the second sensor unit is in the second substrate. Neither an optical filter (e.g., a band-pass filter) nor an external space is present in these optical paths. Thus, as compared to a case where a band-pass filter for a reference signal and/or an external space is/are present in the optical path from the first light source to the first sensor unit and the optical path from the second light source to the second sensor unit, attenuation of light in the optical paths can be suppressed independently of an application environment of the gas sensor. Thus, a decrease in an S/N ratio of a signal detected by the first sensor unit in the case of detecting an optical signal from the first light source and a decrease in an S/N ratio of a signal detected by the second sensor unit in the case of detecting an optical signal from the second light source can be suppressed.

(6) A decrease in an S/N ratio of a signal detected by the first sensor unit and a decrease in an S/N ratio of a signal detected by the second sensor unit can be suppressed, as described above. Compensation for a measurement error due to a change in emission intensity can be obtained without regular calibration of the emission intensity of the light-emitting portion. Thus, a variation in measurement by the gas sensor can be reduced so that the resulting gas sensor can have high accuracy and reliability.

(7) A temperature of the first sensor unit disposed near the first light source and a temperature of the second sensor unit disposed near the second light source are controlled based on electric power supplied (applied) to the light-emitting portions disposed near the first sensor unit and the second sensor unit. Thus, even in a case where the first sensor unit and the second sensor unit have a sensitivity characteristic that changes depending on the temperature, the temperature of the first sensor unit and the temperature of the second sensor unit approach an identical temperature by controlling electric power supplied to the first light source and electric power supplied to the second light source, thereby enabling accurate temperature compensation.

(8) To maximize advantages of the present invention, a temperature characteristic of the first sensor unit and a temperature characteristic of the second sensor unit need to be identical to each other. As a technique for minimizing a variation in temperature characteristic in a wafer plane and causing temperature characteristics of the first and second sensor units to approach each other as much as possible, in a fabrication process of a gas sensor, two chips (i.e., the first substrate and the second substrate) that are at adjacent locations in a wafer plane are picked up for mounting. At this time, from the viewpoint of easiness of assembly of a gas sensor, these substrates preferably have the same shape and layout. In this manner, as compared to the case of alternately mounting different substrates (e.g., two types of substrates, specifically a substrate including only a light-emitting portion and a substrate including only a sensor unit), the configuration described above is preferable in some cases because assembly can be easily performed.

That is, in the present embodiment, compensation for a signal variation in light emission and reception due to a change with time or temperature change of an application environment can be obtained, and even in a case where light emission characteristic of the light-emitting portion changes or in a case where sensitivity of the light-emitting element (the first sensor unit or the second sensor unit) changes depending on the temperature, the resulting gas sensor can more accurately detect a state of a space by using a sensor unit for state detection.

Application of Embodiment

As described above, the gas sensor according to the present embodiment is applicable to various types of equipment, and can be used as a gas sensor for detecting a concentration of a specific gas in a building or measurement equipment, a gas sensor to be mounted on mobile communication equipment such as a cellular phones or a smart phones, and a gas sensor for detecting a gas concentration in a transportation vehicle such as an automobile, an electric train, and an airplane.

For example, a $CO_2$ concentration is considered to be related to sleep of organisms. Suppose a target gas to be measured by the gas sensor of the present embodiment is $CO_2$, a $CO_2$ concentration can be accurately detected even in an environment where a peripheral temperature tends to change significantly. The gas sensor of the present embodiment is suitable for, for example, an anti-sleeping device (e.g., a device that generates an alarm or automatically provides ventilation when the $CO_2$ concentration reaches a predetermined level) used in driving of a vehicle.

The gas sensor of the present embodiment has a higher S/N ratio than that of a conventional gas sensor. Thus, even when the gas sensor of the present embodiment has a smaller size and a smaller thickness than those of the conventional gas sensor, the gas sensor of the present embodiment can show performance greater than or equal to that of the conventional gas sensor. Thus, the gas sensor of the present embodiment is applicable to, for example, small-size equipment (e.g., mobile communication equipment) to which a conventional gas sensor is difficult to be applied. In such an application, from the viewpoint of limitation of assembly space, specific device dimensions are designed in such a manner that width-to-length dimensions are preferably less than or equal to 20×20 $mm^2$, more preferably less than or equal to 15×15 $mm^2$, much more preferably less than or equal to 10×10 $mm^2$, and a height is preferably less than or equal to 10 mm, more preferably less than or equal to 5 mm, and much more preferably less than or equal to 3 mm. According to the present invention, a gas sensor having such dimensions is also enabled to have high sensitivity and high accuracy.

The configuration of the gas sensor according to the present embodiment is applicable to a light receiving and emitting device for applications as well as a gas sensor. That is, this specification also discloses examples of the invention derived by replacing all the "gas sensors" with "light receiving and emitting devices". For example, conditions (e.g., the presence and a concentration of a specific component in fluid, as an example except a gas) of an optical path space outside the substrates can be detected. For example, the configuration described above is applicable to, for example, a component detecting device or a component concentration measuring device for detecting or measuring a substance (e.g., water or body fluid) flowing in an optical path space between the first light source and the second sensor unit (between the first light source and the second sensor unit and between the second light source and the first sensor unit in the case of a 2-light source 2-sensor configuration). For example, the component detecting device or the component concentration measuring device can be used for, for example, measuring a glucose concentration in blood in a case where the substance flowing in the optical path space is blood.

For glucose detection in blood, a glucose concentration in blood glucose can be measured by measuring the absorption of light with a wavelength of 9.6 μm. That is, a small-size noninvasive glucose concentration measuring instrument with high accuracy and high reliability can be obtained. Such a glucose concentration measuring instrument enables a diabetic to examine a blood glucose level accurately without such skin damage as that occurs in an invasive technique, and medication (e.g., insulin) can be more correctly controlled.

SPECIFIC EXAMPLES OF EMBODIMENT

Then, specific examples (first to twenty-first embodiments) of the present embodiment will be described with reference to the drawings. In the drawing used in the following description, same reference numerals denote the same structures, and description thereof is not repeated.

First Embodiment

FIG. 1 is a conceptual illustration of an example configuration of a gas sensor according to a first embodiment of the present invention. As illustrated in FIG. 1, this gas sensor is a gas sensor including a gas cell 10 to which a detection target gas can be introduced, a first light source 20 that outputs light in an infrared range (i.e., infrared rays) including a wavelength that can be absorbed by the detection target gas, a first sensor unit 31 and a second sensor unit 32 disposed to receive light output from the first light source 20, a first substrate 41 having a first principal surface 411 on which the first light source 20 and the first sensor unit 31 are provided, and a second substrate 42 having a first principal surface 421 on which the second sensor unit 32 is provided.

In this gas sensor, the first sensor unit 31 is disposed at a location where light (indicated by broken lines) output from the first light source 20 and reflected on the second principal surface 412 opposite to the first principal surface 411 of the first substrate 41 strikes the first sensor unit 31. The first substrate 41 and the second substrate 42 are disposed in such a manner that the second principal surface 412 and the second principal surface 422 face each other in the gas cell 10, and the first light source 20 and the second sensor unit 32 are disposed to sandwich the space in the gas cell 10.

In the gas sensor according to the first embodiment, the first sensor unit 31 is disposed at a location where light output from the first light source 20 and reflected on the second principal surface 412 opposite to the first principal surface 411 of the first substrate 41 (indicated by broken lines) strikes the first sensor unit 31. In this manner, the gas sensor can have a simple configuration, a small size and high reliability and obtain constant compensation for a measurement error due to a change in emission intensity of the first light source 20, independently of an application environment.

Second Embodiment

Figure 2:
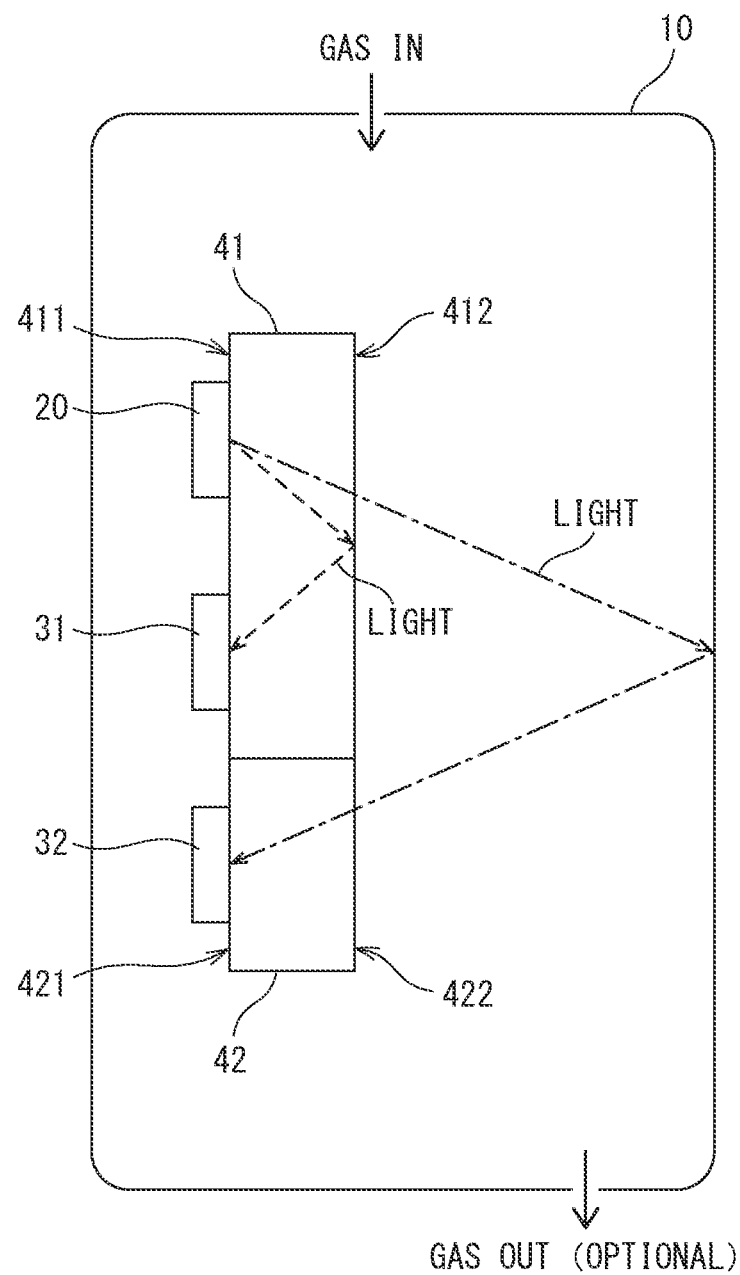
FIG. 2 is a view illustrative of an example configuration of a gas sensor according to a second embodiment of the present invention.

FIG. 2 is a conceptual illustration of an example configuration of a gas sensor according to a second embodiment of the present invention.

As illustrated in FIG. 2, in this gas sensor, a first substrate 41 and a second substrate 42 are disposed adjacent to each other with side surfaces (i.e., parts of peripheral side surfaces) thereof facing each other. Such a layout herein will be hereinafter referred to as a parallel layout. The second embodiment is different from the first embodiment in that the first substrate 41 and the second substrate 42 are disposed in a parallel layout. The other part of the configuration of the second embodiment is the same as that of the first embodiment. From the viewpoint of causing light emitted from the second principal surface of the first substrate to strike the second sensor unit efficiency, a part of an inner wall of a gas cell 10 is preferably covered with a material having a high reflectance especially in the second embodiment and the third, fifth, and sixth embodiments described later.

In the gas sensor of the second embodiment, the second substrate 42 and the first substrate 41 are disposed in a parallel layout so that the size of the gas sensor can be further reduced.

Third Embodiment

Figure 3:
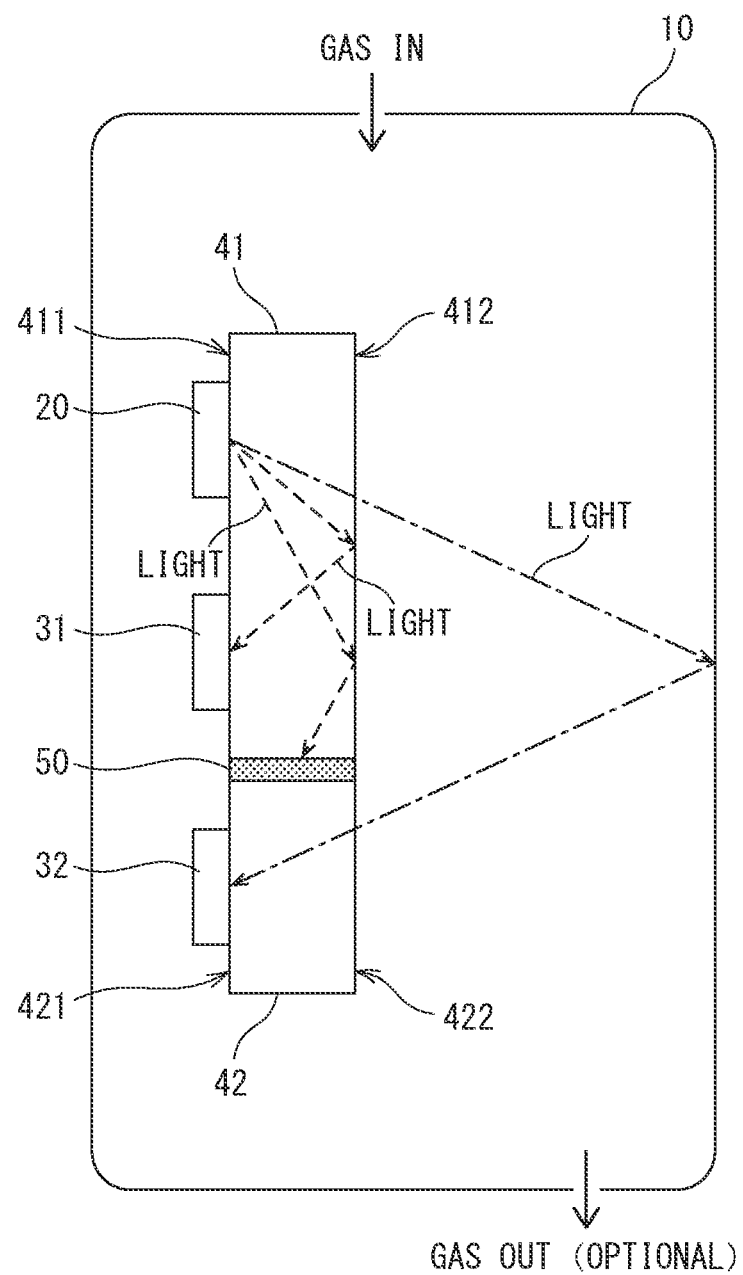
FIG. 3 is a view illustrative of an example configuration of a gas sensor according to a third embodiment of the present invention.

FIG. 3 is a conceptual illustration of an example configuration of a gas sensor according to a third embodiment of the present invention. As illustrated in FIG. 3, this gas sensor includes a light-blocking portion 50 provided between a first substrate 41 and a second substrate 42. The third embodiment is different from the second embodiment in including the light-blocking portion 50. The light-blocking portion 50 may be made of an encapsulating resin. The other part of the configuration of the third embodiment is the same as that of the second embodiment.

In the gas sensor of the third embodiment, the light-blocking portion 50 causes light in an infrared range (i.e., infrared rays) output from the first light source 20 and reflected on a second principal surface 412 of the first substrate 41 to reach a first sensor unit 31 but not to reach a second sensor unit 32. All the light that reaches the second sensor unit 32 is light that has passed through a space in a gas cell 10, and thus, a gas can be more accurately detected.

Fourth Embodiment

Figure 4:
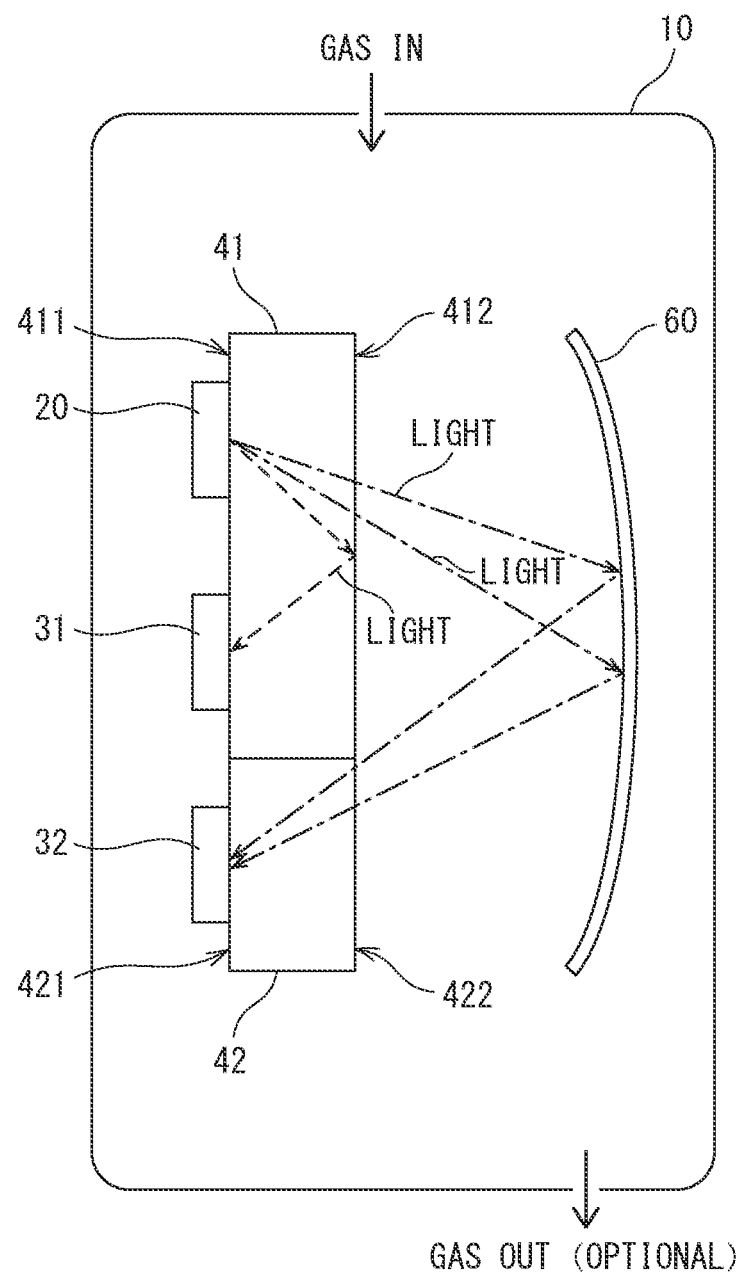
FIG. 4 is a view illustrative of an example configuration of a gas sensor according to a fourth embodiment of the present invention.

FIG. 4 is a conceptual illustration of an example configuration of a gas sensor according to a fourth embodiment of the present invention. As illustrated in FIG. 4, this gas sensor includes a light reflection unit 60 in a gas cell space facing a second principal surface 412 of a first substrate 41 and a second principal surface 422 of a second substrate 42. That is, this gas sensor includes the light reflection unit 60 that is disposed away from the first substrate 41 and the second substrate 42 in a gas cell 10 and reflects light emitted from the second principal surface 412 of the first substrate 41 toward a second sensor unit 32. The fourth embodiment is different from the second embodiment in including the light reflection unit 60. The other part of the configuration of the fourth embodiment is the same as that of the second embodiment.

The gas sensor of the fourth embodiment includes the light reflection unit 60 so that infrared rays (indicated by dot-and-dash lines) emitted from the second principal surface 412 of the first substrate 41 and included in light output from a first light source 20 are reflected on the light reflection unit 60 and selectively strike the second sensor unit 32. Thus, the gas sensor is enabled to have high sensitivity.

Fifth Embodiment

Figure 5:
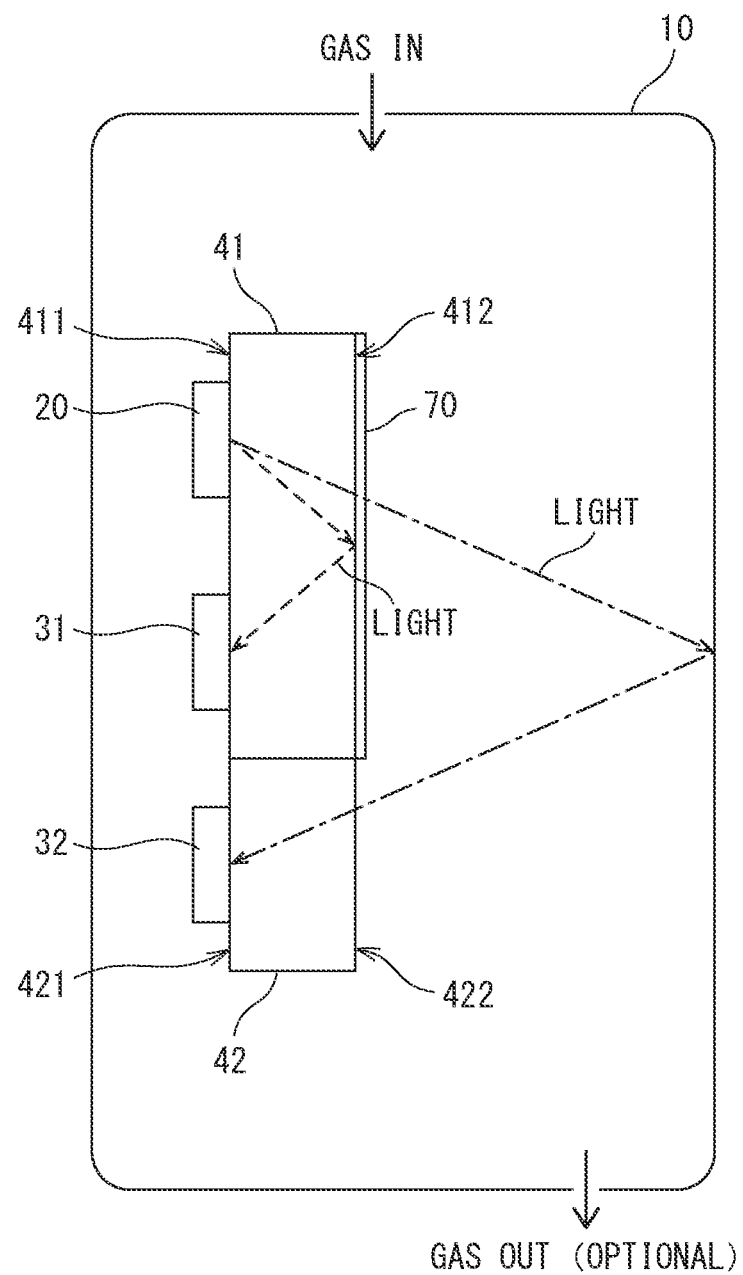
FIG. 5 is a view illustrative of an example configuration of a gas sensor according to a fifth embodiment of the present invention.

FIG. 5 is a conceptual illustration of an example configuration of a gas sensor according to a fifth embodiment of the present invention. As illustrated in FIG. 5, this gas sensor includes a control layer 70 that is disposed on a second principal surface 412 of a first substrate 41 and controls an amount of light (indicated by dotted lines) output from a first light source 20 and scattered in the first substrate 41 and an amount of a radiation angle of light (indicated by dot-and-dash lines) output from the first light source 20 and radiated from the second principal surface 412 of the first substrate 41 to a space in a gas cell 10. The fifth embodiment is different from the second embodiment in including the control layer 70. The other part of the configuration of the fifth embodiment is the same as that of the second embodiment.

The gas sensor of the fifth embodiment includes the control layer 70 so that a ratio between an amount of light desired to strike a first sensor unit 31 and an amount of light desired to strike a second sensor unit 32. Thus, a sensor having a high S/N ratio can be easily designed. The control layer 70 may be provided on a second principal surface of a second substrate 42.

Sixth Embodiment

Figure 6:
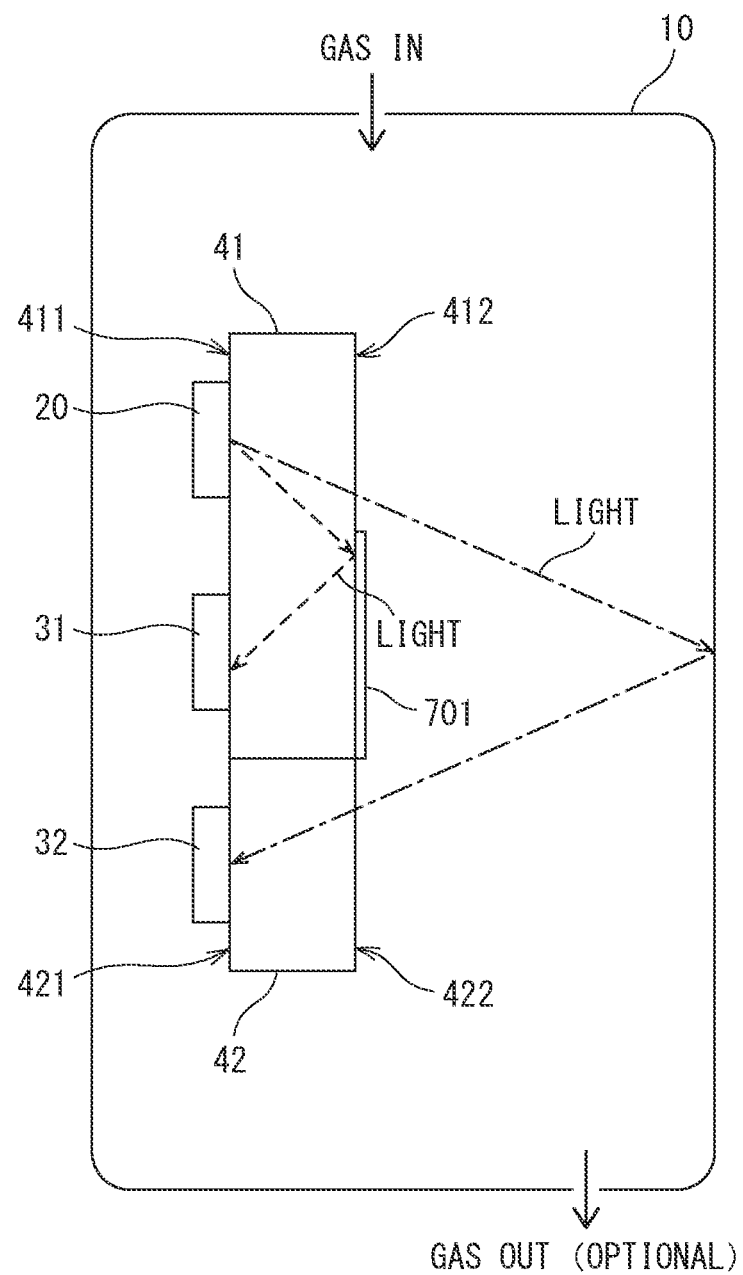
FIG. 6 is a view illustrative of an example configuration of a gas sensor according to a sixth embodiment of the present invention.

FIG. 6 is a conceptual illustration of an example configuration of a gas sensor according to a sixth embodiment of the present invention. As illustrated in FIG. 6, this gas sensor includes a light reflection layer 701 disposed on a second principal surface of a first substrate and reflects light output from a first light source toward a first sensor unit. A material for the light reflection layer 701 may be any material as long as the material reflects light, and a material showing a metallic luster and total internal reflection is more preferable. Specifically, from the viewpoint of high reflectance, a material including Al and/or Au is preferable in some cases. The sixth embodiment is different from the second embodiment in including the light reflection layer 701. The other part of the configuration of the sixth embodiment is the same as that of the second embodiment.

The gas sensor of the sixth embodiment includes the light reflection layer 701 so that an amount of light desired to strike a first sensor unit 31 can be enhanced. In this manner, a signal S/N ratio of the first sensor unit 31 can be enhanced. In some cases, the light-receiving surface area of the first sensor unit can be reduced with the S/N ratio being kept so that an efficiency in using a substrate can be enhanced.

Seventh Embodiment

Figure 7:
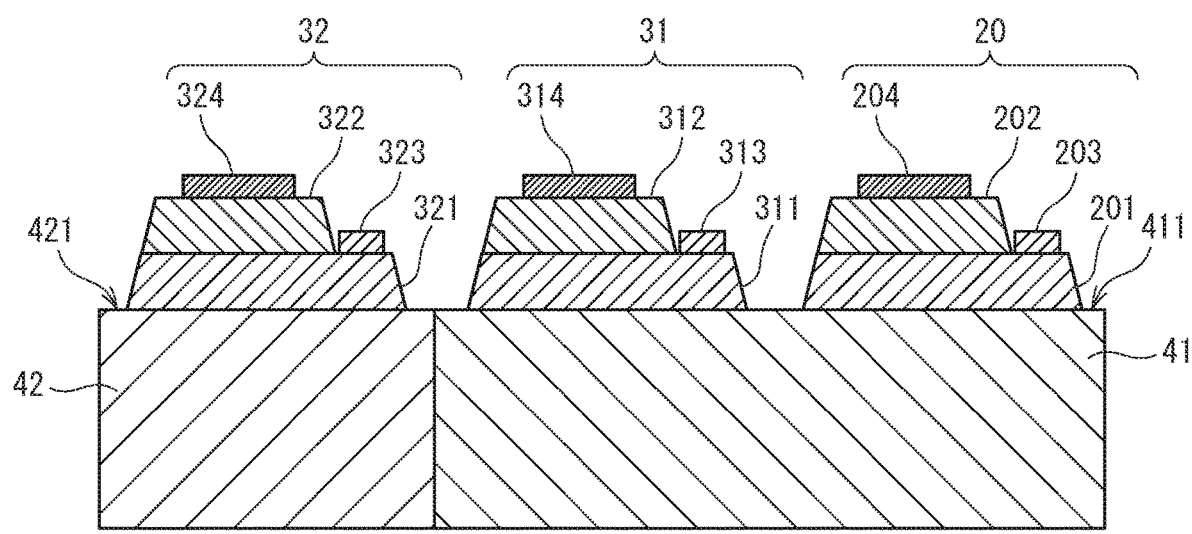
FIG. 7 is a view illustrative of an example configuration of a gas sensor according to a seventh embodiment of the present invention.

FIG. 7 is a sectional view illustrating an example configuration of a gas sensor according to a seventh embodiment of the present invention. In FIG. 7, reference numerals 201, 311, and 321 denote a semiconductor layer of a first conductivity type (e.g., an n-type semiconductor layer), reference numerals 202, 312, and 322 is a semiconductor layer of a second conductivity type (e.g., a p-type semiconductor layer), and reference numerals 203, 204, 313, 314, 323, and 324 denote electrodes.

As illustrated in FIG. 7, a first light source 20 includes, for example, the semiconductor layer 201 of the first conductivity type formed on a first principal surface 411 of a first substrate 41, the semiconductor layer 202 of the second conductivity type and the electrode 203 formed on the semiconductor layer 201, and the electrode 204 formed on the semiconductor layer 202.

A first sensor unit 31 includes, for example, the semiconductor layer 311 of the first conductivity type formed on the first principal surface 411 of the first substrate 41, the semiconductor layer 312 of the second conductivity type and the electrode 313 formed on the semiconductor layer 311, and the electrode 314 formed on the semiconductor layer 312.

A second sensor unit 32 includes, for example, the semiconductor layer 321 of the first conductivity type formed on a first principal surface 421 of a second substrate 42, the semiconductor layer 322 of the second conductivity type and the electrode 323 formed on the semiconductor layer 321, and the electrode 324 formed on the semiconductor layer 322.

Here, the semiconductor layers 201, 311, and 321 of the first conductivity type are made of an identical material and have an identical thickness, for example. The semiconductor layers 202, 312, and 322 of the second conductivity type are made of an identical material and have an identical thickness.

In FIG. 7, each of the first sensor unit 31 and the second sensor unit 32 is illustrated as one element. Alternatively, from the viewpoint of an S/N ratio, a plurality of elements may be electrically connected to each other so that the elements can serve as one sensor unit. From the viewpoint of light emission efficiency, a first light source 20 may be a plurality of elements that are electrically connected to each other. An intrinsic semiconductor layer (a so-called i-type semiconductor layer) may be inserted between the semiconductor layers 201, 311, and 321 of the first conductivity type and the semiconductor layers 202, 312, and 322 of the second conductivity type so that a PIN junction is formed.

The gas sensor of the seventh embodiment includes the semiconductor layers 201, 311, and 321 of the first conductivity type and the semiconductor layers 202, 312, and 322 of the second conductivity type made of identical or similar materials and having identical or similar thicknesses so that the first light source 20, the first sensor unit 31, and the second sensor unit 32 show an identical temperature characteristic. Thus, the gas sensor has high accuracy, independently of a change in the environmental temperature.

Eighth Embodiment

Figure 8:
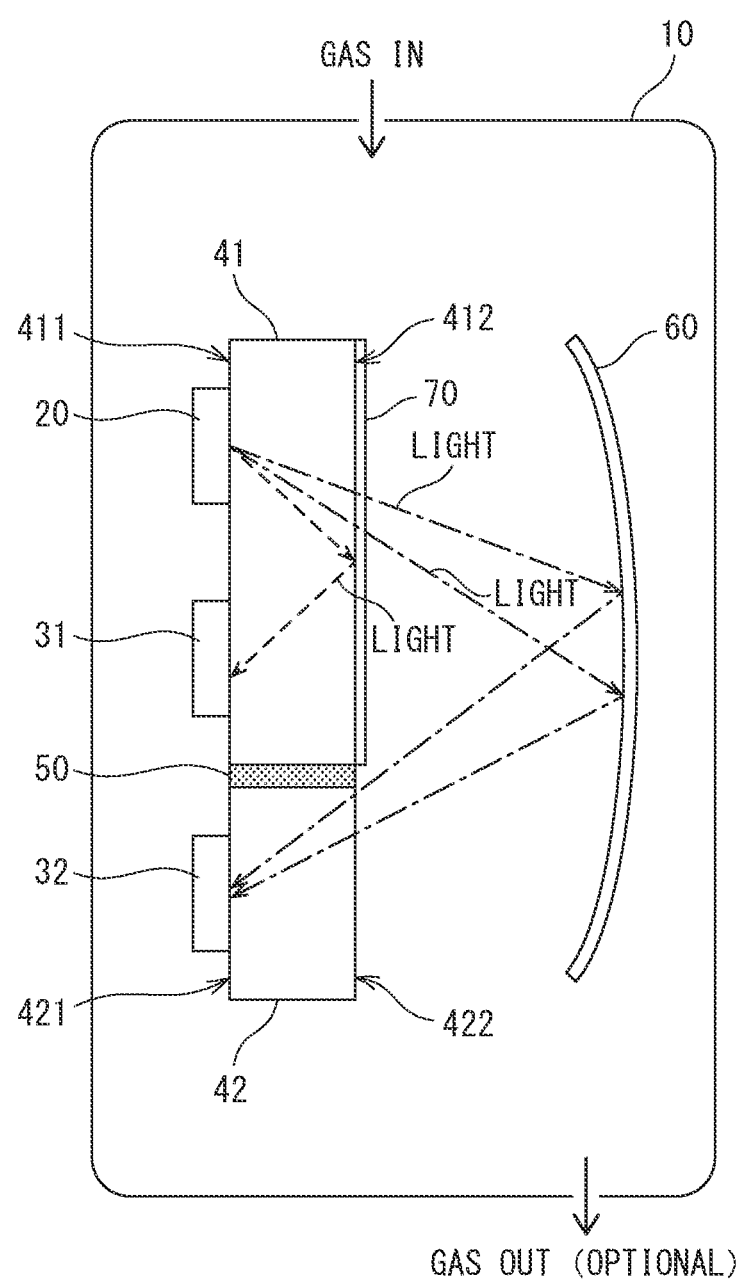
FIG. 8 is a view illustrative of an example configuration of a gas sensor according to an eighth embodiment of the present invention.

FIG. 8 is a conceptual illustration of an example configuration of a gas sensor according to an eighth embodiment of the present invention.

As illustrated in FIG. 8, this gas sensor has all the features of the third through sixth embodiments in addition to the features of the gas sensor of the second embodiment. The gas sensor of the eighth embodiment includes all the features of the second through sixth embodiments so that the gas sensor has a small size and shows highest degrees of accuracy and sensitivity. The light-blocking portion 50 illustrated in FIG. 8 substantially serves as the light-blocking portion described in the third embodiment (see FIG. 3).

Ninth Embodiment

Figure 9:
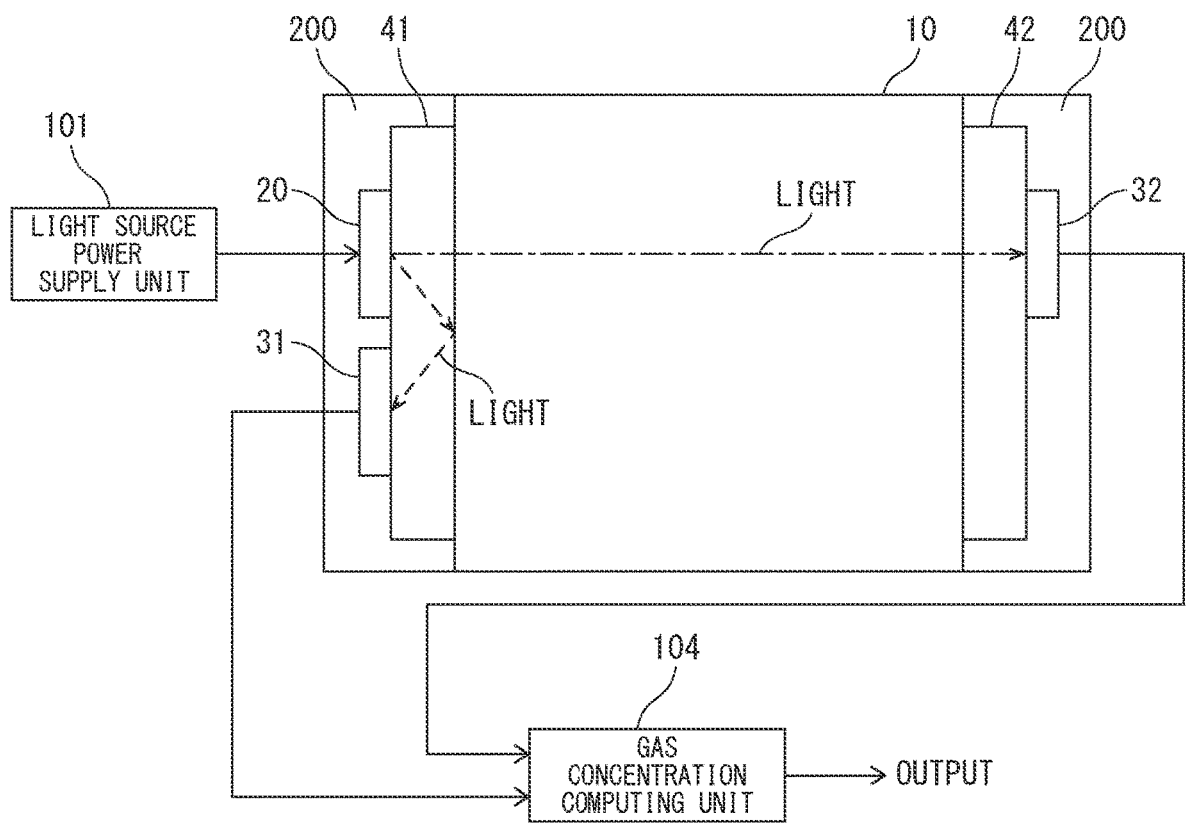
FIG. 9 is a view illustrative of an example configuration of a gas sensor according to a ninth embodiment of the present invention.

FIG. 9 is a conceptual illustration of an example configuration of a gas sensor according to a ninth embodiment of the present invention.

As illustrated in FIG. 9, in this gas sensor, each of the first substrate 41 and the second substrate 42 of the gas sensor of the first embodiment is encapsulated by an encapsulating resin 200, and a driving unit and a signal processing unit are connected to a first light source 20, a first sensor unit 31, and a second sensor unit 32.

Specifically, the gas sensor of the ninth embodiment includes a light source power supply unit 101 for supplying electric power to the first light source 20, and a gas concentration computing unit 104 that receives signals output from the first sensor unit 31 and the second sensor unit 32 and compute a gas concentration of a detection target gas. From the viewpoint of reducing power consumption, the light source power supply unit 101 preferably supplies a pulse signal (voltage or current) to the first light source 20.

In the gas sensor of the ninth embodiment, the driving unit and the signal processing unit are connected to the first light source 20, the first sensor unit 31, and the second sensor unit 32 so that a gas concentration of a detection target gas introduced into a gas cell 10 can be automatically calculated and a result of the calculation can be output.

Tenth Embodiment

Figure 10:
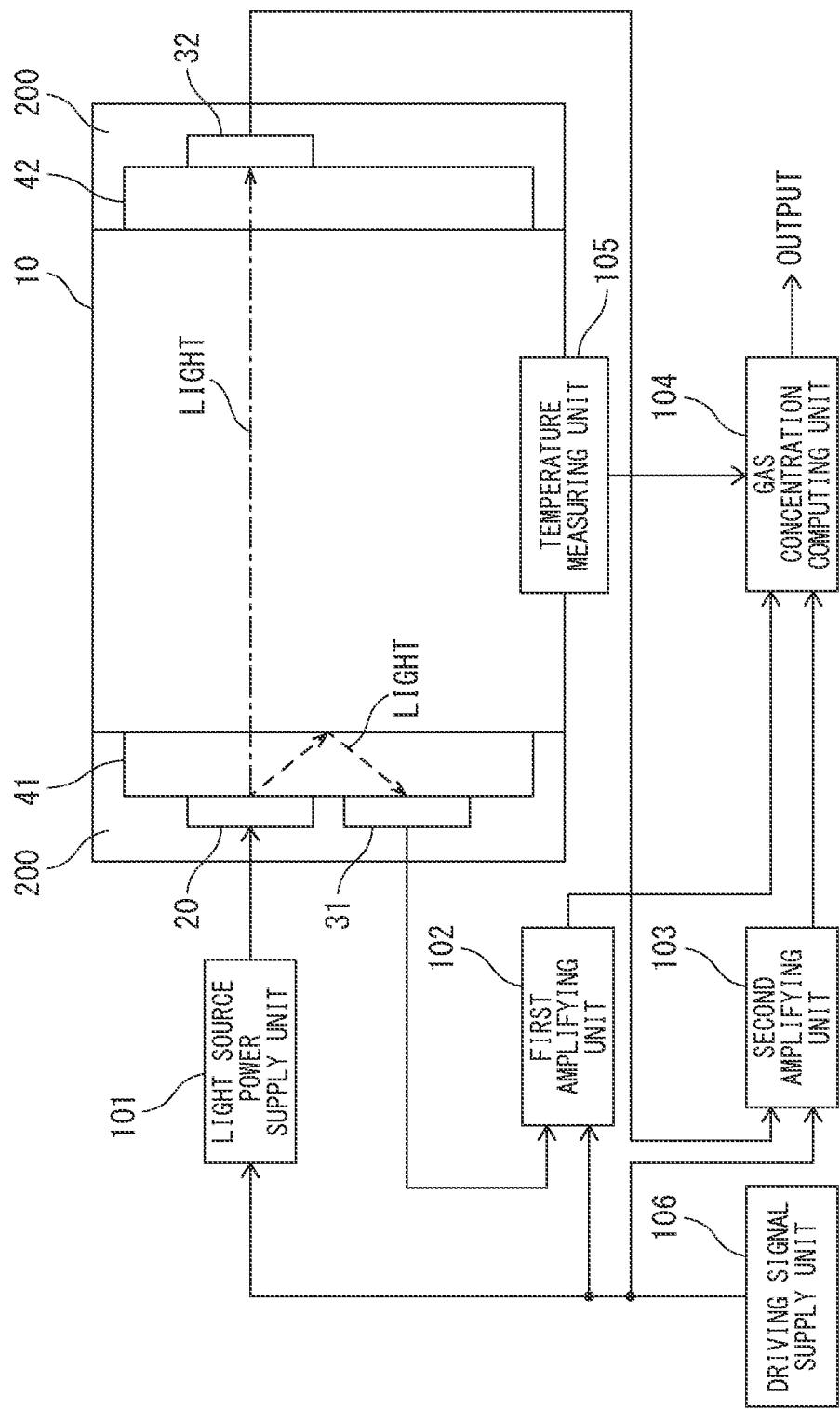
FIG. 10 is a view illustrative of an example configuration of a gas sensor according to a tenth embodiment of the present invention.

FIG. 10 is a conceptual illustration of an example configuration of a gas sensor according to a tenth embodiment of the present invention.

As illustrated in FIG. 10, this gas sensor further includes, in addition to the components of the gas sensor of the ninth embodiment, a first amplifying unit 102 for amplifying an output signal from a first sensor unit 31, a second amplifying unit 103 for amplifying an output signal from a second sensor unit 32, a temperature measuring unit 105 for measuring a temperature in a gas cell 10, and a driving signal supply unit 106 for supplying driving signals to the light source power supply unit 101, the first amplifying unit 102, and the second amplifying unit 103.

From the viewpoint of reducing power consumption, a signal supplied from the driving signal supply unit 106 is preferably a pulsed synchronizing signal for determining operation timings of the light source power supply unit 101, the first amplifying unit 102, and the second amplifying unit 103.

To compensate for a drift depending on an environmental temperature, the temperature measuring unit 105 for measuring a temperature around or in the gas cell 10 is preferably provided. An emission spectrum of the first light source 20 can change depending on an environmental temperature in some cases. For some types of a detection target gas, the amount of light absorption can change depending on an environmental temperature in some cases. In view of these circumstances, the temperature measuring unit 105 is preferably provided because temperature information obtained by the temperature measuring unit 105 can be supplied to the gas concentration computing unit 104 so that compensation for a shift depending on an environmental temperature can be obtained.

From the viewpoint of amplifying a signal with a high S/N ratio, each of the first amplifying unit 102 and the second amplifying unit 103 is preferably an amplifier (a so-called Lock-in Amp) having a phase shift detection (PSD) function. In the case of using the amplifier having a PSD function, an output signal from the driving signal supply unit 106 is preferably a pulsed synchronizing signal.

In the gas sensor of the tenth embodiment, the driving signal supply unit 106 supplies a pulsed synchronizing signal for determining operation timings to the light source power supply unit 101, the first amplifying unit 102, and the second amplifying unit 103, thereby enabling reduction of power consumption of the gas sensor. In addition, the temperature measuring unit 105 supplies temperature information to the gas concentration computing unit 104 so that a shift due to an environmental temperature can be compensated for.

Eleventh Embodiment

Figure 11:
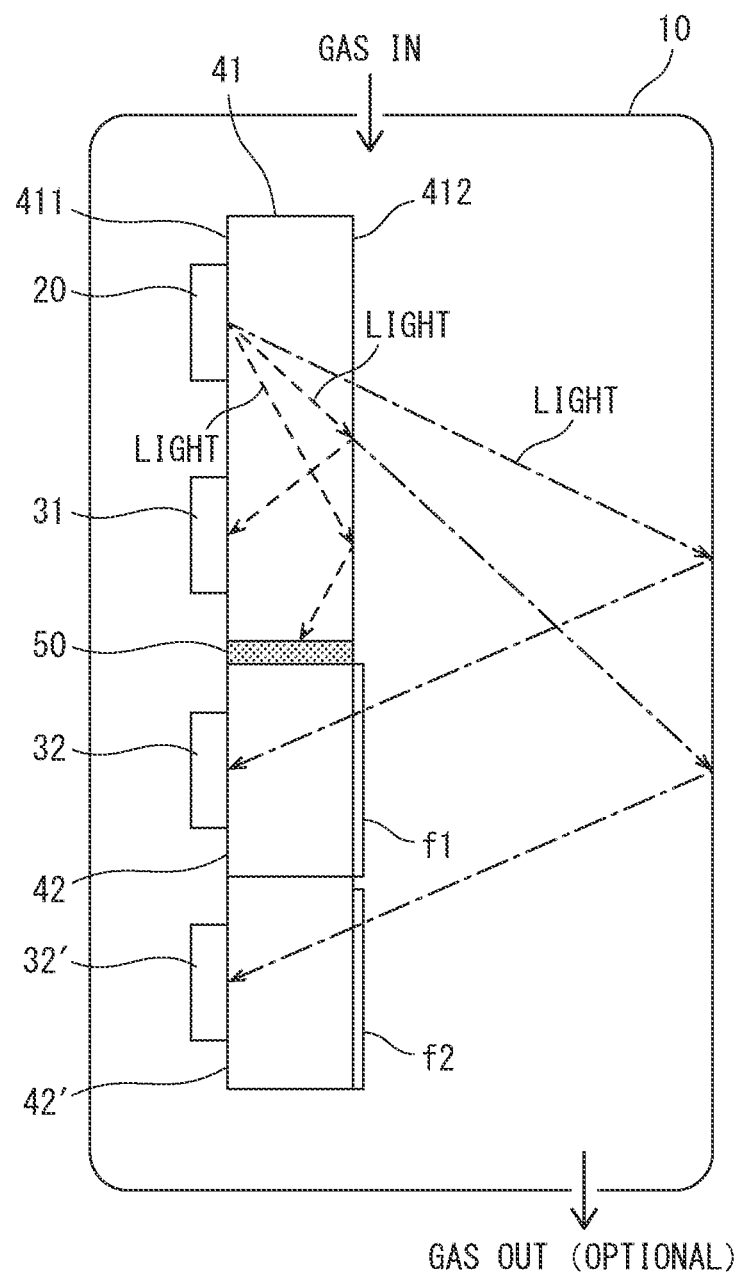
FIG. 11 is a view illustrative of an example configuration of a gas sensor according to an eleventh embodiment of the present invention.

FIG. 11 is a conceptual illustration of an example configuration of a gas sensor according to an eleventh embodiment of the present invention.

As illustrated in FIG. 11, this gas sensor includes a first substrate 41 and second substrates 42 and 42'. That is, the gas sensor includes two second substrates. Band-pass filters f1 and f2 transmissive to different wavelengths are provided on second principal surfaces (back surfaces) of the second substrates 42 and 42' so that two types of gases can be detected at the same time. Of course, three or more second substrates may be provided. The second substrates may be shared so that a large number of (two or more) light-receiving portions are provided on a first principal surface thereof and optical filters (e.g., band-pass filters) coaxial with the individual light-receiving portions are provided.

The gas sensor of the eleventh embodiment is especially advantageous in detecting a mixed gas. Specifically, in a case where a detection target gas introduced into a gas cell 10 is a mixed gas of a gas A and a gas B, suppose the gas A is absorbed at a wavelength 1, and the gas B is absorbed at a wavelength 2. This case uses a gas sensor having a configuration in which the second substrate 42 includes the band-pass filter f1 transmissive to light with the wavelength 1, and the second substrate 42' includes the band-pass filter f2 transmissive to light with the wavelength 2. Based on an intensity of an output signal from the second sensor unit 32 provided on the second substrate 42 and an intensity of an output signal from the second sensor unit 32' provided on the second substrate 42', a concentration of each gas can be obtained.

In the case where a detection target gas introduced into the gas cell 10 is a mixed gas of a gas A and a gas B, suppose the gas A is absorbed in the wavelength 1 and the wavelength 2 and the gas B is similarly absorbed in the wavelength 1 and the wavelength 2, but an absorption ratio differs between the gas A and the gas B. This case uses a gas sensor having a configuration in which the second substrate 42 includes the band-pass filter f1 transmissive to light with the wavelength 1 and the second substrate 42' includes the band-pass filter f2 transmissive to light with the wavelength 2. By determining an intensity of an output signal from the second sensor unit 32 provided on the second substrate 42, and an intensity of an output signal from the second sensor unit 32' provided on the second substrate 42', a mixture ratio between the gas A and the gas B in the detection target gas already introduced in the gas cell 10 can be determined.

[Gas Concentration Computation Method]

Next, a specific example of a gas concentration computation method using a gas sensor according to the present embodiment will be described. Suppose a signal output from the first sensor unit 31 is Ip1, and a signal output from the second sensor unit 32 is Ip2. Then, Ip1 and Ip2 can be expressed by Equation (3) and Equation (4):

$$Ip1 = RiREF(T) \times \varphi(T) \times \alpha \qquad (3)$$

$$Ip2 = RiGAS(T) \times \varphi(T) \times \beta \times (1-A(C)) \qquad (4)$$

where
A absorptance depending on gas concentration
C gas concentration
$\varphi$ emission intensity of first light source
$\alpha$ transmittance from first light source to first sensor unit
$\beta$ light-extraction efficiency from substrate (or transmittance from first light source to second sensor unit in a case where a detection target substance (e.g., a gas) shows no absorption)
Ip1 signal output from first sensor unit
Ip2 signal output from second sensor unit
RiREF sensitivity of first sensor unit
RiGAS sensitivity of second sensor unit An example of a computation method in the gas concentration computing unit 104 illustrated in FIG. 9 or FIG. 10 is expressed by Equation (5):

$$\text{Computation result} = Ip2/Ip1 \qquad (5)$$
$$= (RiGAS(T) \times \beta \times (1-A(C)))/(RiREF(T) \times \alpha)$$

Here, with respect to a temperature characteristic of the first light source, the temperature characteristics may differ between the sensors. However, if a temperature characteristic g1(T) of the first sensor unit is equal to, or in proportion to, a temperature characteristic g2(T) of the second sensor unit, $Ip2/Ip1 \propto (1-A(C))$ is established, and temperature dependency of the gas sensor can be eliminated. As a result, an intrinsic absorbance due to gas molecules absorbance can be obtained. From the Lambert-Beer law, a gas concentration C can be extracted from (1−A(C)).

The above description is based on the assumption that $\alpha$ and $\beta$ do not change depending on wavelength and temperature. However, even if the $\alpha$ and $\beta$ change, a temperature of an LED and/or the first sensor unit is measured, and this measurement result may be used for temperature compensation. Basically, a resolution of a gas sensor can be expressed by Equation (6):

$$\text{Resolution} = (\Delta C/\Delta Ip)/(\text{SNR}) \qquad (6)$$

where $\Delta Ip$ is a signal change of a sensor, $\Delta C$ is a concentration change of a detection target gas, and SNR is an S/N ratio of a sensor unit obtained when the first light source is turned on or off (pulsed driving).

[Compensation for Change with Time]

As shown in Equation (5), the amount of the first light source is not indicated in the computation result, and thus, even when the first light source is degraded, that is, the light emission efficiency changes, the gas concentration computation result does not change. In the gas sensor of the present embodiment, the first light source 20 and the first sensor unit 31 are formed on the same substrate (the first substrate 41), and a signal based only on light emitted from the first light source 20 can be output. Thus, the amount of light emitted from the first light source 20 can be correctly measured. In a case where the first light source is constituted by a large number of light-emitting portions, arrangement of light-receiving portions of the first light source 20 and light-receiving portions of the first sensor unit 31 is appropriately designed so as to enable measurement of quantities of light emitted from the light-emitting portions.

An offset due to a disturbance or a circuit can be removed by continuously turning the first light source on and off (pulsed driving), reading signals from the first sensor unit and the second sensor unit when the first light source is on and signals from the first sensor unit and the second sensor unit when the first light source is off, and utilizing a signal difference thereof. This is because an offset due to a circuit or a disturbance always occurs irrespective of on/off of the first light source, and thus, the offset component can be removed by taking a signal difference between the on state and the off state.

Advantages obtained by removing an offset are more significant in a case where a switching frequency between on and off is set at a sufficiently large value with respect to radiation of a disturbance and frequencies of fluctuations of a circuit offset. Specifically, in a case where a variable frequency band of the disturbance and the offset is 0 to 1 kHz, the on/off switching frequency is set at a level about 10 times (10 kHz) as high as the variable frequency band. In general, a power spectrum of this offset is inversely proportional to a frequency f, and calculated as 1/f (so called pink noise, 1/f noise). Thus, the switching frequency between on and off states is set in a frequency band in which 1/f noise does not appear. In addition to the signal modulation technique between the on and off state described above, amplitude modulation (AM) typically used in a communication system may be used.

As lower the resolution described above, the lower the gas concentration that can be measured (to about several tens parts per million (ppm) in the case of $CO_2$). From the relationship described above, the amount of an absorbed gas and the S/N ratio of a sensor have a trade-off relationship. Thus, in a case where an output of a light amount is obtained from the first light source, an optimum gas path length for obtaining this light amount needs to be designed.

If the first light source is driven with a low current and the gas cell is designed to have an excessive length in order to reduce power consumption of the entire gas sensor, a sufficient S/N ratio cannot be obtained in some cases. That is, although a short gas path is needed, as the gas path becomes shorter, a change in signal in accordance with temperature becomes more significant rather than a change in signal in accordance with a change in gas concentration. In such case, an effective temperature compensation technique is inevitable.

The first sensor unit and the second sensor unit are preferably quantum sensors because such quantum sensors can operate at high speed (are responsive to a high-speed optical pulse). In a quantum sensor, since an internal resistance of a sensor changes in accordance with temperature, an internal temperature of the gas sensor can be determined by reading an internal resistance value of this sensor. The use of this technique eliminates the need for additionally providing the temperature measuring unit 105, and thus, the resulting gas sensor can perform temperature compensation with a small number of components.

Twelfth Embodiment

Figure 12:
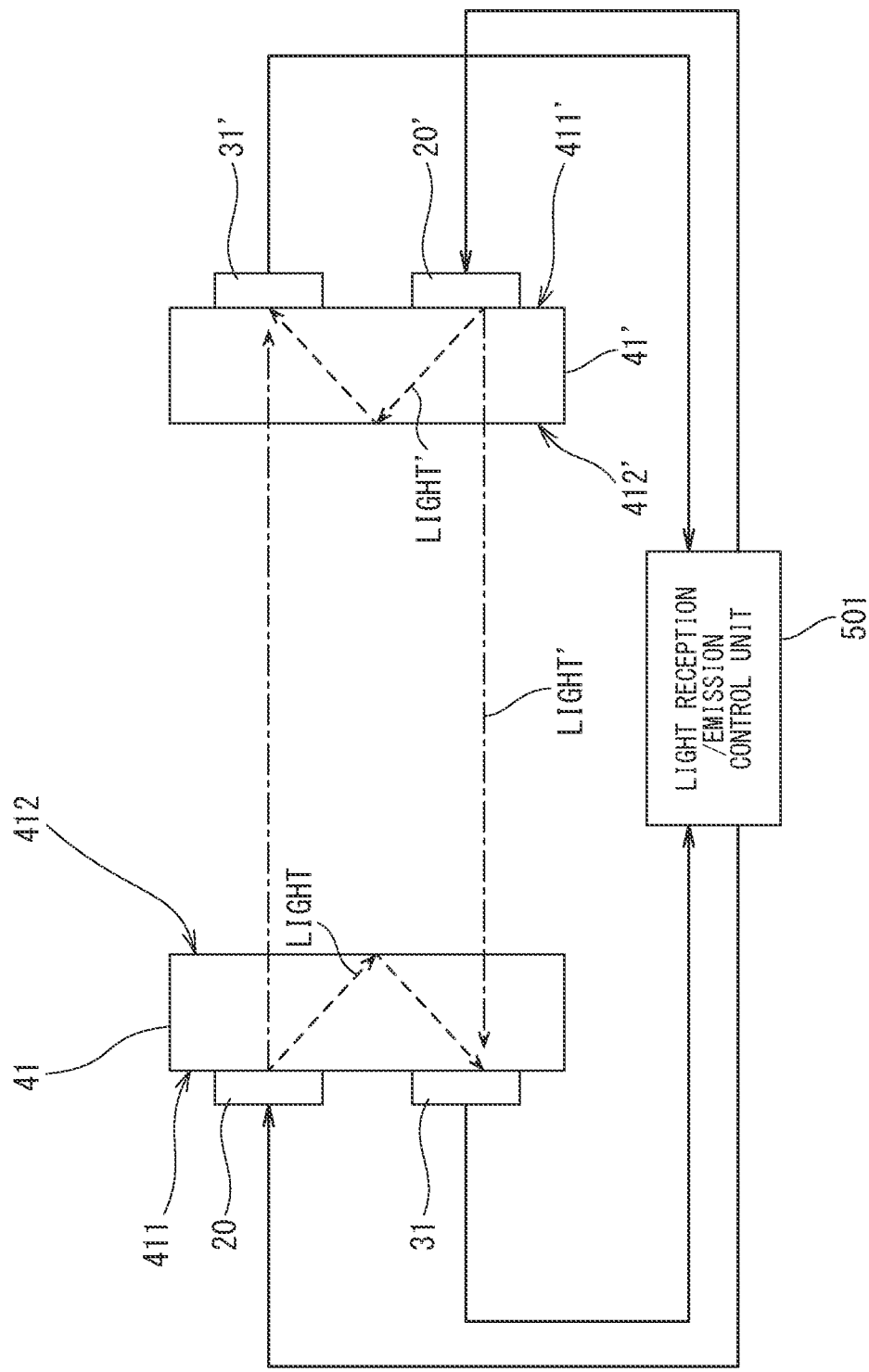
FIG. 12 is a view illustrative of an example configuration of a gas sensor according to a twelfth embodiment of the present invention.

FIG. 12 is a conceptual illustration of an example configuration of a gas sensor according to a twelfth embodiment of the present invention. As illustrated in FIG. 12, this gas sensor includes a first substrate 41 having a first principal surface 411 on which a first light source 20 and a first sensor unit 31 are provided, and a second substrate 41' having a first principal surface 411' on which a first light source 20' and a first sensor unit 31' are provided. The first substrate 41 and the second substrate 42 have an identical structure.

Light output from the first light source 20 and reflected on the second principal surface 412 opposite to the first principal surface 411 of the first substrate 41 (indicated by broken lines) strikes the first sensor unit 31, and light emitted from the second principal surface 412 of the first substrate 41 (indicated by chain lines) strikes the second principal surface 412' of the second substrate 41' and then strikes the second sensor unit 31' through the inside of the second substrate 41'. Light output from the second light source 20' and reflected on the second principal surface 412' opposite to the first principal surface 411' of the second substrate 41' (indicated by broken lines) strikes the second sensor unit 31', and light emitted from the second principal surface 412' of the second substrate 41' strikes the second principal surface 412 of the first substrate 41, and then strikes the first sensor unit 31 through the inside of the first substrate 41. To satisfy such conditions, the first substrate 41 and the second substrate 41' are disposed with the second principal surfaces 412 and 412' facing each other.

That is, the first sensor unit 31 is disposed at a location where light output from the first light source 20 and reflected on the second principal surface 412 of the first substrate 41 strikes the first sensor unit 31. The second sensor unit 31' is disposed at a location where light output from the second light source 20' and reflected on the second principal surface 412' of the second substrate 41' (not shown) strikes the second sensor unit 31'.

The gas sensor according to the twelfth embodiment includes a light reception/emission control unit 501. The light reception/emission control unit 501 supplies electric power to the first light source 20 and the second light source 20', and detects signals output from the first sensor unit 31 and the second sensor unit 31'. The light reception/emission control unit 501 supplies a desired level of electric power to each of the first light source 20 and the second light source 20' in such a manner that a temperature of the first sensor unit 31 disposed near the first light source 20 and a temperature of the second sensor unit 31' disposed near the second light source 20' are equal to each other.

In a case where the temperatures of the first sensor unit 31 and the temperature of the second sensor unit 31' are equal to each other, even when the sensitivities of the first sensor unit 31 and the second sensor unit 31' have temperature dependency, accurate temperature compensation can be obtained. In this manner, the gas sensor can have a simple configuration, small size, and high reliability and obtain constant compensation for a measurement error due to a change in emission intensity of the first light source 20 and a measurement error due to a change in emission intensity of the second light source 20, independently of an operation environment.

Thirteenth Embodiment

Figure 13:
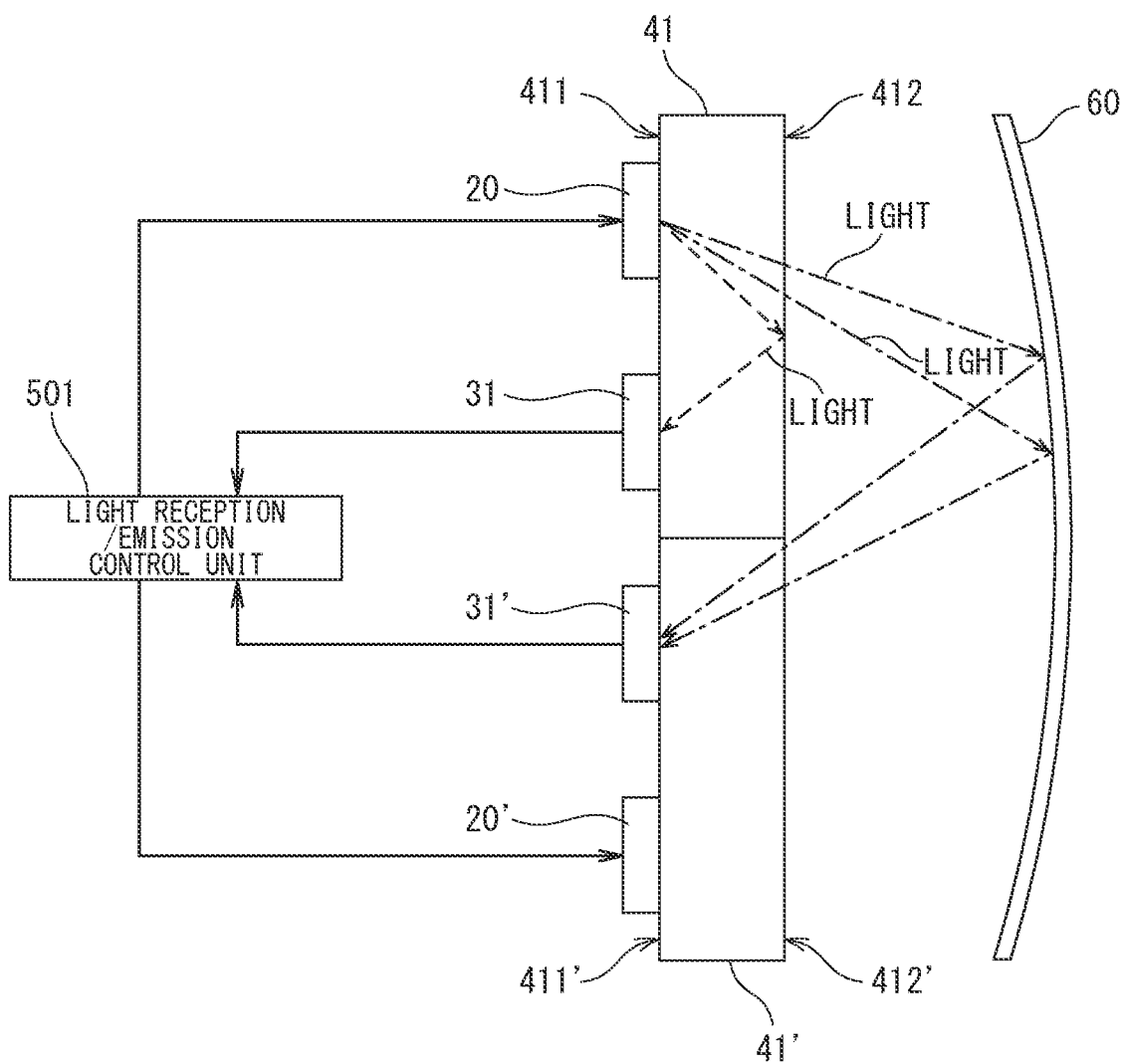
FIG. 13 is a view illustrative of an example configuration of a gas sensor according to a thirteenth embodiment of the present invention.

FIG. 13 is a conceptual illustration of an example configuration of a gas sensor according to a thirteenth embodiment of the present invention. As illustrated in FIG. 13, in this gas sensor, a first substrate 41 and a second substrate 41' are disposed adjacent to each other with their side surfaces (i.e., parts of peripheral side surfaces) thereof facing each other. Such a layout herein will be hereinafter referred to as a parallel layout. The thirteenth embodiment is different from the twelfth embodiment in that the first substrate 41 and the second substrate 41' are disposed in a parallel layout.

This gas sensor includes a light reflection unit 60 in a space facing a second principal surface 412 of the first substrate 41 and a second principal surface 412' of the second substrate 41'. That is, the gas sensor includes the light reflection unit 60 that is disposed away from the first substrate 41 and the second substrate 41' and reflects light emitted from the second principal surface 412 of the first substrate 41 toward a second sensor unit 31' and also reflects light emitted from the second principal surface 412' of the second substrate 41' toward a first sensor unit 31.

In this manner, the thirteenth embodiment is different from the twelfth embodiment in that the first substrate 41 and the second substrate 41' are disposed in a parallel layout and the light reflection unit 60 is provided. The other part of the configuration of the thirteenth embodiment is the same as that of the twelfth embodiment.

In the gas sensor of the thirteenth embodiment, the first substrate 41 and the second substrate 41' are disposed in a parallel layout so that the size of the gas sensor can be further reduced. The light reflection unit 60 enables light output from the first light source 20 and emitted from the second principal surface 412 of the first substrate 41 (indicated by dot-and-dash lines) to be reflected on the light reflection unit 60 and to selectively strike the second sensor unit 31'. The light reflection unit 60 also enables light output from the second light source 20' and emitted from the second principal surface 412' of the second substrate 41' (not shown) to be reflected on the light reflection unit 60 and to selectively strike the first sensor unit 31. Thus, the resulting gas sensor can have higher sensitivity.

Figure 14:
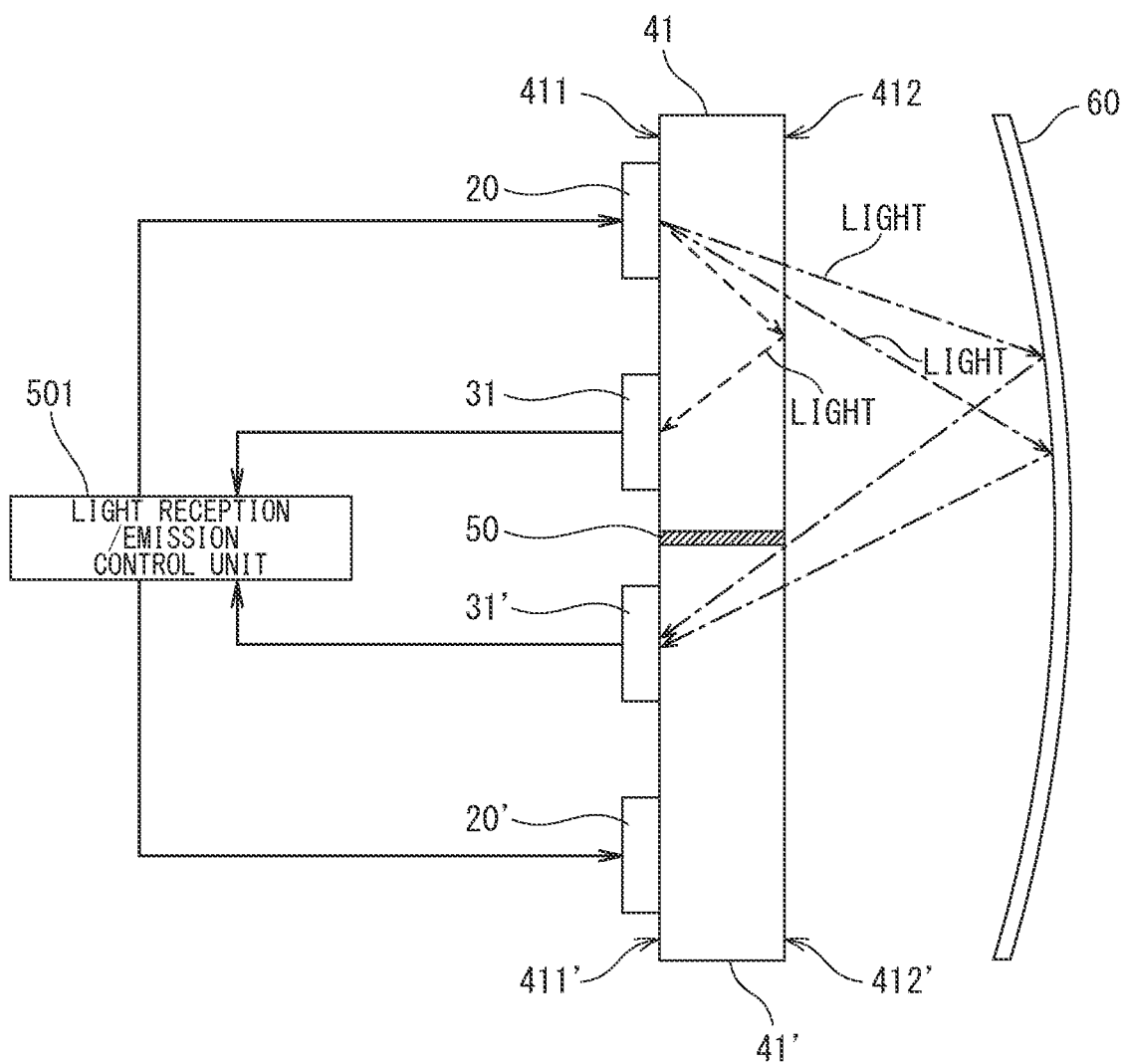
FIG. 14 is a view illustrative of an example configuration in which a light-blocking portion is provided in the thirteenth embodiment.

As illustrated in FIG. 14, in the thirteenth embodiment, a light-blocking portion 50 may be provided between the first substrate 41 and the second substrate 41'. The light-blocking portion 50 is preferably provided in some cases because the light-blocking portion 50 can prevent light emitted from the first light source 20 from striking the second sensor unit 31' through a side surface of the second substrate 41' and also prevent light emitted from the second light source 20' from striking the first sensor unit 31 through a side surface of the first substrate 41. The light-blocking portion 50 may be a part of a resin mold used for encapsulating the first substrate 41 and the second substrate 41'.

Fourteenth Embodiment

Figure 15:
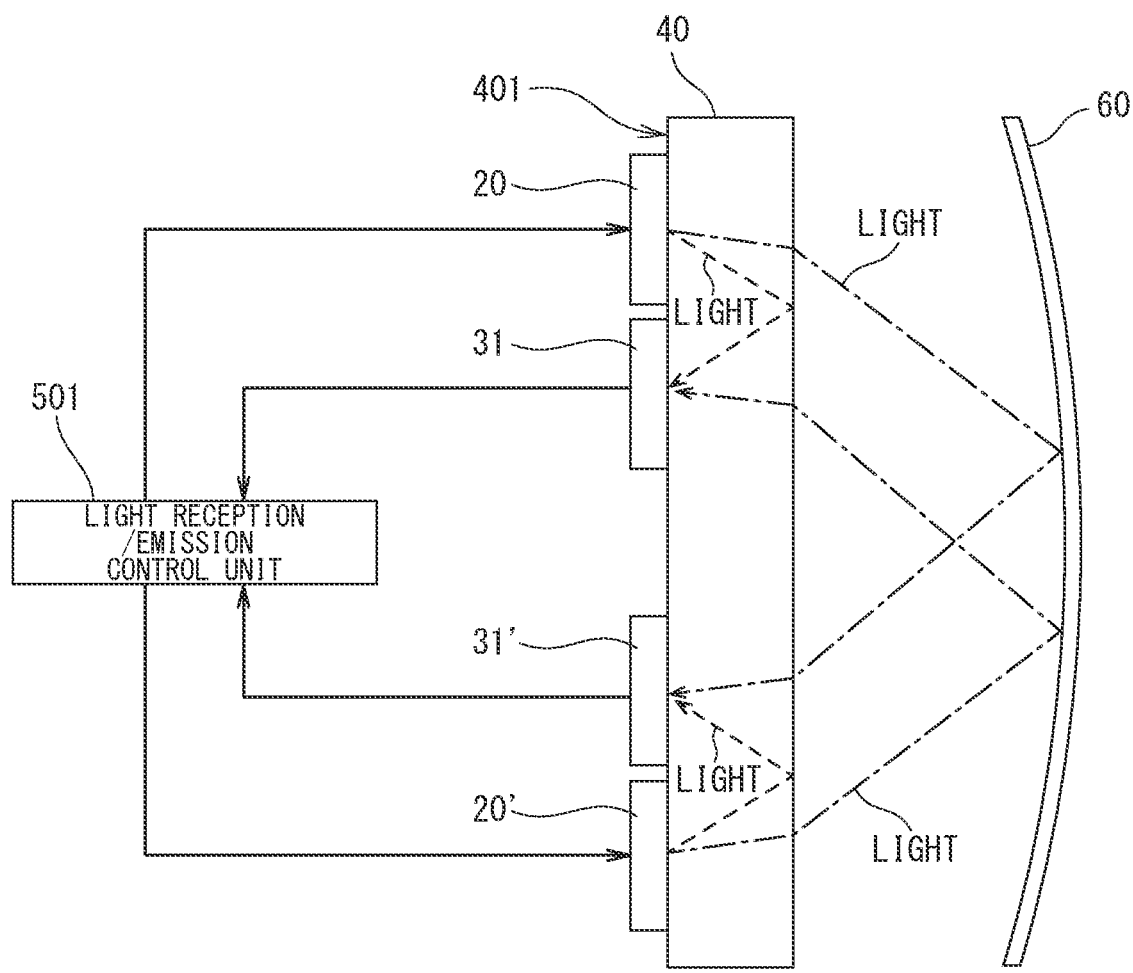
FIG. 15 is a view illustrative of an example configuration of a gas sensor according to a fourteenth embodiment of the present invention.

FIG. 15 is a sectional view illustrating an example configuration of a gas sensor according to a fourteenth embodiment of the present invention. Unlike the thirteenth embodiment, only one common substrate is used in the fourteenth embodiment. Specifically, the gas sensor of the fourteenth embodiment includes a common substrate 40 obtained by integrating the first substrate and the second substrate described above. The substrate 40 has a first surface 401 on which a first light source 20, a first sensor unit 31, a second light source 20', and a second sensor unit 31' are provided. The gas sensor of the fourteenth embodiment is advantageous in a case where reflected light from the first light source 20 to the second sensor unit 31' and reflected light from the second light source 20' to the first sensor unit 31 can be sufficiently attenuated. The gas sensor of the fourteenth embodiment is preferable in some cases because the number of components is smaller than those of the first and thirteenth embodiments.

Fifteenth Embodiment

Figure 16:
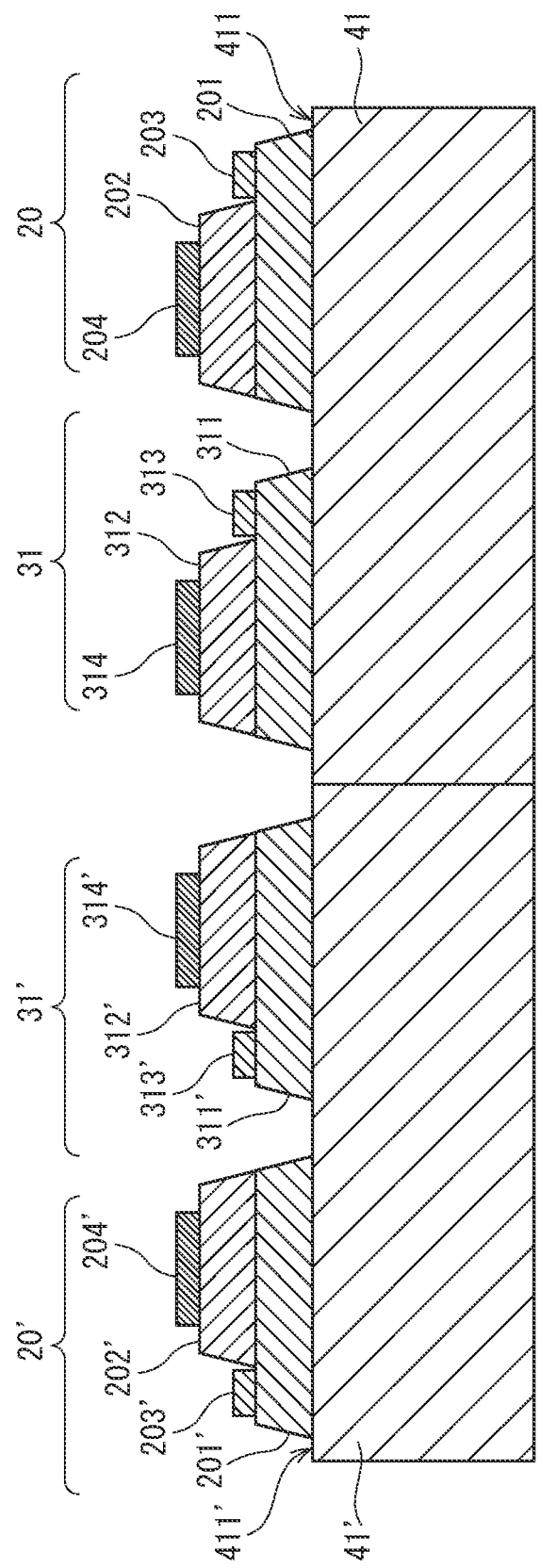
FIG. 16 is a view illustrative of an example configuration of a gas sensor according to a fifteenth embodiment of the present invention.

FIG. 16 is a sectional view illustrating an example configuration of a gas sensor according to a fifteenth embodiment of the present invention.

As illustrated in FIG. 16, a first light source 20 includes, for example, a semiconductor layer 201 of a first conductivity type (e.g., n-type) formed on a first principal surface 411 of a first substrate 41, a semiconductor layer 202 of a second conductivity type (e.g., p-type) and an electrode 203 formed on the semiconductor layer 201, and an electrode 204 formed on the semiconductor layer 202. The second light source 20' includes, for example, a semiconductor layer 201' of the first conductivity type formed on the first principal surface 411' of the second substrate 41', a semiconductor layer 202' of a second conductivity type and an electrode 203' formed on a semiconductor layer 201', and an electrode 204' formed on the semiconductor layer 202'.

A first sensor unit 31 includes, for example, a semiconductor layer 311 of the first conductivity type formed on the first principal surface 411 of the first substrate 41, a semiconductor layer 312 of the second conductivity type and an electrode 313 formed on a semiconductor layer 311, and an electrode 314 formed on the semiconductor layer 312. A second sensor unit 31' includes, for example, a semiconductor layer 311' of the first conductivity type formed on the first principal surface 411' of the second substrate 41', a semiconductor layer 312' of the second conductivity type and an electrode 313' formed on the semiconductor layer 311', and an electrode 314' formed on the semiconductor layer 312'.

Here, the semiconductor layers 201, 311, 201', and 311' of the first conductivity type are made of an identical material and have an identical thickness, for example. The semiconductor layers 202, 312, 202', and 312' of the second conductivity type are made of an identical material and have an identical thickness, for example. That is, the first light source 20, the second light source 20', the first sensor unit 31, and the second sensor unit 31' include a compound semiconductor having an identical film composition (i.e., compound semiconductor laminated portions having an identical composition). As illustrated in FIG. 16, the first light source 20 and the second light source 20' have an identical structure (i.e., have an identical shape and size). The first sensor unit 31 and the second sensor unit 31' also have an identical structure.

In FIG. 16, each of the first sensor unit 31 and the second sensor unit 31' is illustrated as one element. Alternatively, from the viewpoint of an S/N ratio, plurality of light-receiving elements may be electrically connected to each other so that the elements can serve as one sensor unit. From the viewpoint of light emission efficiency, the first light source 20 and the second light source 20' may be one light-emitting portion by electrically connecting a plurality of light-emitting elements. An intrinsic semiconductor layer (a so-called i-type semiconductor layer) may be inserted between the semiconductor layers 201, 311, 201', and 311' of the first conductivity type and the semiconductor layers 202, 312, 202', and 312' of the second conductivity type so that a PIN junction is formed.

The gas sensor of the fifteenth embodiment includes the semiconductor layers 201, 311, 201', and 311' of the first conductivity type made of identical or similar materials and having identical or similar thicknesses and the semiconductor layer 202, 312, 202', and 312' of the second conductivity type made of identical or similar materials and having identical or similar thicknesses so that the first light source 20, the second light source 20', the first sensor unit 31, and the second sensor unit 31' show an identical temperature characteristic. Thus, the gas sensor has high accuracy, independently of a change in an environmental temperature.

Since the first light source 20, the second light source 20', the first sensor unit 31, and the second sensor unit 31' show an identical temperature characteristic, the first light source 20 and the second light source 20' can generate heat at an identical temperature by supplying an identical level of electric power to the first light source 20 and the second light source 20'. In this manner, the first sensor unit 31 and the second sensor unit 31' can be made at an identical temperature.

Sixteenth Embodiment

Figure 17:
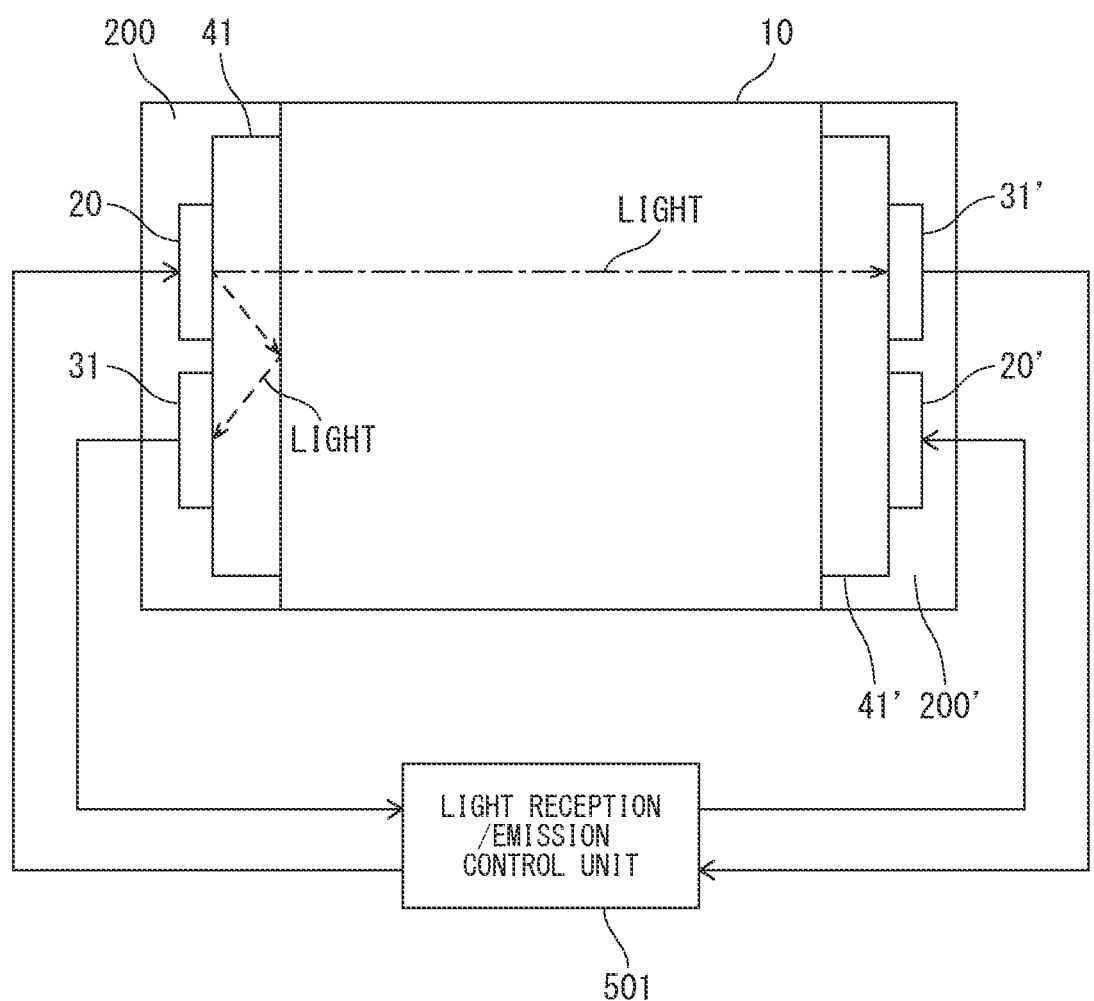
FIG. 17 is a view illustrative of an example configuration of a gas sensor according to a sixteenth embodiment of the present invention.

FIG. 17 is a conceptual illustration of an example configuration of a gas sensor according to a sixteenth embodiment of the present invention.

As illustrated in FIG. 17, this gas sensor is an example in which the first substrate 41 and the second substrate 41' of the gas sensor of the twelfth embodiment are respectively encapsulated by an encapsulating resin 200 and an encapsulating resin 200' and a light reception/emission control unit 501 is connected to a first light source 20, a first sensor unit 31, a second light source 20', and a second sensor unit 31'.

The gas sensor of the sixteenth embodiment may include a gas cell 10 which surrounds a space between the first substrate 41 and the second substrate 41' and in which a detection target substance (e.g., gas) can be introduced into the space. Although not shown, the gas cell 10 has an inlet for introducing a detection target substance therethrough.

In the gas sensor of the sixteenth embodiment, the first substrate 41 and the second substrate 41' are disposed with second principal surfaces 412 and 412' thereof facing each other. Thus, light output from the first light source 20 and emitted from the second principal surface 412 of the first substrate 41 passes through the space in the gas cell 10, strikes the second principal surface 412' of the second substrate 41', and strikes the second sensor unit 31' through the second substrate 41'. Light output from the second light source 20' and emitted from the second principal surface 412' of the second substrate 41' passes through the space in the gas cell 10, strikes the second principal surface 412 of the first substrate 41, and strikes the first sensor unit 31 through the first substrate 41. That is, a space (optical path space) serving as an optical path is present in the gas cell 10.

Figure 18:
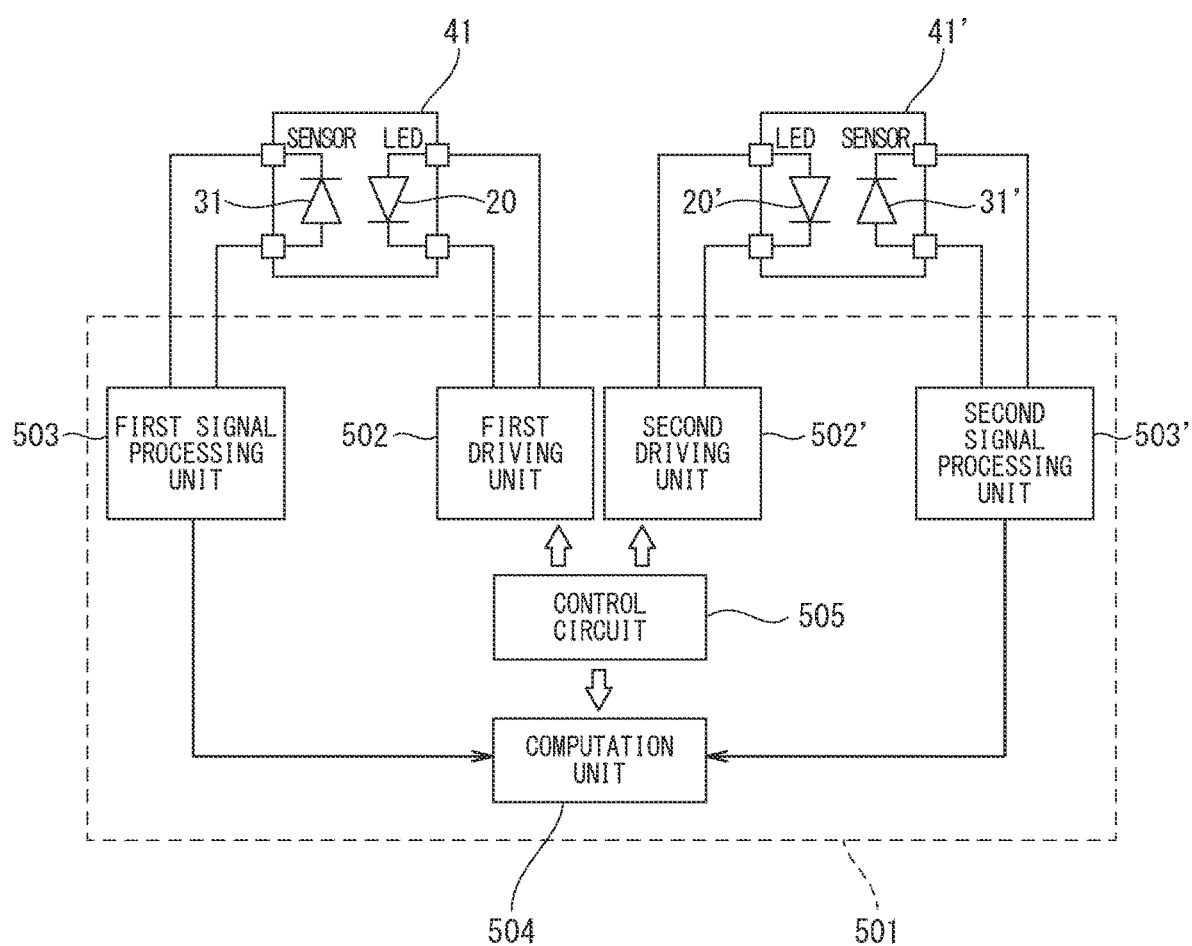
FIG. 18 is a view illustrative of an example of a circuit configuration in the sixteenth embodiment.

FIG. 18 illustrates an example of a circuit configuration in the sixteenth embodiment. FIG. 18 illustrates a more specific example configuration of the light reception/emission control unit 501, and a circuit configuration in a case where the first sensor unit 31 and the second sensor unit 31' are photodiodes, and the first light source 20 and the second light source 20' are LEDs.

As illustrated in FIG. 18, the light reception/emission control unit 501 includes, for example, a first driving unit 502 that supplies electric power to the first light source 20 and drives the first light source 20 (i.e., causes the first light source 20 to emit light), a second driving unit 502' that supplies electric power to the second light source 20' and drives the second light source 20', a first signal processing unit 503 that performs processing on a signal from the first sensor unit 31, a second signal processing unit 503' that performs processing on a signal from the second sensor unit 31', a computation unit 504 that performs computation (e.g., calculation of a cell transmission characteristic and calculation of a concentration of a substance or a gas) on signals from the first signal processing unit 503 and the second signal processing unit 503', and a control circuit 505 that controls the first driving unit 502, the second driving unit 502', and the computation unit 504.

Specific examples of the first signal processing unit 503 and the second signal processing unit 503' include I/V conversion amplifiers. In a case where the first sensor unit 31 and the second sensor unit 31' have photodiode structures, the I/V conversion amplifiers are advantageous because the I/V conversion amplifiers can convert output currents from the first sensor unit 31 and the second sensor unit 31' to voltages. From the viewpoint of reducing power consumption, the first driving unit 502 and the second driving unit 502' are preferably devices that supply pulsed signals (voltages or currents) to the first light source 20 and the second light source 20'.

As illustrated in FIG. 18, in the gas sensor of the sixteenth embodiment, the light reception/emission control unit 501 is connected to the first light source 20, the second light source 20', the first sensor unit 31, and the second sensor unit 31'. That is, the first driving unit 502 is connected to connection terminals at both ends of the first light source 20. The second driving unit 502' is connected to connection terminals at both ends of the second light source 20'. The first signal processing unit 503 is connected to connection terminals at both ends of the first sensor unit 31. The second signal processing unit 503' is connected to connection terminals at both ends of the second sensor unit 31'.

Figure 19A:
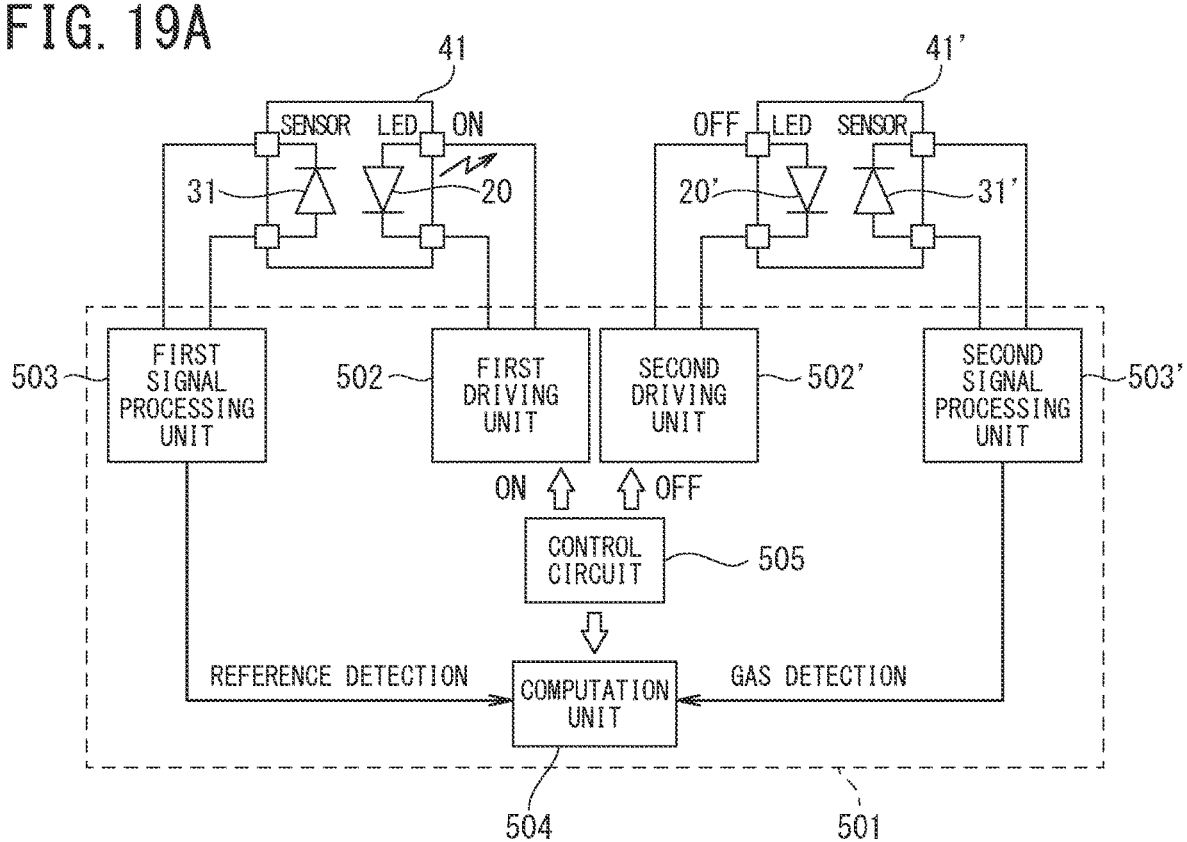
FIG. 19A is a view illustrative of a first signal flow while a first light source is driven and FIG. 19B is a view illustrative of a second signal flow while a second light source is driven in the sixteenth embodiment.
Figure 19B:
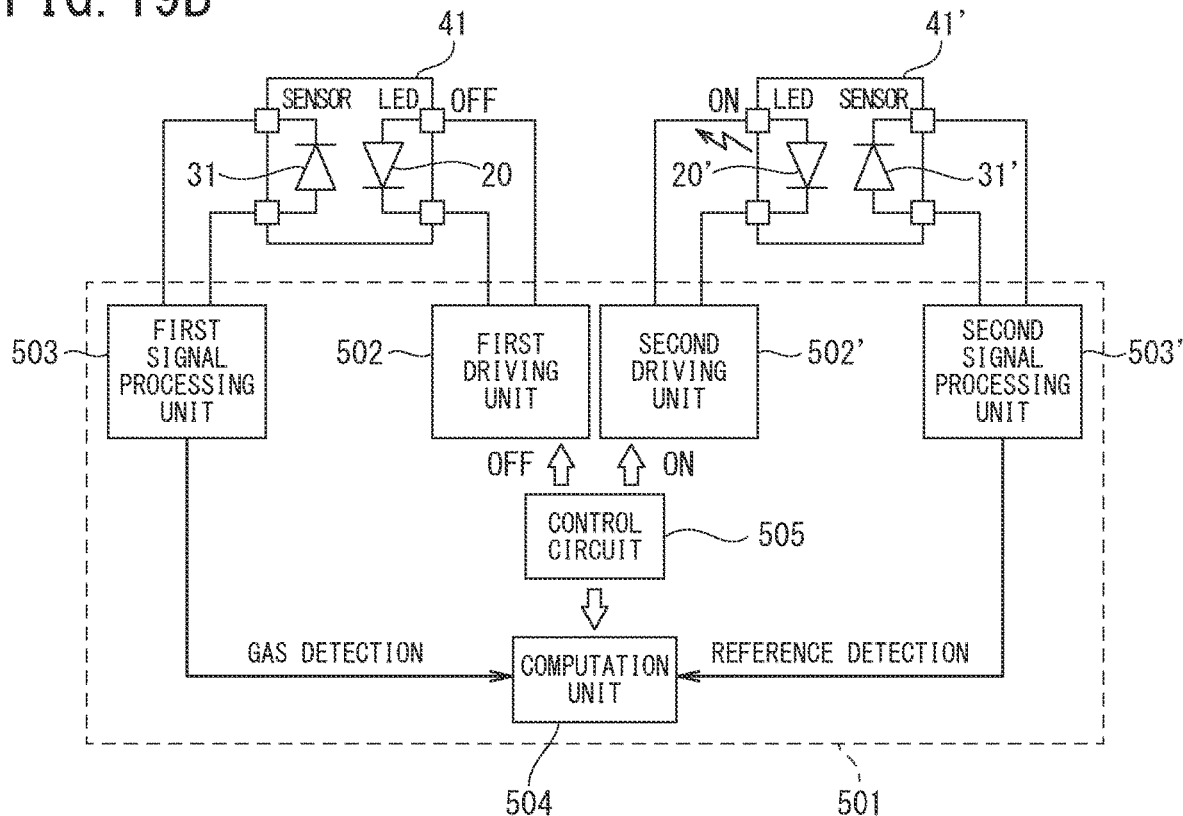

This connection enables detection of conditions (e.g., the presence and concentration of a specific gas, and the presence and concentration of fluid) of an optical path space in the gas cell 10. In the gas sensor illustrated in FIG. 18, the first light source 20 and the second light source 20' may be alternately driven. FIG. 19A illustrates a signal flow while the first light source 20 is driven. FIG. 19B illustrates a signal flow while the second light source 20' is driven.

Seventeenth Embodiment

Figure 20:
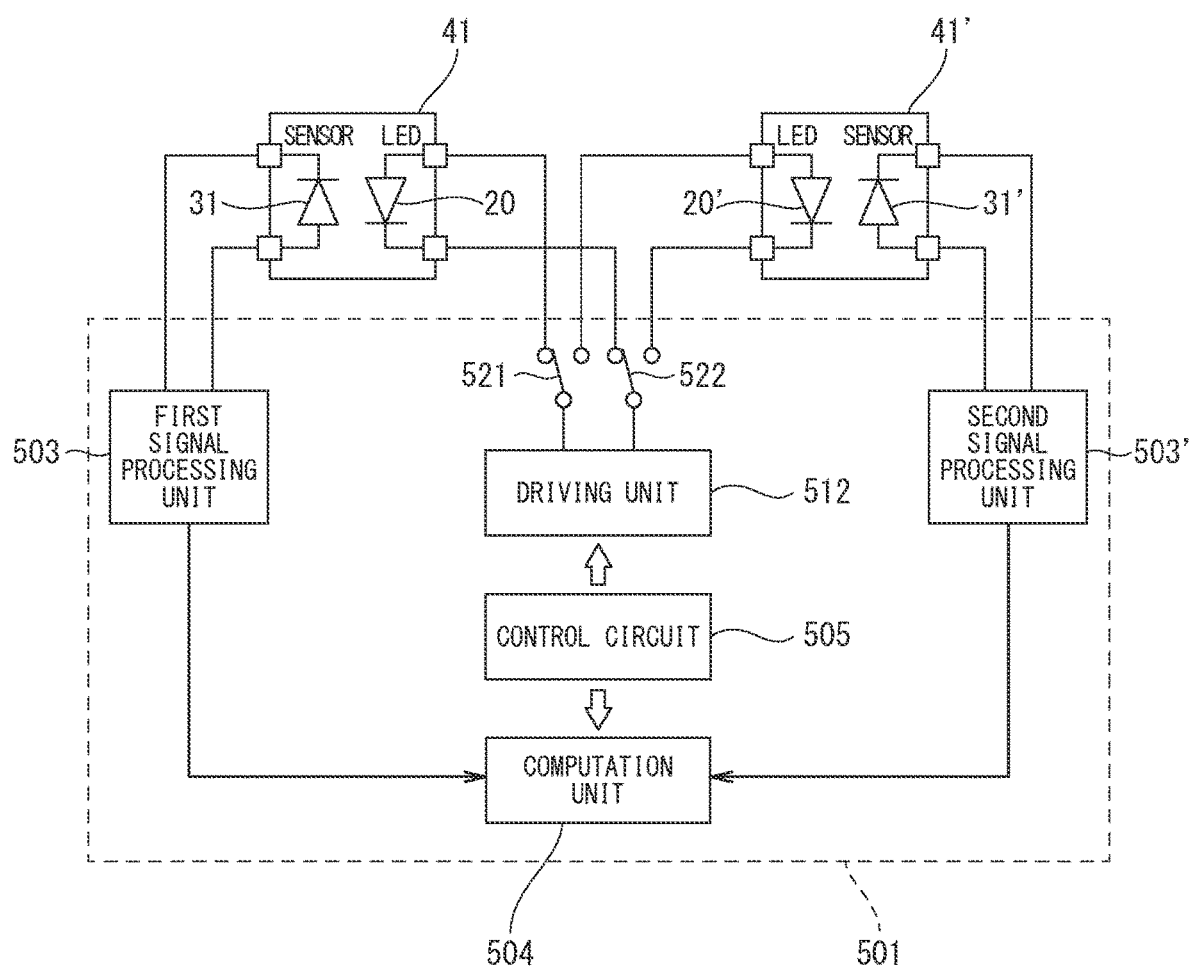
FIG. 20 is a view illustrative of an example configuration of a gas sensor according to a seventeenth embodiment of the present invention.

FIG. 20 is a conceptual illustration of an example configuration of a gas sensor according to a seventeenth embodiment of the present invention.

As illustrated in FIG. 20, the gas sensor of the seventeenth embodiment includes a driving unit 512 that alternately supplies electric power to a first light source 20 and a second light source 20' by using switches 521 and 522, for example. That is, in the seventeenth embodiment, the first light source 20 and the second light source 20' are alternately driven by the common driving unit 512. This alternate driving can be performed by using the switches 521 and 522.

In a case where a large current flows in a light-emitting portion, the size (e.g., a chip area occupied by a circuit in the case of LSI) of the driving unit increases in some cases. In view of this, the common driving unit can reduce the entire size of the circuit and LSI, thereby enhancing efficiency in using a chip. That is, in a case where a light emission current of the light-emitting portion is large, e.g., greater than or equal to 1 mA, greater than or equal to 10 mA, greater than or equal to 50 mA, or greater than or equal to 100 mA, the seventeenth embodiment is advantageous.

Eighteenth Embodiment

Figure 21:
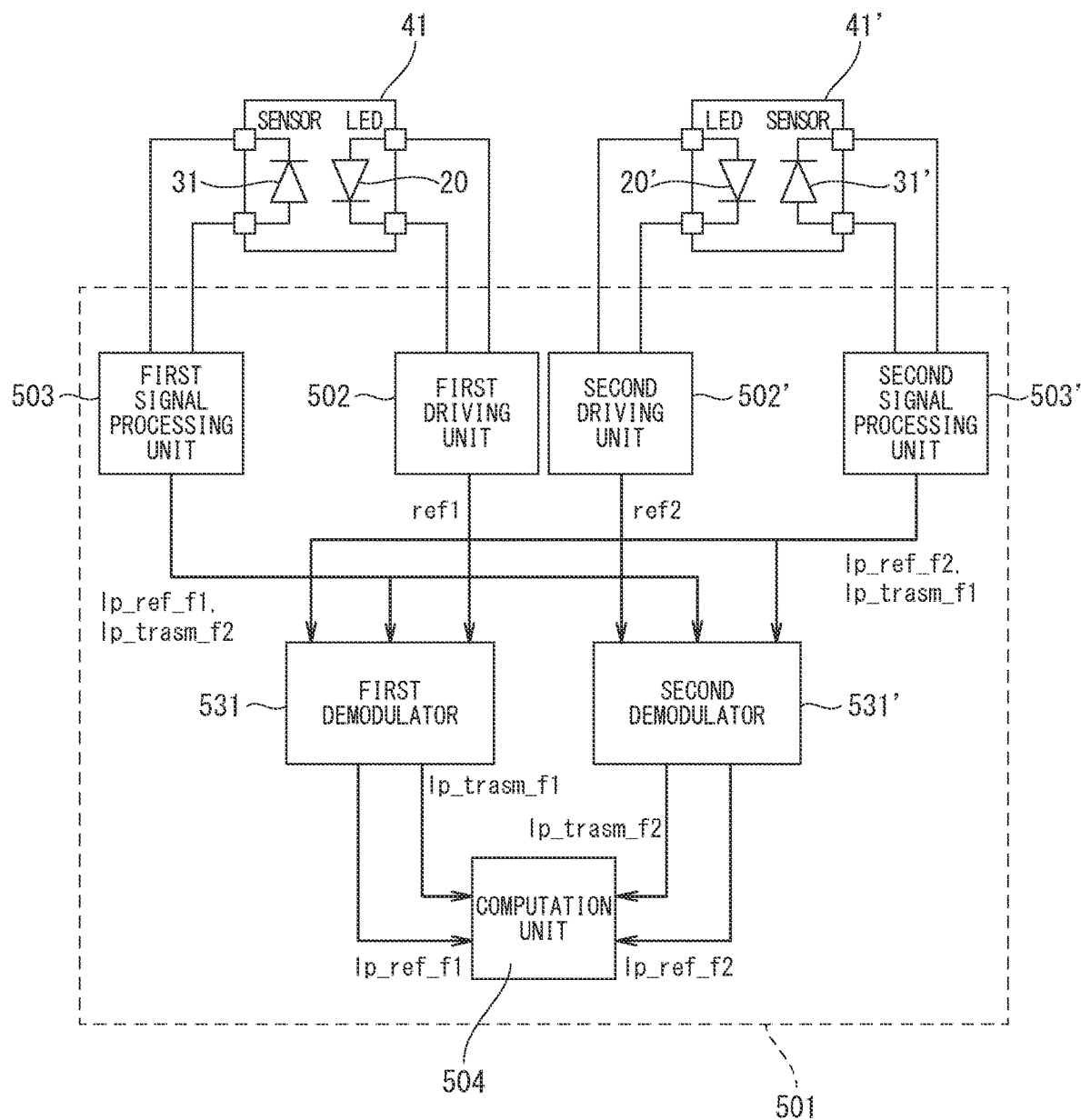
FIG. 21 is a view illustrative of an example configuration of a gas sensor according to an eighteenth embodiment of the present invention.

FIG. 21 is a conceptual illustration of an example configuration of a gas sensor according to an eighteenth embodiment of the present invention.

As illustrated in FIG. 21, in the gas sensor of the eighteenth embodiment, a light reception/emission control unit 501 includes a first driving unit 502 that drives the first light source 20 at a frequency F1, a second driving unit 502' that drives a second light source at a frequency F2, a first signal processing unit 503, a second signal processing unit 503, a first demodulator 531, a second demodulator 531', and a computation unit 504. It should be noted that F1 and F2 are different values (F1≠F2).

The first demodulator 531 demodulates two signal components modulated at the frequency F1, that is, a signal input from the first light source 20 to the second sensor unit 31' and a signal input from the first light source 20 to the first sensor unit 31. The second demodulator 531' demodulates two signal components modulated at the frequency F2, that is, a signal input from the second light source 20' to the first sensor unit 31 and a signal input from the second light source 20' to the second sensor unit 31'. The computation unit 504 receives signals from the first demodulator 531 and the second demodulator 531', and outputs a computation result in accordance with a transmittance (e.g., gas concentration) of a substance.

In the eighteenth embodiment, simultaneously with driving of the first light source 20 with a signal at the frequency F1, the second light source 20' is driven at the frequency F2 (F1≠F2). In the eighteenth embodiment, both the light-emitting portions can be driven without using a switch. Thus, a temperature difference is much less likely to occur between the first sensor unit 31 and the second sensor unit 31', and an accurate temperature compensation can be obtained.

In this case, a combination of two signals: a signal Ip_ref_f1 modulated from the first light source 20 at the frequency F1 and incident on the first sensor unit 31 through the inside of the first substrate 41; and a signal Ip_trasm_f2 modulated from the second light source 20' at the frequency F2 and incident on the first sensor unit 31 through an optical path space (i.e., a signal in accordance with light transmitted through the detection target substance) is a signal A detected by the first signal processing unit 503. A combination of two signals: a signal Ip_ref_f2 modulated from the second light source 20' at the frequency F2 and incident on the second sensor unit 31' through the inside of the second substrate; and a signal Ip_transm_f1 modulated from the first light source 20 at the frequency F1 and incident on the second sensor unit 31' through an optical path space (i.e., a signal in accordance with light transmitted through a detection target substance) is a signal B detected by the second signal processing unit 503'.

The first demodulator 531 receives the signal A, the signal B, and a synchronizing signal ref1 with the frequency F1, and outputs a demodulated signal Ip_ref_f1 and a demodulated signal Ip_trasm_f1. The second demodulator 531' receives the signal A, the signal B, and a synchronizing signal ref2 with the frequency F2, and outputs a demodulated signal Ip_ref_f2 and a demodulated signal Ip_transm_f2.

The first demodulator 531 and the second demodulator 531' may have any configuration as long as signals with amplitude components corresponding to the frequencies thereof can be separated from each other. Examples of the first demodulator 531 and the second demodulator 531' include a Lock-in Amp. The Lock-in Amp is advantageous in the present invention because the Lock-in Amp can extract only signals with the same frequency as that of the reference signal (a synchronizing signal similar to signals ref1 and ref2) from signals having various frequency components and output the extracted signals.

Nineteenth Embodiment

Figure 22:
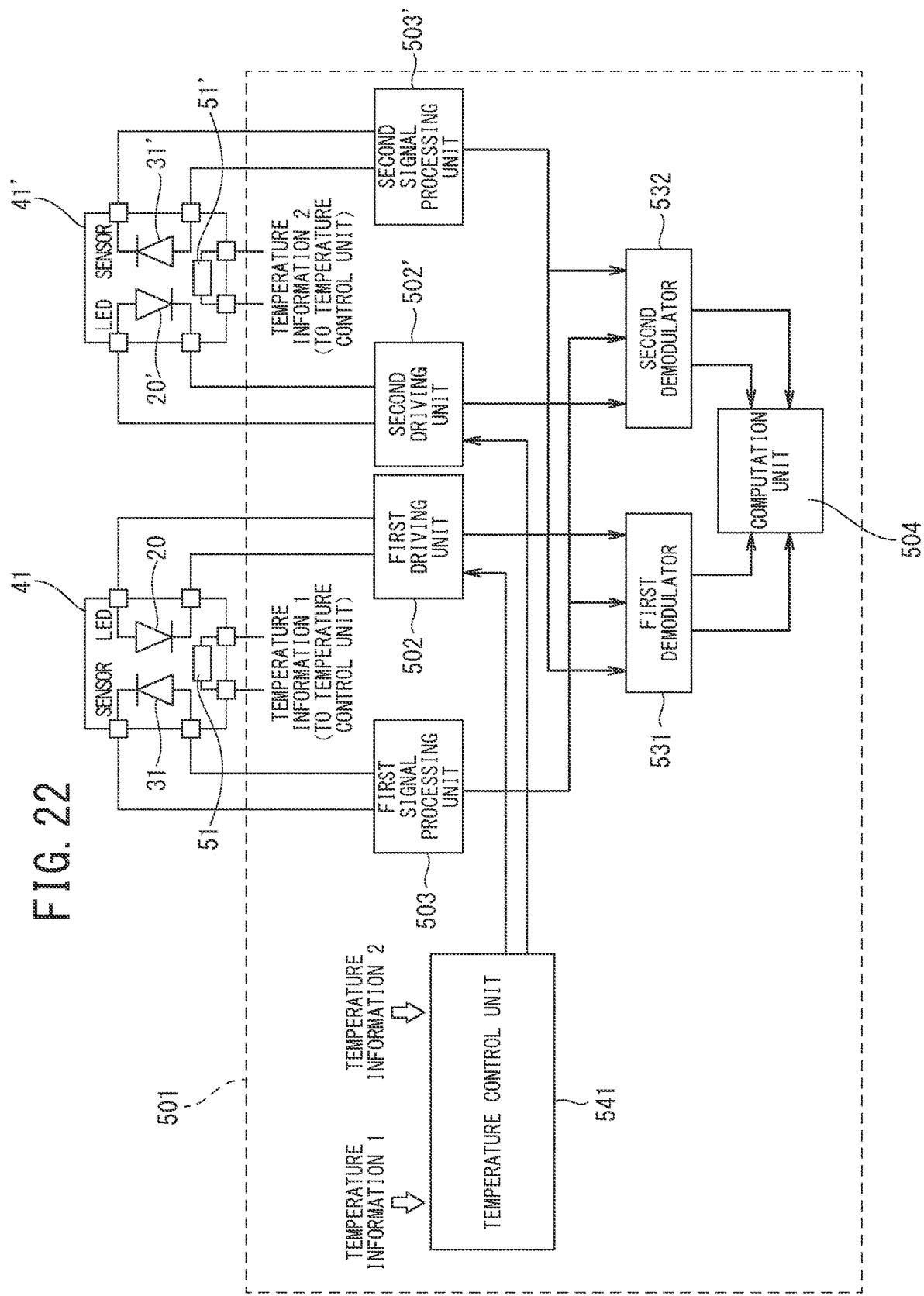
FIG. 22 is a view illustrative of an example configuration of a gas sensor according to a nineteenth embodiment of the present invention.

FIG. 22 is a conceptual illustration of an example configuration of a gas sensor according to a nineteenth embodiment of the present invention.

As illustrated in FIG. 22, the gas sensor of the nineteenth embodiment includes a first substrate 41 provided with a first temperature measuring unit 51 in addition to a first light source 20 and a first sensor unit 31 and a second substrate 41' provided with a second temperature measuring unit 51' in addition to a second light source and a second sensor unit.

Each of the first temperature measuring unit 51 and the second temperature measuring unit 51' has any structure as long as the first temperature measuring unit 51 and the second temperature measuring unit 51' have similar structures and a temperature of the first sensor unit 31 and a temperature of the second sensor unit 31' can be precisely measured. As a specific example, the first temperature measuring unit 51 and the second temperature measuring unit 51' may have photodiode structures similar to those of the light-emitting portions and the sensor units.

Figure 23:
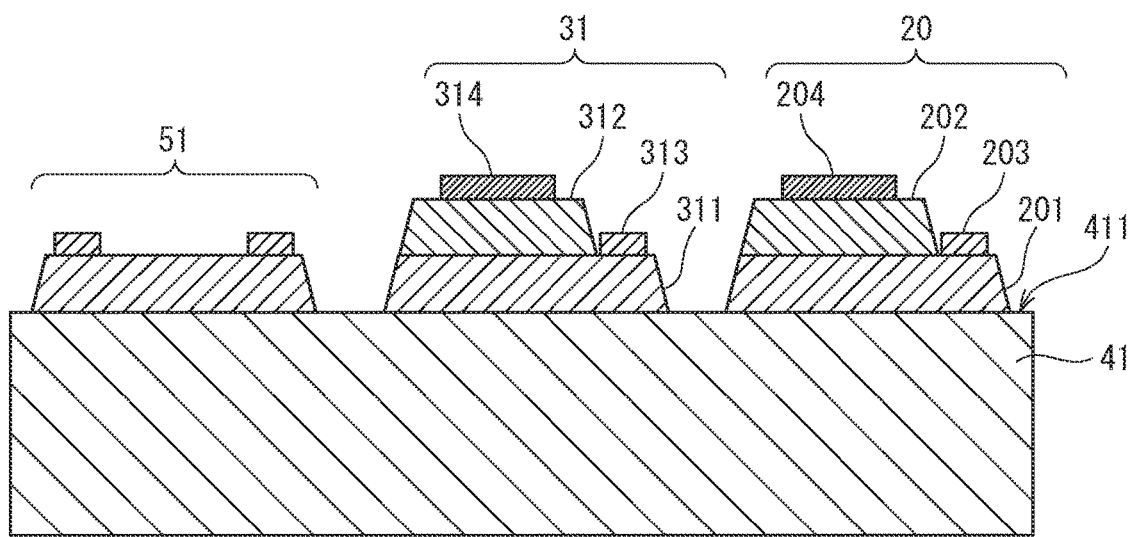
FIG. 23 is a view illustrative of an example of a temperature measuring unit in the nineteenth embodiment.

FIG. 23 illustrates a case where the first temperature measuring unit 51 has a thermistor structure. The first temperature measuring unit 51 preferably has a thermistor structure in some cases because the first temperature measuring unit 51 can be formed on the same substrate by the same fabrication process by using, for example, an N layer (preferably a semiconductor layer near a first principal surface of a substrate) of a photodiode. A thermistor can obtain an output signal in accordance with a temperature of a sensor unit by applying a current thereto. Although not shown, the second temperature measuring unit 51' may have a thermistor structure. In this case, advantages similar to those described above can be obtained.

Referring back to FIG. 22, the gas sensor of the nineteenth embodiment further includes a temperature control section 541. The temperature control section 541 receives temperature information from the first temperature measuring unit 51 and temperature information from the second temperature measuring unit 51', and outputs a control signal in accordance with electric power necessary for the first light source 20 and the second light source 20' in such a manner that a temperature of the first sensor unit 31 and a temperature of the second sensor unit 31' are equal to each other.

The nineteenth embodiment of the present invention is advantageous especially in a case where the first substrate 41 and the second substrate 41' are disposed away from each other. For example, in the case of measuring a concentration of a detection target substance showing a small light absorption in a specific wavelength, a long optical path is needed, and the first substrate 41 and the second substrate 41' need to be disposed away from each other in some designs. In this case, the first substrate 41 and the second substrate 41' are susceptible to the influence of thermal disturbance such as a temperature gradient. However, in the nineteenth embodiment, the temperature of the first sensor unit 31 and the temperature of the second sensor unit 31' are individually measured, and desired levels of electric power are applied to the first light source 20 and the second light source 20' in such a manner that the temperature of the first sensor unit 31 and the temperature of the second sensor unit 31' are equal to each other. In this manner the first sensor unit 31 and the second sensor unit 31' are at an identical temperature, thereby enabling accurate temperature compensation. A possible method for controlling (changing) electric power supplied to the light-emitting portion is to use the width of a pulse of current (or voltage), the amplitude of the pulse, or the duty ratio of the pulse. The duty ratio is also referred to as a duty value.

Twentieth Embodiment

Figure 24:
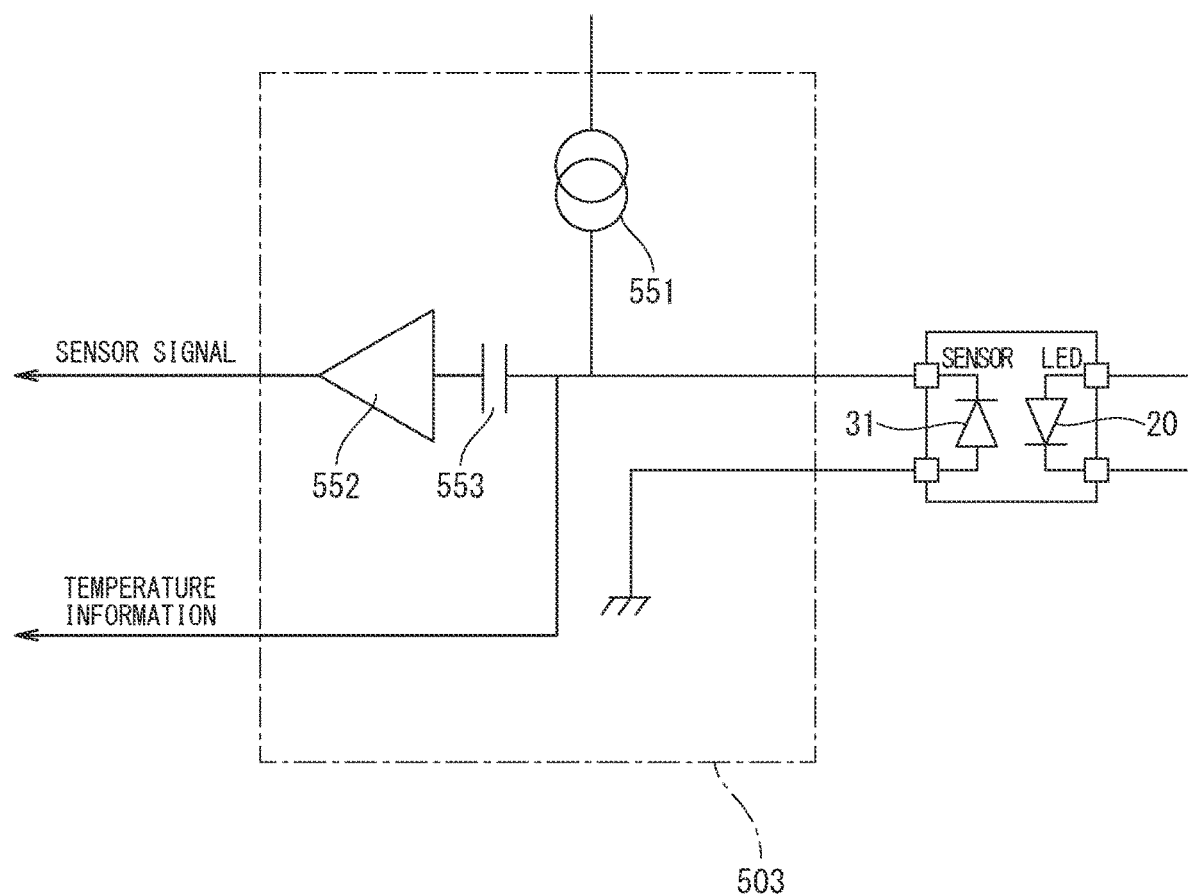
FIG. 24 is a view illustrative of an example configuration of a gas sensor according to a twentieth embodiment of the present invention.

FIG. 24 is a conceptual illustration of an example configuration of a gas sensor according to a twentieth embodiment.

In a manner similar to that in the nineteenth embodiment, the gas sensor of the twentieth embodiment measures the temperature of a first sensor unit and the temperature of a second sensor unit, and a temperature control section 541 outputs a control signal to a first driving unit and a second driving unit in order to supply electric power necessary for a first light source and a second light source. The twentieth embodiment is different from the nineteenth embodiment in a temperature measuring method. The gas sensor of the twentieth embodiment includes a first signal processing unit 503 (where only an example of the first signal processing unit 503 is illustrated in FIG. 24, and other circuits are not shown) that can calculates a resistance value of a first sensor unit 31. As illustrated in FIG. 24, the first signal processing unit 503 includes a current source 551 for causing a reverse current to flow in a photodiode (e.g., the first sensor unit 31), an amplifier 552, and a capacitor 553 connected to the current source 551 and an input terminal of the amplifier.

In the twentieth embodiment, a voltage value in accordance with a resistance value of a photodiode serves as a signal having temperature information. In a photodiode structure using InSb, InAlSb, or InAsSb, a resistance value of a reverse bias changes in accordance with temperature, and thus, a temperature of the first sensor unit 31 can be correctly measured. Accordingly, in the twentieth embodiment, more accurate temperature compensation can be obtained. A signal in accordance with an intensity of received light output from the first sensor unit 31 can be separated from a direct current component through the capacitor 553.

Although not shown, the second signal processing unit can have a configuration similar to that of the first signal processing unit illustrated in FIG. 24.

Twenty-First Embodiment

In each of the first through twenty-first embodiments of the present invention, an optical filter (band-pass filter) transmissive only to light in a specific wavelength band may be provided on an optical path from the first light source 20 to the second sensor unit 31' and/or an optical path from the second light source 20' to the first sensor unit 31.

Figure 25:
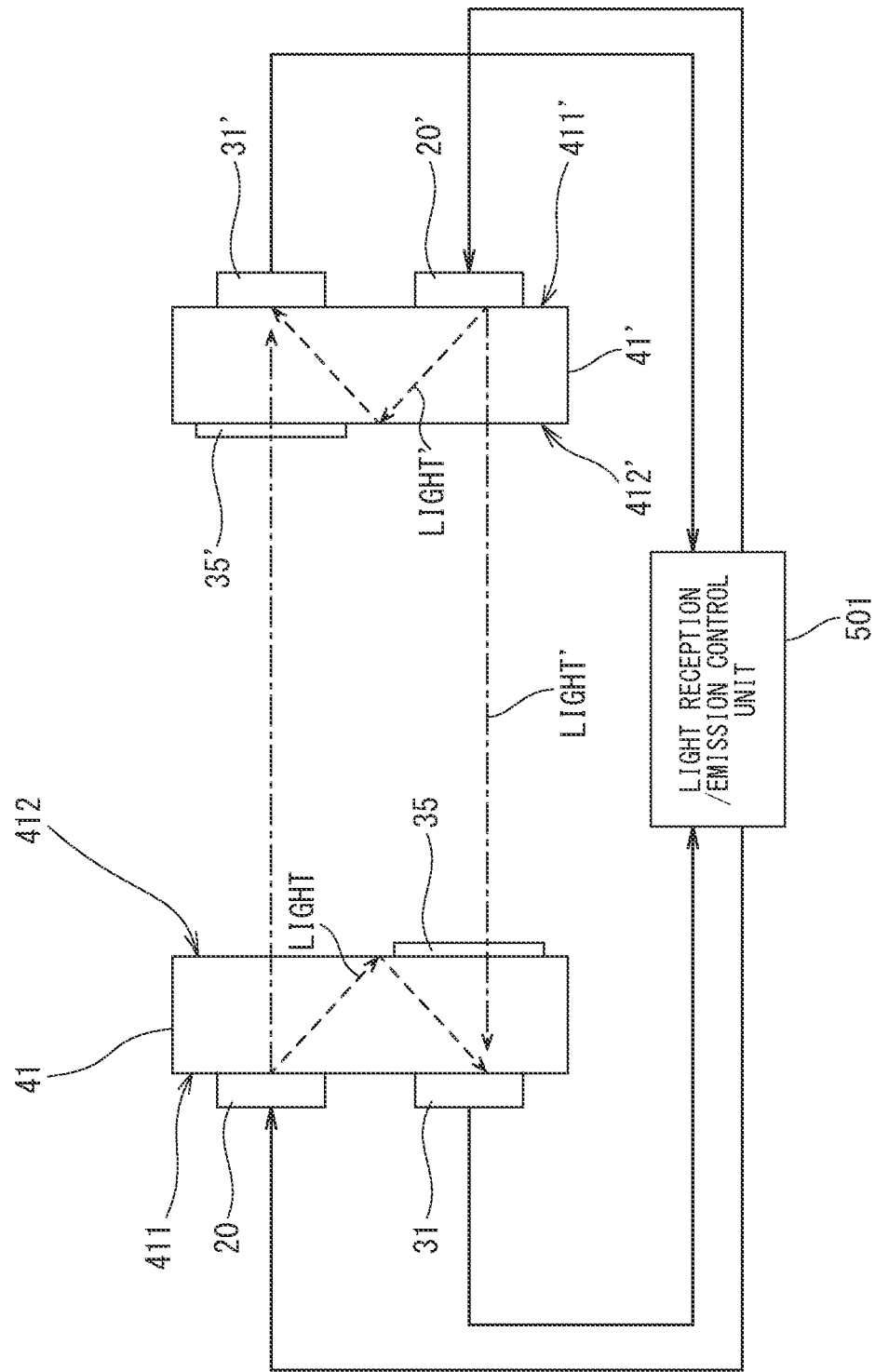
FIG. 25 is a view illustrative of an example configuration of a gas sensor according to a twenty-first embodiment of the present invention.

FIG. 25 is a conceptual illustration of an example configuration of a gas sensor according to a twenty-first embodiment of the present invention. As illustrated in FIG. 25, this gas sensor includes a band-pass filter 35 provided on a second principal surface 412 of a first substrate 41, and a band-pass filter 35' provided on a second principal surface 412' of the second substrate 41'. The band-pass filter 35 is disposed on an optical path from the second light source 20' to the first sensor unit 31. The band-pass filter 35' is disposed on an optical path from the first light source 20 to the second sensor unit 31'. The band-pass filters 35 and 35' are optical filters transmissive to different wavelengths, for example.

The gas sensor of the twenty-first embodiment is applicable to qualitative or quantitative detection of mixed substances (e.g., a mixed gas). For example, in a case where a detection target substance introduced into a cell is a mixed gas of a gas A and a gas B, suppose the gas A shows absorption at a wavelength 1 and the gas B shows absorption at a wavelength 2. In this case, the second substrate 41' is provided with the band-pass filter 35' transmissive to light with the wavelength 1, and the first substrate 41 is provided with the band-pass filter 35 transmissive to light with the wavelength 2. From an intensity of an output signal from the second sensor unit 31' provided on the second substrate 41' and an intensity of an output signal from the first sensor unit 31 provided on the first substrate 41, the gases A and B can be detected and the concentrations of the gases A and B can be obtained.

[Method for Computing Concentration of Specific Substance in Fluid]

Specific examples of a method for computing a concentration of a specific substance in fluid using a gas sensor according to the present invention will now be described. Suppose a signal output from the first sensor unit 31 and a signal output from the second sensor unit 31' in a case where the first light source 20 emits light are $Ip_{\_REF\_1}$ and $Ip_{\_TRANSM\_1}$, respectively. The signals $Ip_{\_REF\_1}$ and $Ip_{\_TRANSM\_1}$ can be expressed by Equation (7) and Equation (8). Suppose a signal output from the second sensor unit 31' and a signal output from the first sensor unit 31 in a case where the second light source 20' emits light are $Ip_{\_REF\_2}$ and $Ip_{\_TRANSM\_2}$, respectively. The signals $Ip_{\_REF\_2}$ and $Ip_{\_TRANSM\_2}$ can be expressed by Equation (9) and Equation (10).

$$Ip_{\_REF\_1} = Ri_1(T) \times \varphi1(T) \times \alpha \quad (7)$$

$$Ip_{\_TRASM\_1} = Ri_2(T) \times \varphi1(T) \times \beta \times (1 - A(C)) \quad (8)$$

$$Ip_{\_REF\_2} = Ri_2(T) \times \varphi2(T) \times \alpha \quad (9)$$

$$Ip_{\_TRASM\_2} = Ri_1(T) \times \varphi2(T) \times \beta \times (1 - A(C)) \quad (10)$$

where
A is an absorptance at a concentration of a measurement target substance,
C is a concentration of the measurement target substance,
$\varphi1$ is an emission intensity of a first light source,
$\varphi2$ is an emission intensity of a second light source,
$\alpha$ is a transmittance from the first light source to the first sensor unit
(similar to transmittance from the second light source to the second sensor unit),
$\beta$ is a light-extraction efficiency from the first substrate and the second substrate (or a transmittance from the first light source to the second sensor unit and a transmittance from the second light source to the first sensor unit in the case of no absorption by a detection target sub stance),
$Ip_{\_REF\_1}$ is a signal output from the first sensor unit when the first light source emits light,
$Ip_{\_TRASM\_1}$ is a signal output from the second sensor unit when the first light source emits light,
$Ip_{\_REF\_2}$ is a signal output from the second sensor unit when the second light source emits light,
$Ip_{\_TRASM\_2}$ is a signal output from the first sensor unit when the second light source emits light,
Ri1 is a sensitivity of the first sensor unit, and
Ri2 is a sensitivity of the second sensor unit.

In this alternate driving, the first driving unit and the second driving unit operate in response to a control signal from the control circuit unit 505, and the first driving unit and the second driving unit alternately emit light.

An example of a computation method by using the computation unit 504 will now be described. For example, the computation unit 504 can calculate a computation result 1 when the first light source emits light, and calculate a computation result 2 when the second light source emits light. That is, the computation result 1 and the computation result 2 can be expressed by Equation (11) and Equation (12):

$$\text{Computation result } 1 = Ip_{\_TRASM\_1} / Ip_{\_REF\_1} \quad (11)$$
$$= (Ri2(T) \times \beta \times (1 - A(C))) / (Ri1(T) \times \alpha)$$

$$\text{Computation result } 2 = Ip_{\_TRASM\_2} / Ip_{REF\_2} \quad (12)$$
$$= (Ri1(T) \times \beta \times (1 - A(C))) / (Ri2(T) \times \alpha)$$

If a temperature characteristic Ri1 (T)=g1 (T) of the first sensor unit is equal to, or proportional to, a temperature characteristic Ri2 (T)g2 (T) of the second sensor unit, a computation result $1 \propto (1-A(C))$ is obtained, and similarly a computation result $2 \propto (1-A(C))$ is obtained. Thus, temperature dependency as a gas sensor can be eliminated, thereby obtaining a true absorptance in absorption by gas molecules. When the computation result 1 is equal to the computation result 2, a final computation result is supposed to be a computation as expressed by Equation (13):

$$\text{Computation result 3} = (\text{computation result 1} + \text{computation result 2})/2 \quad (13)$$

Using the computation result expressed by Equation (9), from the Lambert-Beer law, a measurement target substance concentration C can be extracted from (1−A(C)).

Here, it was assumed that $\alpha$ and $\beta$ do not change depending on wavelength and temperature. However, even if $\alpha$ and $\beta$ change, a temperature of the first substrate and/or the second substrate or the cell is measured, and a measurement result may be used for temperature compensation.

[Compensation for Change with Time]

As seen from Equations (7) through (13), since the light amount of the light-emitting portion does not appear in the computation result, even when the light-emitting portion degrades, that is, the light emission efficiency changes, a concentration computation result of a detection target substance does not change. In the gas sensor according to the present embodiment, the first light source 20 and the first sensor unit 31 are formed on the same substrate (the first substrate 41), and a signal based only on light emitted from the first light source 20 can be output. Thus, the amount of light emission from the first light source 20 can be correctly measured. The same holds for the amount of light emitted from the second light source 20'. In a case where the light-emitting portion is constituted by a large number of light-emitting elements, arrangement of light-emitting elements of the light-emitting unit 20 and light-receiving elements of the first sensor unit 31 is appropriately designed so as to enable measurement of quantities of light emitted from the light-emitting elements.

An offset due to a disturbance or a circuit can be removed by continuously turning the light-emitting portion on and off (pulsed driving), reading signals from the first sensor unit and the second sensor unit when the light-emitting portion is on and signals from the first sensor unit and the second sensor unit when the light-emitting portion is off, and utilizing a signal difference thereof. This is because an offset due to a circuit or a disturbance always occurs irrespective of on/off of the light-emitting portion, and thus, the offset component can be removed by taking a signal difference between the on state and the off state.

Advantages obtained by removing an offset are more significant in a case where a switching frequency between on and off is set at a sufficiently large value with respect to radiation of a disturbance and frequencies of fluctuations of a circuit offset. Specifically, in a case where a variable frequency band of the disturbance and the offset is 0 to 1 kHz, the on/off switching frequency is set at a level about 10 times (10 kHz) as high as the variable frequency band. In general, a power spectrum of this offset is inversely proportional to a frequency f, that is, is 1/f (so called pink noise, 1/f noise). Thus, the switching frequency between on and off states is set in a frequency band in which 1/f noise does not appear. In addition, in the seventh and nineteenth embodiments, a sufficient frequency difference $\Delta f$ needs to be provided so as to avoid signal interference between the first demodulator and the second demodulator. In addition to the signal modulation technique between the on and off states described above, amplitude modulation (AM) typically used in a communication system may be used.

When the light-emitting portion is driven with a low current and the gas cell is designed to have an excessive length in order to reduce power consumption of the entire gas sensor, a sufficient S/N ratio cannot be obtained in some cases. That is, although a short gas path is needed, as the gas path becomes shorter, a change in signal in accordance with temperature increases more greatly than a change in signal in accordance with a change in gas concentration. In such case, an effective temperature compensation technique is inevitable.

The first sensor unit and the second sensor unit are preferably quantum sensors because such quantum sensors can operate at high speed (has sufficient responsiveness to high-speed optical pulse). In a quantum sensor, since an internal resistance of a sensor changes in accordance with temperature, an internal temperature of the gas sensor can be correctly determined by reading an internal resistance value of this sensor.

<Others>

The present invention is not limited to the foregoing embodiments. A design change, for example, may be applied to the embodiments based on the knowledge of those skilled in the art, and the first aspect and the second aspect, which are examples of the present embodiment, and the first through twenty-first embodiments, which are specific examples of the present embodiment, may be combined in any manner, and variations provided with such changes are included in the scope of the invention.

The gas sensor according to present invention is not limited to an infrared ray gas sensor, and may be an ultraviolet radiation gas sensor, for example. In this case, the first light source and the second light source radiate ultraviolet rays, and a part of the radiated ultraviolet rays is received by the first sensor unit, and the other part of the ultraviolet rays is received by the second sensor unit.

The use of the technique described above enables an accurate concentration measuring apparatus independent of an environmental temperature. Examples of application of the concentration measuring apparatus include a gas sensor.

EXAMPLES

An example of the present invention and a comparative example thereof will be described.

Example

An example of the present invention will be described using the gas sensor according to the tenth embodiment illustrated in FIG. 10. Semi-insulating GaAs substrates were used as the first substrate 41 and the second substrate 42, an LED with a PIN structure that can emit light having a wavelength around 4.3 μm was used as the first light source 20, and photodiodes with PIN structures that can detect a wavelength around 4.3 μm were used as the first sensor unit 31 and the second sensor unit 32.

All the first light source (LED) 20, the first sensor unit 31, and the second sensor unit 32 have similar laminated structures, and an n-type AlInSb with a thickness of 1 μm, an i-type active layer with a thickness of 2 μm, an AlInSb barrier layer having a thickness of 0.02 μm and a band gap larger than that of the i layer, and a p-type AlInSb with a thickness of 0.5 μm are deposited over a GaAs substrate with a thickness of 230 μm by a molecular beam epitaxy (MBE) technique.

The first substrate 41 and the second substrate 42 had the same area of 0.53 mm$^2$. An LED area (light emission area) of the first light source 20 on the first substrate 41 was 0.26 mm$^2$, and an area (light-receiving surface area) of a light-receiving portion of the first sensor unit 31 was 0.025 mm$^2$. A light-receiving surface area of the second sensor unit 32 was 0.28 mm$^2$. The number of light-receiving portions on the first sensor unit 31 was 36, and the number of light-receiving portions of the second sensor unit 32 was 396. The first substrate 41 and the second substrate 42 were subjected to the same wafer process. First, a wet etching was performed to form MESA elements (a light-receiving element and a light-emitting element), and then Si$_3$N$_4$ was formed as an insulation layer. Lastly, a contact hole for electrical connection to an n-type layer and a p-type layer was formed, and then, a metal interconnection was formed. In the metal interconnection, Ti was used as an adhesion layer, and Au was used thereon to reduce an interconnect resistance.

As the encapsulating resin 200, a resin of Chipcoat G8345-6 produced by NAMICS CORPORATION and not transmissive to light with a wavelength of 4.3 μm was used. An aluminum cylinder whose inner surface was mirror finished was used as the gas cell 10. A distance between the first substrate 41 and the second substrate 42 was 20 mm (a distance corresponding to a gas cell length). The dimensions of the entire gas sensor were 10×10×25 mm$^3$.

A pulse generator (pulse generating unit) that outputs a pulse of square waves was used as the light source power supply unit 101 for supplying power to the first light source 20. A first lockin amplifier was used as the first amplifying unit 102, and a second lockin amplifier was used as the second amplifying unit 103. A trigger signal of the pulse generator was used as a synchronizing signal for both the lockin amplifiers. A detection target gas used in this experiment was carbon dioxide ($CO_2$).

[Measurement Experiment]

Figure 26:
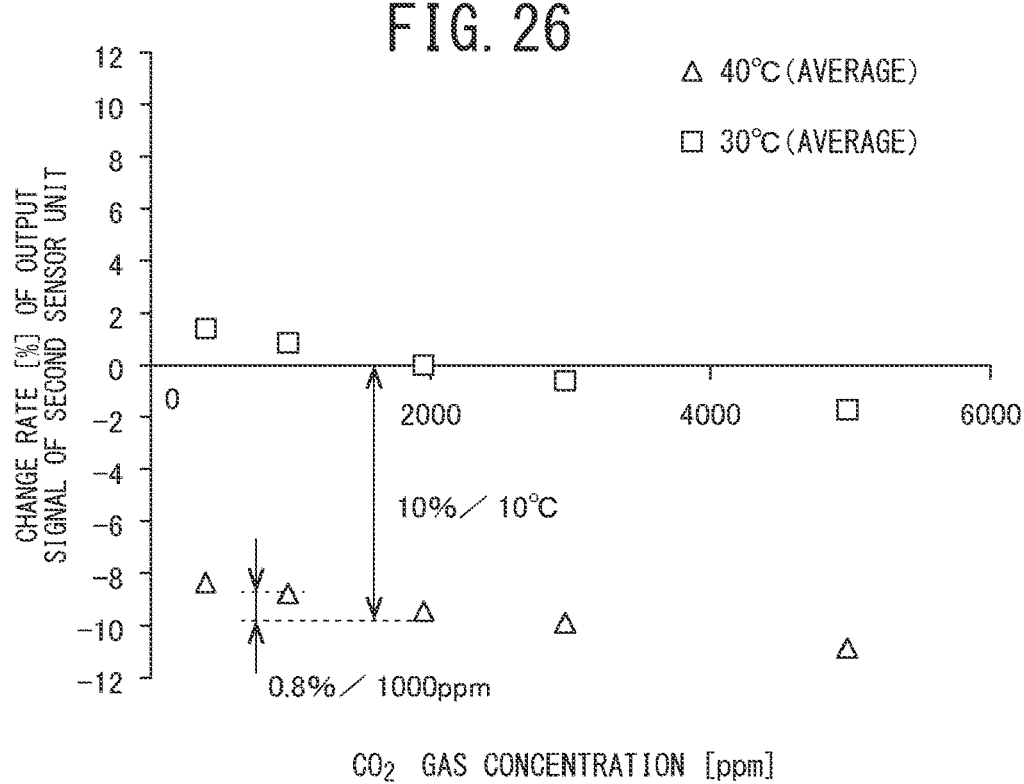
FIG. 26 is a graph showing results obtained in an example of the present invention and a relationship between a $CO_2$ gas concentration and a temperature with respect to a change rate of an output signal from a second sensor unit.
Figure 27:
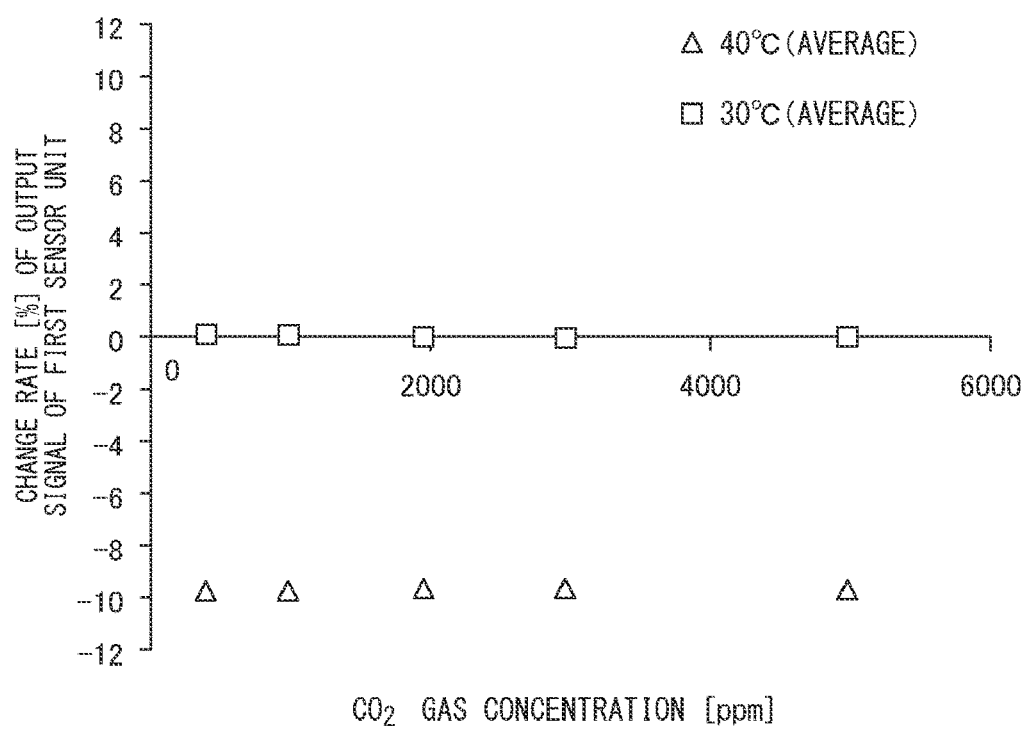
FIG. 27 is a graph showing results obtained in the example of the present invention and a relationship between a $CO_2$ gas concentration and a temperature with respect to a change rate of an output signal from a first sensor unit.

Signals output from the second sensor unit 32 (using a signal at 30° C. and 2000 ppm as a standard) in a case where a gas sensor was placed in a temperature-controlled bath, the temperature-controlled bath was set at 30° C. and 40° C., and carbon dioxide gases in concentrations of 500 ppm, 1000 ppm, 2000 ppm, 3000 ppm, and 5000 ppm were introduced into the gas cell 10 were plotted in FIG. 26, and signals output from the first sensor unit 31 on the first substrate 41 were plotted in FIG. 27.

Figure 28:
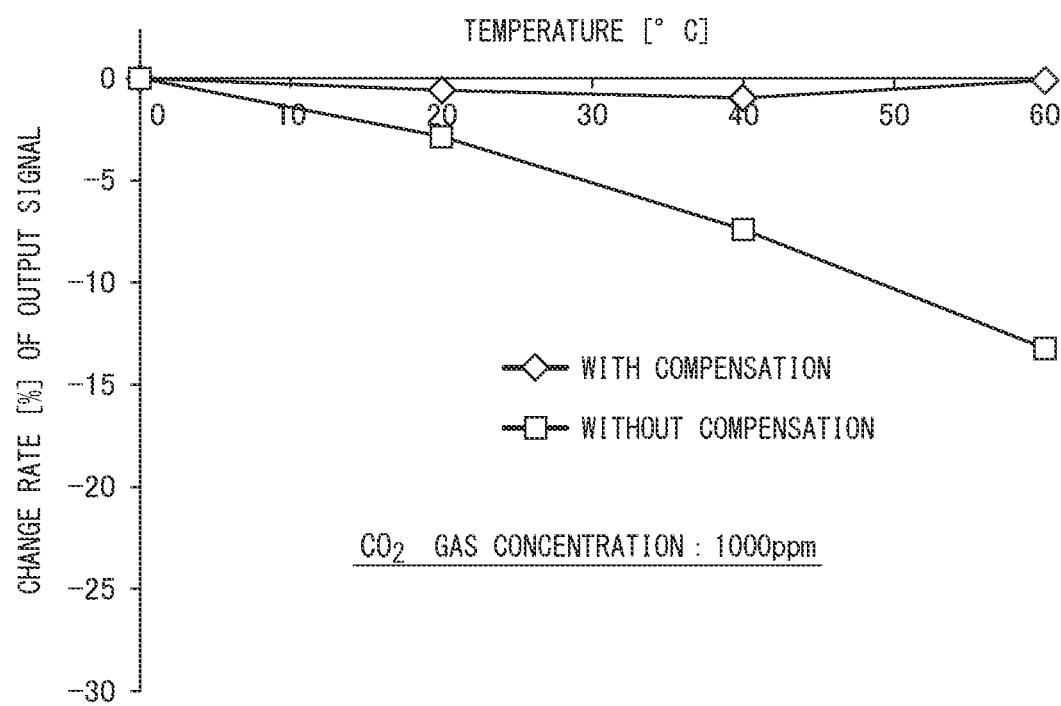
FIG. 28 is a graph showing results obtained in the example of the present invention and a relationship between a temperature and the presence of compensation with respect to a change rate of an output signal from a second sensor.

FIG. 28 indicates a change rate of an output signal (an output signal from the second sensor unit/an output signal from the first sensor unit) in application of temperature compensation of the present embodiment and a change rate of an output signal (original output signal from the second sensor unit) in no application of temperature compensation (using a signal at 0° C. as a standard) in a case where the temperature was changed from 0 to 60° C. with a constant carbon dioxide gas concentration (of 1000 ppm).

[Results]

As demonstrated in FIG. 26, it was observed that when the concentration of the carbon dioxide gas is changed to 500 to 5000 ppm, the output signal from the second sensor unit 32 changes by about 0.8%/1000 ppm in each of the cases where the environmental temperature was 30° C. and 40° C. It was also observed that when the temperature was changed by 10° C. (i.e., from 30° C. to 40° C.), the output signal also changed by 10%/10° C. That is, it can be understood that when an environmental temperature changes, a signal change much greater than a change (0.8%/1000 ppm) of an output signal in a gas concentration range intended to be detected occurs, and a gas concentration cannot be correctly detected.

On the other hand, as demonstrated in FIG. 27, an output signal from the first sensor unit 31 is affected by temperature in a manner similar to the second sensor unit 32, but is not affected by a gas concentration.

As demonstrated in FIG. 28, in a case where temperature compensation is not performed and a temperature was changed by 0 to 60° C., a signal change of about 15% occurs. On the other hand, in application of temperature compensation according to the present embodiment, that is, in the case of using, as an output, a signal obtained by dividing a signal from the second sensor unit 32 by a signal from the first sensor unit 31, the influence of temperature can be significantly reduced to 1% or less. From the foregoing, it was demonstrated that the configuration of the present embodiment can significantly enhance gas measurement accuracy.

COMPARATIVE EXAMPLE

[Measurement Experiment]

A comparative example will now be described using a gas sensor illustrated in FIG. 29B.

As illustrated in FIG. 29B, as a comparative example, a configuration similar to that of the example except that a first sensor unit (reference sensor) 931 and a second sensor unit (detection sensor) 932 were disposed to face a first light source, a reference band-pass filter (selectively transmissive to light in a wavelength band having a center wavelength of 3.9 μm and a full width at half maximum of 0.2 μm) f1 was provided to a reference sensor 931, and a detection band-pass filter (selectively transmissive to light in a wavelength band having a center wavelength of 4.3 μm and a full width at a half maximum of 0.2 μm) f2 was provided to a detection sensor 932, and a measurement similar to that of the example was performed.

[Results]

As demonstrated in Table 1, in the comparative example, an S/N ratio between a main sensor signal (S2) and a reference sensor signal (S1) was 3194. On the other hand, in the example of the present invention, S1 was increased 100 times so that an S/N ratio of S2/S1 was 4380, and 1.4-times improvement was observed.

TABLE 1

|  |  | Comparative example | Example |  |
|---|---|---|---|---|
| Reference signal (S1) | Signal | 500 | 50000 | pArms |
|  | Noise | 0.129 | 0.129 | pArms |
|  | S/N ratio 1 | 3885 | 388544 |  |
| Main sensor signal (S2) | Signal | 500 | 500 | pArms |
|  | Noise | 0.129 | 0.772114 | pArms |
|  | S/N ratio 2 | 3885 | 648 |  |
| S2/S1 | Signal | 1 | 0.01 |  |
|  | Noise | 0.000313121 | 2.28301E−06 |  |
|  | S/N entire ratio | 3194 | 4380 |  |

In this manner, the present invention is applicable to various gas concentration sensors, and is applicable to, for example, a gas concentration sensor of carbon dioxide ($CO_2$). In an environment where a human is active on the earth, a concentration of carbon dioxide is considered to be several hundreds ppm to 5000 ppm. The concentration of carbon dioxide can exceed 5000 ppm in some cases. However, in many cases, the concentration of carbon dioxide needs to be monitored from the viewpoint of safety control, medical field, or comfort of environment. According to the present invention, carbon dioxide in a relatively low concentration can be monitored with a resolution of 200 ppm, or less than or equal to 100, 50, or 10 ppm in a wide temperature range.

INDUSTRIAL APPLICABILITY

The present invention enables a gas sensor that does not need temperature compensation and degradation compensation with a simpler configuration.

REFERENCE SIGNS LIST 10 gas cell
20 first light source

20' second light source
31 first sensor unit
31', 32 second sensor unit
40 substrate (common substrate)
41 first substrate
41', 42 second substrate
50 light-blocking portion
51 first temperature measuring unit
51' second temperature measuring unit
60 light reflection unit
70 control layer
101 light source power supply unit
102 first amplifying unit
103 second amplifying unit
104 gas concentration computing unit
105 temperature measuring unit
106 driving signal supply unit
200 encapsulating resin
201, 311, 321, 201', 311' semiconductor layer of first conductivity type
202, 312, 322, 202', 312' semiconductor layer of second conductivity type
203, 204, 313, 314, 323, 324, 203', 204', 313', 314' electrode
411 first principal surface
412 second principal surface
501 light reception/emission control unit
502 first driving unit
502' second driving unit
503 first signal processing unit
503' second signal processing unit
504 computation unit
505 control circuit
512 driving unit
521, 522 switch
531 first demodulator
531' second demodulator
541 temperature control section
551 current source
552 amplifier
553 capacitor
701 light reflection layer
910 gas cell
920 first light source
930 infrared ray sensor
931 reference sensor
932 detection sensor

The invention claimed is:
1. A sensor for detecting a target substance comprising:
a first light source;
a first sensor unit and a second sensor unit disposed to receive light output from the first light source;
a first substrate having a first principal surface and a second principal surface opposite to the first principal surface, the first light source and the first sensor unit being provided on the first principal surface of the first substrate; and
a second substrate having a first principal surface and a second principal surface opposite to the first principal surface, the second sensor unit being provided on the first principal surface of the second substrate, wherein
the first sensor unit is disposed at a location where light output from the first light source and reflected on the second principal surface of the first substrate strikes the first principal surface of the first substrate, and
the first substrate and the second substrate are discrete parts and spatially separate from each other.

2. The sensor according to claim 1, wherein the sensor is a nondispersive infrared (NDIR) gas sensor.
3. The sensor according to claim 2, wherein a concentration of the target substance is obtained from amount of infrared rays absorbed by the target substance.
4. The sensor according to claim 1, further comprising:
a computation unit configured to receive an output signal from the first sensor unit and an output signal from the second sensor unit.
5. The sensor according to claim 4, wherein the output signal from the first sensor unit is a reference signal and the output signal from the second sensor unit is a signal that is changed in accordance with the target substance.
6. The sensor according to claim 4, wherein the computation unit is configured to calculate a concentration of the target substance based on a ratio of the output signal from the first sensor unit and the output signal from the second sensor unit.
7. The sensor according to claim 1, wherein the second sensor unit is disposed at a location where light output from the first light source radiates from the first substrate and strikes the second sensor unit.
8. The sensor according to claim 1, wherein the second sensor unit is disposed at a location where light output from the first light source passes through the inside of the second substrate, and strikes the second sensor unit.
9. The sensor according to claim 1, further comprising:
an optical filter disposed on an optical path from the first light source to the second sensor unit, the optical filter being transmissive only to a specific wavelength band.
10. The sensor according to claim 1, further comprising:
a cell includes an inlet for introducing the target substance, wherein
the second sensor unit is disposed at a location where light output from the first light source and then radiated into the cell, and strikes the second sensor unit.
11. The sensor according to claim 10, further comprising:
a light reflection unit disposed in the cell and configured to reflect light output from the first light source toward the second sensor unit.
12. The sensor according to claim 1, wherein the first substrate is a GaAs substrate.
13. The sensor according to claim 1, wherein the first light source and the first sensor unit have compound semiconductor laminates directly formed on the first principal surface of the first substrate respectively.
14. The sensor according to claim 1, wherein the first sensor unit and the second sensor unit are made of an identical material and have an identical laminated structure.
15. The sensor according to claim 14, wherein the laminated structure is a diode structure including at least two types of layers of a p-type semiconductor and an n-type semiconductor and includes indium or antimony.
16. The sensor according to claim 1, wherein
each of the first sensor unit and the second sensor unit includes a plurality of light-receiving portions having an identical structure.
17. The sensor according to claim 1, wherein the first light source, the first sensor unit and the second sensor unit have a Group III-V compound semiconductor respectively.
18. A sensor for detecting a target substance comprising:
a first light source;
a first sensor unit and a second sensor unit disposed to receive light output from the first light source;
a first substrate having a first principal surface and a second principal surface opposite to the first principal surface, the first light source and the first sensor unit being provided on the first principal surface of the first substrate; and a second substrate having a first principal surface and a second principal surface opposite to the first principal surface, the second sensor unit being provided on the first principal surface of the second substrate, wherein the first sensor unit is disposed at a location where light output from the first light source and reflected on the second principal surface of the first substrate strikes the first principal surface of the first substrate, and the first substrate and the second substrate are disposed at a prescribed distance from each other.

19. The sensor according to claim 18, wherein the first substrate and the second substrate are disposed at a prescribed distance from each other so that to form a space outside the first substrate and second substrate, between an optical path from the first light source to the second sensor unit.

20. A sensor for detecting a target substance comprising:
a first light source;
a first sensor unit and a second sensor unit disposed to receive light output from the first light source;
a first substrate having a first principal surface and a second principal surface opposite to the first principal surface, the first light source and the first sensor unit being provided on the first principal surface of the first substrate; and
a second substrate having a first principal surface and a second principal surface opposite to the first principal surface, the second sensor unit being provided on the first principal surface of the second substrate, wherein
the first sensor unit is disposed at a location where light output from the first light source and reflected on the second principal surface of the first substrate strikes the first principal surface of the first substrate, and
the target substance is introduced into a space between an optical path from the first light source to the second sensor unit.

* * * * *